(12) United States Patent
Garrison et al.

(10) Patent No.: US 9,179,909 B2
(45) Date of Patent: Nov. 10, 2015

(54) SUTURE DELIVERY DEVICE

(71) Applicant: Silk Road Medical, Inc., Sunnyvale, CA (US)

(72) Inventors: Michi E. Garrison, Sunnyvale, CA (US); Gregory M. Hyde, Sunnyvale, CA (US); Richard J. Renati, Los Gatos, CA (US); Alan K. Schaer, San Jose, CA (US); Tony M. Chou, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 0 days.

(21) Appl. No.: 14/071,485

(22) Filed: Nov. 4, 2013

(65) Prior Publication Data

US 2014/0058414 A1     Feb. 27, 2014

Related U.S. Application Data

(63) Continuation of application No. 12/633,730, filed on Dec. 8, 2009, now Pat. No. 8,574,245, which is a continuation-in-part of application No. 12/540,341, filed on Aug. 12, 2009.

(Continued)

(51) Int. Cl.
*A61B 17/04*     (2006.01)
*A61B 17/00*     (2006.01)
(Continued)

(52) U.S. Cl.
CPC ......... *A61B 17/0469* (2013.01); *A61B 17/0057* (2013.01); *A61M 25/04* (2013.01); *A61M 25/0662* (2013.01); *A61B 5/027* (2013.01); *A61B 2017/00654* (2013.01); *A61B 2017/00663* (2013.01); *A61B 2017/047* (2013.01); *A61B 2017/0472* (2013.01);
(Continued)

(58) Field of Classification Search
CPC ........... A61B 17/0469; A61B 17/0057; A61B 2017/0475; A61B 2017/0474
See application file for complete search history.

(56) References Cited

U.S. PATENT DOCUMENTS

| 4,301,803 A | 11/1981 | Handa et al. |
|---|---|---|
| 4,493,707 A | 1/1985 | Ishihara |

(Continued)

FOREIGN PATENT DOCUMENTS

| EP | 0 669 103 A1 | 8/1995 |
|---|---|---|
| JP | S59-161808 U | 10/1984 |

(Continued)

OTHER PUBLICATIONS

Bergeron et al. (2008) MEET Presentation, Cannes, French Riviera "Why I do not use routine femoral access for CAS".

(Continued)

*Primary Examiner* — Thomas McEvoy
(74) *Attorney, Agent, or Firm* — Fred C. Hernandez; Mintz Levin Cohn Ferris Glovsky and Popeo, P.C.

(57) ABSTRACT

A suture-based vessel closure device can perform the dilation of an arteriotomy puncture and does not require previous dilation of the arteriotomy puncture by a separate device or by a procedural sheath dilator. The suture-based vessel closure device can place one or more sutures across the vessel access site such that, when the suture ends are tied off after sheath removal, the stitch or stitches provide hemostasis to the access site.

12 Claims, 37 Drawing Sheets

Related U.S. Application Data

(60) Provisional application No. 61/165,392, filed on Mar. 31, 2009, provisional application No. 61/162,173, filed on Mar. 20, 2009, provisional application No. 61/138,403, filed on Dec. 17, 2008, provisional application No. 61/097,812, filed on Sep. 17, 2008, provisional application No. 61/088,680, filed on Aug. 13, 2008.

(51) Int. Cl.
*A61M 25/04* (2006.01)
*A61M 25/06* (2006.01)
*A61B 5/027* (2006.01)
*A61B 17/06* (2006.01)
*A61B 17/22* (2006.01)
*A61M 25/10* (2013.01)

(52) U.S. Cl.
CPC  *A61B 2017/0474* (2013.01); *A61B 2017/0477* (2013.01); *A61B 2017/0496* (2013.01); *A61B 2017/06042* (2013.01); *A61B 2017/22038* (2013.01); *A61B 2017/22067* (2013.01); *A61M 25/10* (2013.01); *A61M 2025/1052* (2013.01)

(56) References Cited

U.S. PATENT DOCUMENTS

| | | |
|---|---|---|
| 5,007,921 A | 4/1991 | Brown |
| 5,026,390 A | 6/1991 | Brown |
| 5,163,906 A | 11/1992 | Ahmadi |
| 5,250,060 A | 10/1993 | Carbo et al. |
| 5,304,184 A | 4/1994 | Hathaway et al. |
| 5,306,250 A | 4/1994 | March et al. |
| 5,312,356 A | 5/1994 | Engelson et al. |
| 5,324,262 A | 6/1994 | Fischell et al. |
| 5,328,470 A | 7/1994 | Nabel et al. |
| 5,328,471 A | 7/1994 | Slepian |
| 5,380,284 A | 1/1995 | Don Michael |
| 5,389,090 A | 2/1995 | Fischell et al. |
| 5,403,328 A | 4/1995 | Shallman |
| 5,417,699 A | 5/1995 | Klein et al. |
| 5,443,454 A | 8/1995 | Tanabe et al. |
| 5,476,450 A | 12/1995 | Ruggio |
| 5,476,469 A | 12/1995 | Hathaway et al. |
| 5,496,294 A | 3/1996 | Hergenrother et al. |
| 5,520,702 A | 5/1996 | Sauer et al. |
| 5,527,322 A | 6/1996 | Klein et al. |
| 5,549,633 A | 8/1996 | Evans et al. |
| 5,584,803 A | 12/1996 | Stevens et al. |
| 5,613,974 A | 3/1997 | Andreas et al. |
| 5,643,289 A | 7/1997 | Sauer et al. |
| 5,643,292 A | 7/1997 | Hart |
| 5,649,959 A | 7/1997 | Hannam et al. |
| 5,669,917 A | 9/1997 | Sauer et al. |
| 5,674,231 A | 10/1997 | Green et al. |
| 5,720,757 A | 2/1998 | Hathaway et al. |
| 5,730,734 A | 3/1998 | Adams et al. |
| 5,746,755 A | 5/1998 | Wood et al. |
| 5,766,183 A | 6/1998 | Sauer |
| 5,769,830 A | 6/1998 | Parker |
| 5,779,719 A | 7/1998 | Klein et al. |
| 5,782,800 A | 7/1998 | Yoon |
| 5,792,152 A | 8/1998 | Klein et al. |
| 5,797,929 A | 8/1998 | Andreas et al. |
| 5,810,846 A | 9/1998 | Virnich et al. |
| 5,810,850 A | 9/1998 | Hathaway et al. |
| 5,833,650 A | 11/1998 | Imran |
| 5,846,253 A | 12/1998 | Buelna et al. |
| 5,855,585 A | 1/1999 | Kontos |
| 5,860,990 A | 1/1999 | Nobles et al. |
| 5,860,991 A | 1/1999 | Klein et al. |
| 5,902,311 A | 5/1999 | Andreas et al. |
| 5,916,193 A | 6/1999 | Stevens et al. |
| 5,921,994 A | 7/1999 | Andreas et al. |
| 6,004,310 A | 12/1999 | Bardsley et al. |
| 6,004,341 A | 12/1999 | Zhu et al. |
| 6,024,747 A | 2/2000 | Kontos |
| 6,030,369 A | 2/2000 | Engelson et al. |
| 6,030,395 A | 2/2000 | Nash et al. |
| 6,036,699 A | 3/2000 | Andreas et al. |
| 6,042,601 A | 3/2000 | Smith |
| 6,077,279 A | 6/2000 | Kontos |
| 6,110,185 A | 8/2000 | Barra et al. |
| 6,117,144 A | 9/2000 | Nobles et al. |
| 6,117,145 A | 9/2000 | Wood et al. |
| 6,132,440 A | 10/2000 | Hathaway et al. |
| 6,136,010 A | 10/2000 | Modesitt et al. |
| 6,146,370 A | 11/2000 | Barbut |
| 6,146,373 A | 11/2000 | Cragg et al. |
| 6,190,396 B1 | 2/2001 | Whitin et al. |
| 6,197,042 B1 | 3/2001 | Ginn et al. |
| 6,206,868 B1 | 3/2001 | Parodi |
| 6,206,893 B1 | 3/2001 | Klein et al. |
| 6,245,079 B1 | 6/2001 | Nobles et al. |
| 6,277,140 B2 | 8/2001 | Ginn et al. |
| 6,295,989 B1 | 10/2001 | Connors, III |
| 6,302,898 B1 | 10/2001 | Edwards et al. |
| 6,306,163 B1 | 10/2001 | Fitz |
| 6,348,059 B1 | 2/2002 | Hathaway et al. |
| 6,355,050 B1 | 3/2002 | Andreas et al. |
| 6,358,258 B1 | 3/2002 | Arcia et al. |
| 6,364,900 B1 | 4/2002 | Heuser |
| 6,368,334 B1 | 4/2002 | Sauer |
| 6,379,325 B1 | 4/2002 | Benett et al. |
| 6,391,048 B1 | 5/2002 | Ginn et al. |
| 6,413,235 B1 | 7/2002 | Parodi |
| 6,423,032 B2 | 7/2002 | Parodi |
| 6,423,086 B1 | 7/2002 | Barbut et al. |
| 6,428,549 B1 | 8/2002 | Kontos |
| 6,435,189 B1 | 8/2002 | Lewis et al. |
| 6,436,109 B1 | 8/2002 | Kontos |
| 6,454,741 B1 | 9/2002 | Muni et al. |
| 6,461,364 B1 | 10/2002 | Ginn et al. |
| 6,482,172 B1 | 11/2002 | Thramann |
| 6,517,553 B2 | 2/2003 | Klein et al. |
| 6,533,800 B1 | 3/2003 | Barbut |
| 6,540,712 B1 | 4/2003 | Parodi et al. |
| 6,551,331 B2 | 4/2003 | Nobles et al. |
| 6,558,399 B1 | 5/2003 | Isbell et al. |
| 6,562,052 B2 | 5/2003 | Nobles et al. |
| 6,569,182 B1 | 5/2003 | Balceta et al. |
| 6,582,448 B1 | 6/2003 | Boyle et al. |
| 6,589,214 B2 | 7/2003 | McGuckin, Jr. et al. |
| 6,595,953 B1 | 7/2003 | Coppi et al. |
| 6,596,003 B1 | 7/2003 | Realyvasquez, Jr. et al. |
| 6,623,471 B1 | 9/2003 | Barbut |
| 6,623,510 B2 | 9/2003 | Carley et al. |
| 6,626,886 B1 | 9/2003 | Barbut |
| 6,626,918 B1 | 9/2003 | Ginn et al. |
| 6,632,238 B2 | 10/2003 | Ginn et al. |
| 6,641,592 B1 | 11/2003 | Sauer et al. |
| 6,645,222 B1 | 11/2003 | Parodi et al. |
| 6,652,480 B1 | 11/2003 | Imran et al. |
| 6,663,650 B2 | 12/2003 | Sepetka et al. |
| 6,673,040 B1 | 1/2004 | Samson et al. |
| 6,679,893 B1 | 1/2004 | Tran |
| 6,682,505 B2 | 1/2004 | Bates et al. |
| 6,695,867 B2 | 2/2004 | Ginn et al. |
| 6,719,717 B1 | 4/2004 | Johnson et al. |
| 6,719,777 B2 | 4/2004 | Ginn et al. |
| 6,730,102 B1 | 5/2004 | Burdulis, Jr. et al. |
| 6,746,457 B2 | 6/2004 | Dana et al. |
| 6,749,621 B2 | 6/2004 | Pantages et al. |
| 6,790,197 B2 | 9/2004 | Kosinski et al. |
| 6,837,881 B1 | 1/2005 | Barbut |
| 6,840,949 B2 | 1/2005 | Barbut |
| 6,847,234 B2 | 1/2005 | Choi |
| 6,855,136 B2 | 2/2005 | Dorros et al. |
| 6,884,235 B2 | 4/2005 | McGuckin, Jr. et al. |
| 6,902,540 B2 | 6/2005 | Dorros et al. |
| 6,905,490 B2 | 6/2005 | Parodi |
| 6,908,474 B2 | 6/2005 | Hogendijk et al. |
| 6,932,824 B1 | 8/2005 | Roop et al. |

(56) References Cited

U.S. PATENT DOCUMENTS

| | | |
|---|---|---|
| 6,936,060 B2 | 8/2005 | Hogendijk et al. |
| 6,942,674 B2 | 9/2005 | Belef et al. |
| 6,958,059 B2 | 10/2005 | Zadno-Azizi |
| 6,964,668 B2 | 11/2005 | Modesitt et al. |
| 7,001,398 B2 | 2/2006 | Carley et al. |
| 7,001,400 B1 | 2/2006 | Modesitt et al. |
| 7,004,924 B1 | 2/2006 | Brugger et al. |
| 7,004,931 B2 | 2/2006 | Hogendijk |
| 7,004,952 B2 | 2/2006 | Nobles et al. |
| 7,029,480 B2 | 4/2006 | Klein et al. |
| 7,029,487 B2 | 4/2006 | Greene, Jr. et al. |
| 7,033,344 B2 | 4/2006 | Imran |
| 7,048,747 B2 | 5/2006 | Arcia et al. |
| 7,048,758 B2 | 5/2006 | Boyle et al. |
| 7,063,714 B2 | 6/2006 | Dorros et al. |
| 7,083,594 B2 | 8/2006 | Coppi |
| 7,090,686 B2 | 8/2006 | Nobles et al. |
| 7,094,246 B2 | 8/2006 | Anderson et al. |
| 7,144,411 B2 | 12/2006 | Ginn et al. |
| 7,208,008 B2 | 4/2007 | Clarke |
| 7,232,452 B2 | 6/2007 | Adams et al. |
| 7,367,982 B2 | 5/2008 | Nash et al. |
| 7,374,561 B2 | 5/2008 | Barbut |
| 7,390,328 B2 | 6/2008 | Modesitt |
| 7,396,359 B1 | 7/2008 | Derowe et al. |
| 7,422,579 B2 | 9/2008 | Wahr et al. |
| 7,458,980 B2 | 12/2008 | Barbut |
| 8,157,760 B2 | 4/2012 | Criado et al. |
| 2001/0034509 A1 | 10/2001 | Cragg et al. |
| 2001/0044598 A1 | 11/2001 | Parodi |
| 2001/0044634 A1 | 11/2001 | Don Michael et al. |
| 2001/0044638 A1 | 11/2001 | Levinson et al. |
| 2001/0049486 A1 | 12/2001 | Evans et al. |
| 2002/0072706 A1 | 6/2002 | Hiblar et al. |
| 2002/0077600 A1 | 6/2002 | Sirimanne |
| 2002/0087119 A1 | 7/2002 | Parodi |
| 2002/0156455 A1 | 10/2002 | Barbut |
| 2002/0165598 A1 | 11/2002 | Wahr et al. |
| 2002/0173815 A1 | 11/2002 | Hogendijk et al. |
| 2003/0004543 A1 | 1/2003 | Gleeson et al. |
| 2003/0032936 A1 | 2/2003 | Lederman |
| 2003/0036755 A1 | 2/2003 | Ginn |
| 2003/0093093 A1 | 5/2003 | Modesitt et al. |
| 2004/0092966 A1 | 5/2004 | Nobles et al. |
| 2004/0093003 A1 | 5/2004 | MacKenzie et al. |
| 2004/0210251 A1 | 10/2004 | Kontos |
| 2004/0260333 A1 | 12/2004 | Dubrul et al. |
| 2005/0131453 A1 | 6/2005 | Parodi |
| 2005/0149065 A1 | 7/2005 | Modesitt |
| 2005/0154344 A1 | 7/2005 | Chang |
| 2005/0154349 A1 | 7/2005 | Renz et al. |
| 2005/0251162 A1 | 11/2005 | Rothe et al. |
| 2005/0267520 A1 | 12/2005 | Modesitt |
| 2006/0064124 A1 | 3/2006 | Zhu et al. |
| 2006/0111741 A1 | 5/2006 | Nardella |
| 2006/0167476 A1 | 7/2006 | Burdulis et al. |
| 2006/0200191 A1 | 9/2006 | Zadno-Azizi |
| 2006/0282088 A1 | 12/2006 | Ryan |
| 2006/0287673 A1 | 12/2006 | Brett et al. |
| 2007/0078430 A1 | 4/2007 | Adams |
| 2007/0198049 A1 | 8/2007 | Barbut |
| 2007/0270888 A1 | 11/2007 | Barrientos |
| 2008/0004636 A1 | 1/2008 | Walberg et al. |
| 2008/0045979 A1 | 2/2008 | Ma |
| 2008/0058839 A1 | 3/2008 | Nobles et al. |
| 2008/0086164 A1 | 4/2008 | Rowe |
| 2008/0097479 A1 | 4/2008 | Boehlke et al. |
| 2008/0140010 A1 | 6/2008 | Kennedy et al. |
| 2008/0188890 A1 | 8/2008 | Weitzner et al. |
| 2008/0221614 A1 | 9/2008 | Mas |
| 2008/0287967 A1 | 11/2008 | Andreas et al. |
| 2008/0312666 A1 | 12/2008 | Ellingwood et al. |
| 2009/0018455 A1 | 1/2009 | Chang |
| 2009/0024072 A1 | 1/2009 | Criado et al. |
| 2009/0143789 A1 | 6/2009 | Houser |
| 2009/0198172 A1 | 8/2009 | Garrison et al. |
| 2009/0254166 A1 | 10/2009 | Chou et al. |
| 2010/0042118 A1 | 2/2010 | Garrison et al. |
| 2010/0114002 A1 | 5/2010 | O'Mahony et al. |
| 2010/0185216 A1 | 7/2010 | Garrison et al. |
| 2010/0280431 A1 | 11/2010 | Criado et al. |
| 2011/0034986 A1 | 2/2011 | Chou et al. |
| 2011/0166496 A1 | 7/2011 | Criado et al. |
| 2011/0166497 A1 | 7/2011 | Criado et al. |

FOREIGN PATENT DOCUMENTS

| | | |
|---|---|---|
| JP | 02-237574 | 9/1990 |
| JP | H07-265412 A | 10/1995 |
| JP | H08-071161 A | 3/1996 |
| JP | 10-43192 A | 2/1998 |
| JP | 10-052490 A | 2/1998 |
| JP | H10-033666 A | 2/1998 |
| JP | 11-42233 A | 2/1999 |
| JP | 2001-517472 A | 10/2001 |
| JP | 2001-523492 A | 11/2001 |
| JP | 2002-518086 A | 6/2002 |
| JP | 2002-522149 A | 7/2002 |
| JP | 2002-543914 A | 12/2002 |
| JP | 2003-516178 A | 5/2003 |
| JP | 2003-521286 A | 7/2003 |
| JP | 2003-521299 A | 7/2003 |
| JP | 2003-310625 A | 11/2003 |
| JP | 2005-536284 | 12/2005 |
| JP | 2006-500095 A | 1/2006 |
| JP | 2007-500577 A | 1/2007 |
| JP | 2007-244902 A | 9/2007 |
| JP | 2007-301326 A | 11/2007 |
| WO | WO-99/15085 A1 | 4/1999 |
| WO | WO-99/25419 A | 5/1999 |
| WO | WO-99/65420 A1 | 12/1999 |
| WO | WO-00/09028 A1 | 2/2000 |
| WO | WO-00/56223 A1 | 9/2000 |
| WO | WO-00/69350 A1 | 11/2000 |
| WO | WO-00/76390 A2 | 12/2000 |
| WO | WO-01/34061 A1 | 5/2001 |
| WO | WO-01/54588 A1 | 8/2001 |
| WO | WO-02/096295 A1 | 12/2002 |
| WO | WO-03/071955 A2 | 9/2003 |
| WO | WO-03/090628 A1 | 11/2003 |
| WO | WO-2004/017865 A1 | 3/2004 |
| WO | WO-2004/026144 A1 | 4/2004 |
| WO | WO-2004/060169 A2 | 7/2004 |
| WO | WO-2004/110303 A2 | 12/2004 |
| WO | WO-2005/051206 A1 | 6/2005 |
| WO | WO-2006/128017 A2 | 11/2006 |
| WO | WO-2009/012473 A3 | 1/2009 |
| WO | WO-2009/099764 A1 | 8/2009 |
| WO | WO-2009/100210 A1 | 8/2009 |
| WO | WO-2010/019719 A2 | 2/2010 |

OTHER PUBLICATIONS

Bettmann, M. et al, "Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association". Circulation Journal of the American Heart Association. 1998. 97:121-123. Retrieved Feb. 16, 2012.

Bhatt, D. L., R. E. Raymond, et al. (2002). "Successful "pre-closure" of 7Fr and 8Fr femoral arteriotomies with a 6Fr suture-based device (the Multicenter Interventional Closer Registry)." Am J Cardiol 89(6): 777-9.

Blanc, R., C. Mounayer, et al. (2002). "Hemostatic closure device after carotid puncture for stent and coil placement in an intracranial aneurysm: technical note." AJNR Am J Neuroradiol 23(6): 978-81.

Blanc, R., M. Piotin, et al. (2006). "Direct cervical arterial access for intracranial endovascular treatment." Neuroradiology 48(12): 925-9.

Chang, M.D., et al, "A new approach to carotid angioplasty and stenting with transcervical occlusion and protective shunting: Why it may be a better carotid artery intervention" (J Vasc Surg 2004; 39:994-1002.).

(56) References Cited

OTHER PUBLICATIONS

Criado, F.J., et al., Access strategies for carotid artery intervention. J Invasive Cardiol, 2000. 12(1): p. 61-8.

Criado, M.D, et al. "Transcervical Carotid Artery Angioplasty and Stenting with Carotid Flow Reversal: Surgical Technique" Ann Vasc Surg 2004; 18: 257-261.

Criado, M.D., et al. "Transcervical carotid stenting with internal carotid artery flow reversal: Feasibility and preliminary results" (J Vasc Surg 2004; 40: 476-83).

Criado, M.D., et al. (2004) "Carotid angioplasty with internal carotid artery flow reversal is well tolerated in the awake patient" Journal of Vascular Surgery, 40(1):92-7.

Henry et al. (1999) "Carotid stenting with cerebral protection: First clinical experience using the PercuSurge Guard Wire System" *J. Endovasc. Surg.* 6:321-331.

Hoffer et al. "Percutaneous Arterial Closure Devices" J. Vasc. Interv. Radiol. 14:865-885 (2003).

Howell, M., K. Doughtery, et al. (2002). "Percutaneous repair of abdominal aortic aneurysms using the AneuRx stent graft and the percutaneous vascular surgery device." Catheter Cardiovasc Interv 55(3): 281-7.

Massiere, B., A. von Ristow, et al. (2009). "Closure of Carotid Artery Puncture Site With a Percutaneous Device." Ann Vasc Surg. 23(2): 256 e5-7.

Ribo et al. (2006). "Transcranial doppler monitoring of transcervical carotid stenting with flow reversal protection: a novel carotid revascularization technique" 27:2846-2849 (originally published online Sep. 28, 2006).

Ruiz et al., "Feasibility of patent foramen ovale closure with no-device left behind: first-in-man percutaneous suture closure" Catheterization and Cardiovascular interventions 71:921-926 (2008).

Stejskal, et al., "Experience of 500 Cases of Neurophysiological Monitoring in Carotid Endarterectomy", Acta Neurochir, 2007, 149:681-689.

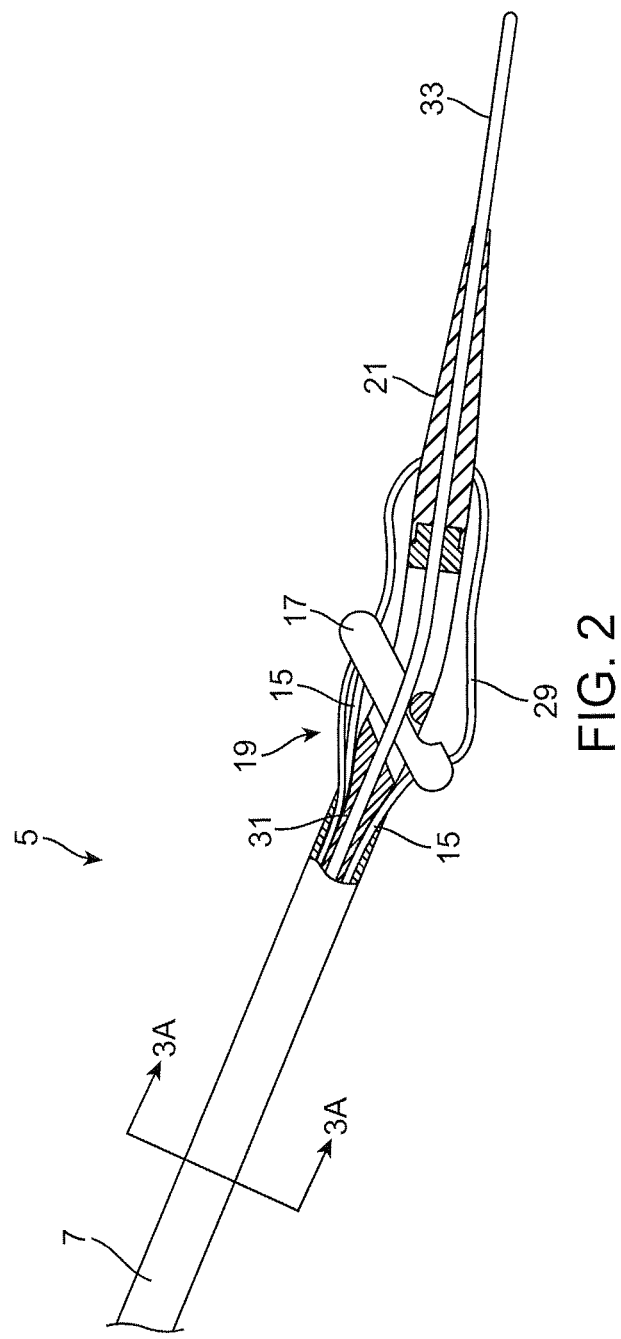

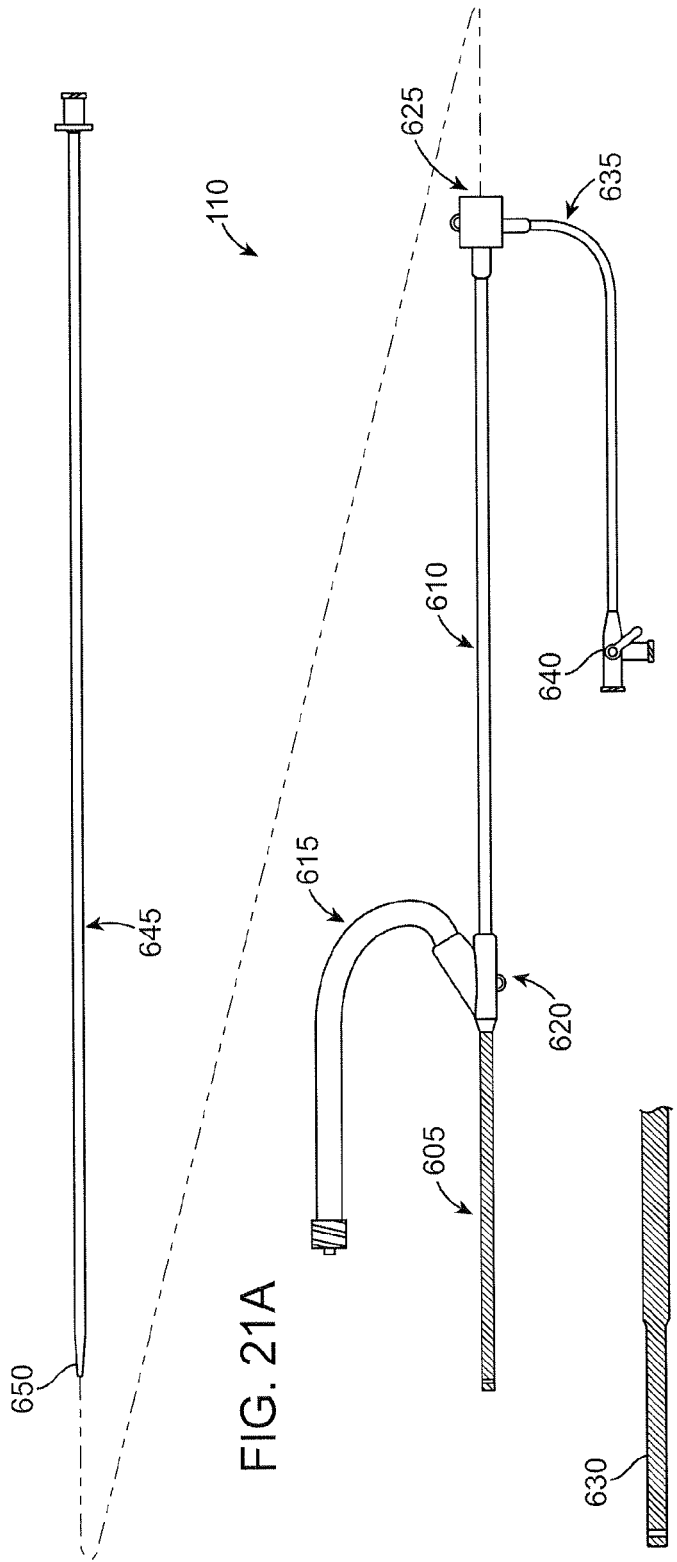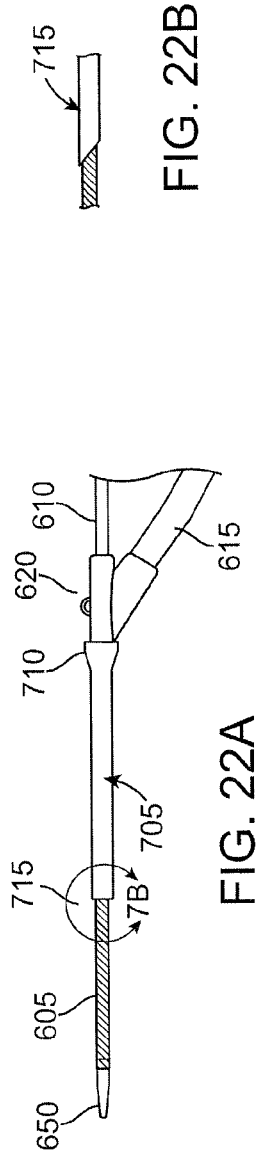

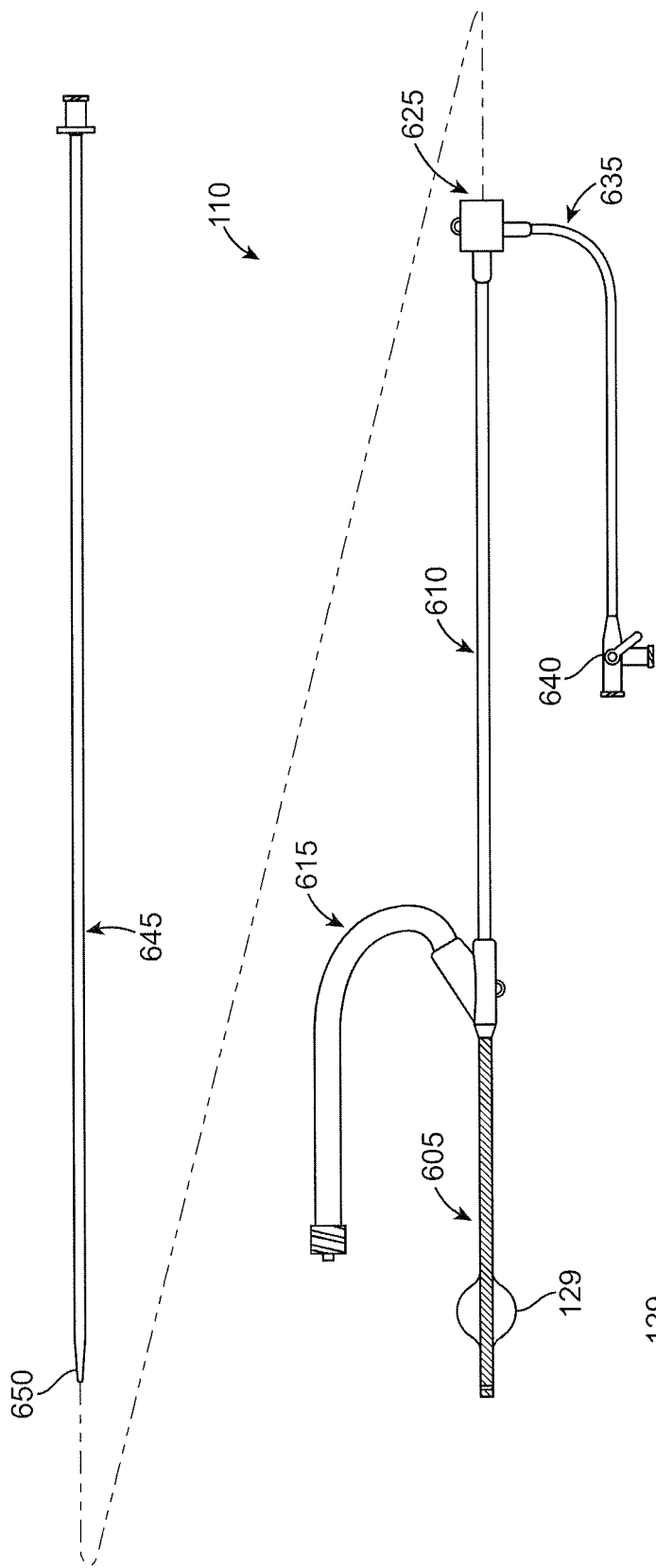
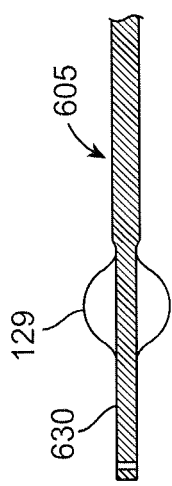
FIG. 23B
FIG. 23A

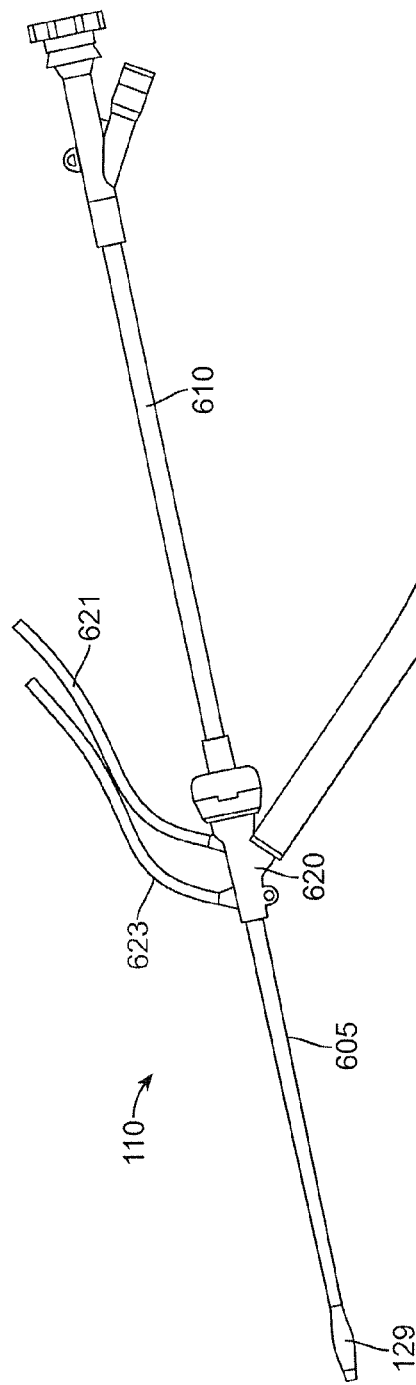
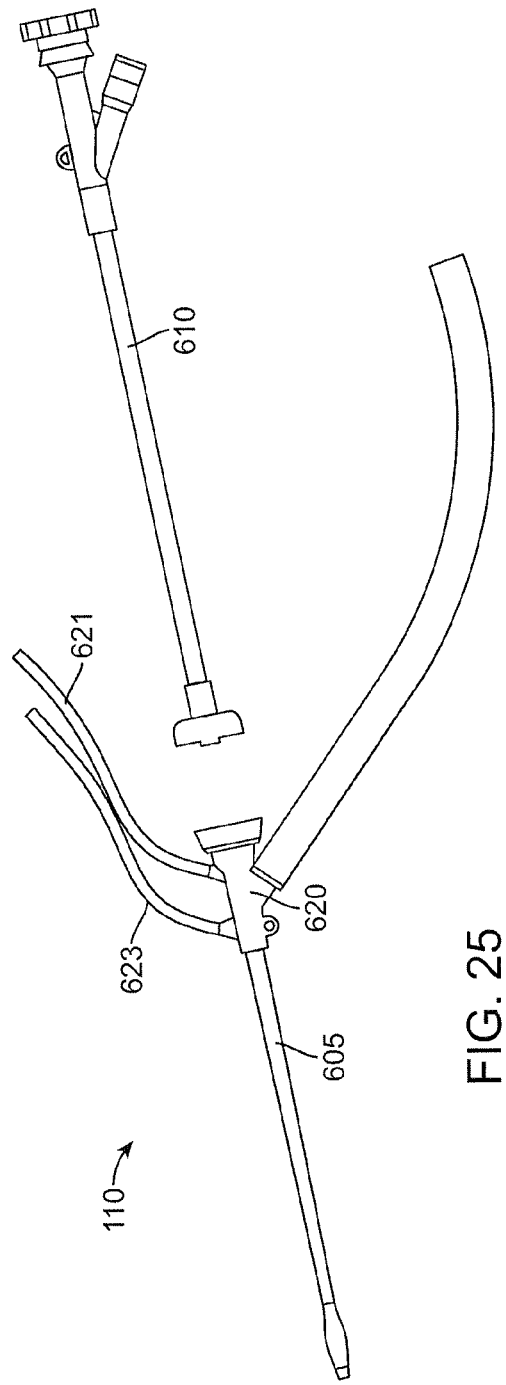
FIG. 24
FIG. 25

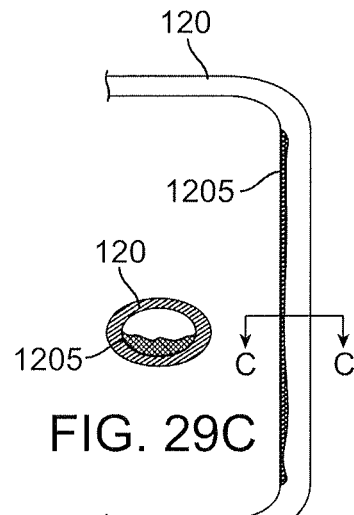
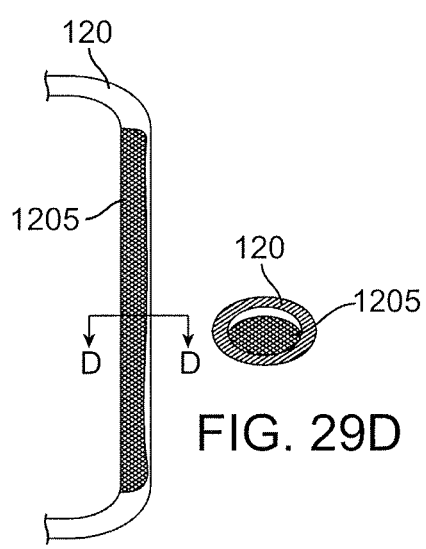
FIG. 29C   FIG. 29D
FIG. 29A   FIG. 29B
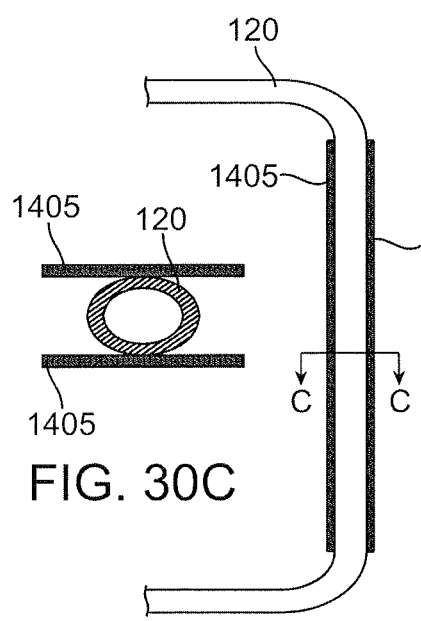
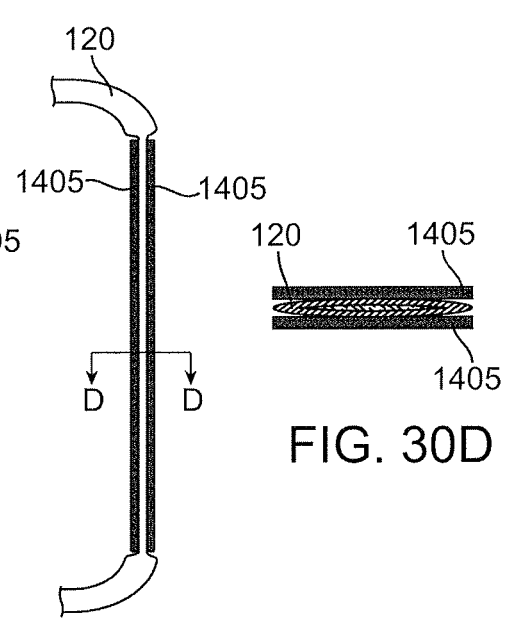
FIG. 30C   FIG. 30D
FIG. 30A   FIG. 30B

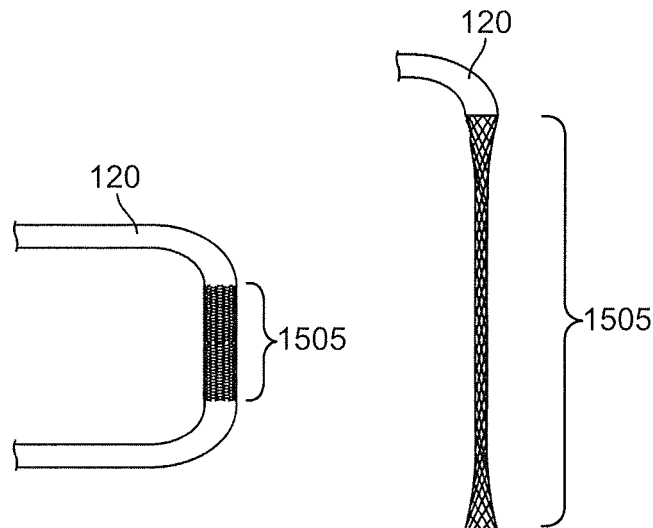
FIG. 31A
FIG. 31B
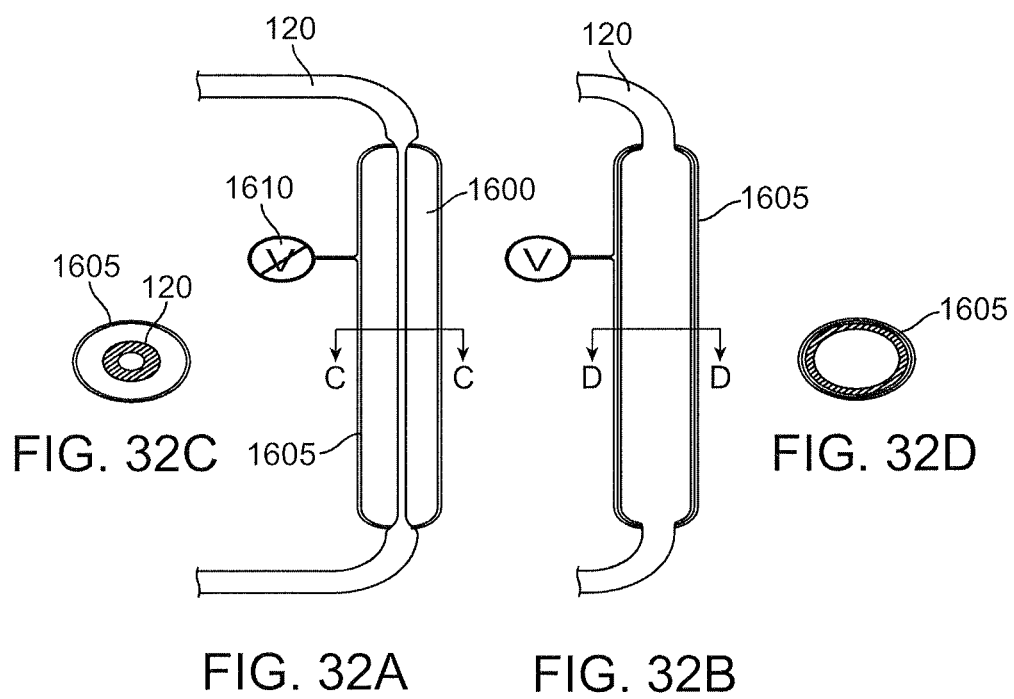
FIG. 32C
FIG. 32A
FIG. 32B
FIG. 32D

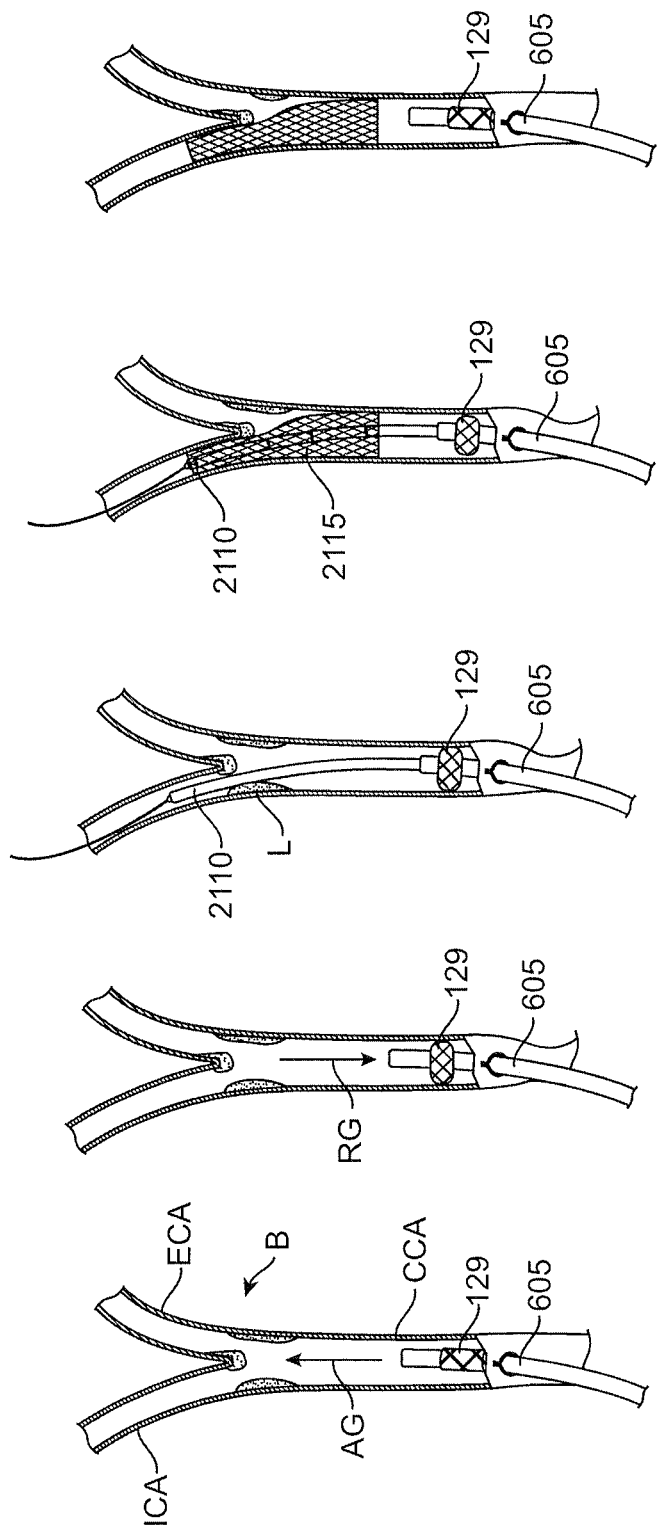

SUTURE DELIVERY DEVICE

CROSS-REFERENCES TO PRIORITY DOCUMENTS

This application is a continuation of co-pending U.S. patent application Ser. No. 12/633,730, entitled "SUTURE DELIVERY DEVICE," filed Dec. 8, 2009; which in turn is a continuation-in-part of U.S. patent application Ser. No. 12/540,341, entitled "SUTURE DELIVERY DEVICE," filed Aug. 21, 2009, which claims priority of Provisional Application Ser. No. 61/088,680, filed on Aug. 13, 2008, Provisional Application Ser. No. 61/097,812, filed on Sep. 17, 2008, Provisional Application Ser. No. 61/138,403, filed on Dec. 17, 2008, Provisional Application Ser. No. 61/162,173, filed on Mar. 20, 2009, and Provisional Application Ser. No. 61/165,392, filed on Mar. 31, 2009. Priority of the aforementioned filing dates is hereby claimed and the disclosures of the patent applications are hereby incorporated by reference in their entirety.

BACKGROUND

The present disclosure relates generally to medical methods and devices. More particularly, the present disclosure relates to methods and devices for suture "pre-closing" a vessel, in other words, deploying closure sutures for puncture wounds into blood vessels wherein the sutures are applied before the vessel is accessed with a sheath or cannula.

Medical procedures for gaining intravascular arterial access are well-established, and fall into two broad categories: surgical cut-down and percutaneous access. In a surgical cut-down, a skin incision is made and tissue is dissected away to the level of the target artery. Depending on the size of the artery and of the access device, an incision is made into the vessel with a blade, or the vessel is punctured directly by the access device. In some instances, a micro-puncture technique is used whereby the vessel is initially accessed by a small gauge needle, and successively dilated up to the size of the access device. For percutaneous access, a puncture is made from the skin, through the subcutaneous tissue layers to the vessel, and into the vessel itself. Again, depending on the size of the artery and of the access device, the procedure will vary, for example a Seldinger technique, modified Seldinger technique, or micro-puncture technique is used.

Because arteries are high-pressure vessels, additional maneuvers may be required to achieve hemostasis after removal of the access device from the vessel. In the case of surgical cut-down, a suture may be used to close the arteriotomy. For percutaneous procedures, either manual compression or a closure device may be used. While manual compression remains the gold standard with high reliability and low cost, closure devices require less physician time and lower patient recovery time. In addition, closure devices are often required for procedures with larger access devices and/or for patients with anti-coagulation and anti-platelet therapy. Examples of closure devices include suture-based closure devices such as the Abbott Vascular PERCLOSE or ProStar family of devices or the Sutura SUPERSTITCH device. Other closure devices include clip closure devices such as the Abbott Vascular STARCLOSE device, or "plug" closure devices such as the Kensey Nash/St. Jude Medical ANGIO-SEAL device.

In certain types of procedures, it is advantageous to "pre-close" the arteriotomy, for example if the arteriotomy is significant in size, if the arteriotomy site is difficult to access, or if there is a heightened risk of inadvertent sheath removal. The term "suture pre-close" refers to deploying closure sutures for puncture wounds into blood vessels wherein the sutures are applied before the vessel is accessed with the procedural sheath or cannula. The ability to gain rapid hemostatic control of the access site can be critical. In an open surgical procedure, a suture is sometimes placed into the vessel wall in a U-stitch, Z-stitch, or purse-string pattern prior to vessel access. The arteriotomy is made through the center of this stitch pattern. The suture may be tensioned around the sheath during the procedure, or the suture may be left loose. Generally, the two ends of the suture exit the incision and are anchored during the procedure, for example with hemostatic forceps. If the sheath is inadvertently removed from the arteriotomy, rapid hemostasis may be achieved by applying tension to the ends of the suture. After removal of the sheath from the arteriotomy, the suture is then tied off to achieve permanent hemostasis.

In percutaneous procedures, it is not possible to insert a closing suture in the manner described above. In these procedures, if suture pre-close is desired, a percutaneous suture-based vessel closure device would need to be used. However, current percutaneous suture-based vessel closure devices require previous dilatation (widening) of the initial needle puncture to be inserted into the vessel, and are designed to be placed after the procedural sheath has been inserted into, and in some cases removed from the arteriotomy. In this manner, the dilatation has been accomplished by the procedural sheath and dilator itself. In view of this, current suture-based vessel closure devices have certain limitations for use in pre-closure of an arteriotomy. To accomplish pre-closure with these devices, a dilator or dilator/sheath combination needs to be initially inserted into the vessel over a guidewire to dilate the arteriotomy puncture, and then exchanged for the closure device, with the difficulty of maintaining hemostasis during this exchange.

Another limitation is that once the suture is placed in the vessel with the suture-based vessel closure devices, it is likewise difficult to maintain hemostasis during removal of the suture-based vessel closure device and insertion of the procedural sheath. Similarly, once the procedural sheath is removed, it is difficult to maintain hemostasis before the final suture knot is tied. Or, if the suture is pre tied, it is difficult to maintain hemostasis before knot is pushed into place. In addition, current suture-based vessel closure devices do not have any means to gain rapid access to the suture ends to apply tension in the instance of inadvertent sheath removal.

Certain procedures, for example intervention of the carotid arteries, offer additional clinical challenges. In a transcervical approach to treatment of the internal carotid artery and/or the carotid artery bifurcation, the distance from the access site to the treatment site is usually less than 5-7 cm. Therefore it is desirable to limit the length of the pre-closure device or any associated accessories (needle puncture, guidewire, micro introducer, dilator, or sheath itself) to 3-4 cm, to remove risk of incursion into the plaque zone and reduce the risk of generating embolic particles. In the case of the Abbott ProStar or Perclose, the vessel entry device requires about a 15 cm length into the vessel. With other devices, there are no methods or features for limiting or controlling the amount of egress of these device components in the vessel. In addition, the consequences of failure of the closure devices to achieve complete hemostasis are great. If the suture closure did not achieve full hemostasis, the resultant hematoma may lead to loss of airway passage and/or critical loss of blood to the brain, both of which lead to severe patient compromise and possibly death.

SUMMARY

Disclosed is a suture-based vessel closure device that can perform the dilation of an arteriotomy puncture, and therefore does not require previous dilation of the arteriotomy puncture by a separate device or by a procedural sheath dilator. The suture-based vessel closure device can place one or more sutures across the vessel access site such that, when the suture ends are tied off after sheath removal, the stitch or stitches provide hemostasis to the access site. The sutures can be applied either prior to insertion of a procedural sheath through the arteriotomy or after removal of the sheath from the arteriotomy. The device can maintain temporary hemostasis of the arteriotomy after placement of sutures but before and during placement of the procedural sheath, and can also maintain temporary hemostasis after withdrawal of the procedural sheath but before tying off the suture. A suture-based vessel closure device also desirably can provide rapid access and control of suture ends in the instance of inadvertent sheath removal as well as provide a highly reliable hemostatic closure of the access site.

In one aspect, there is disclosed a device for closing an aperture in a wall of a blood vessel, the device comprising: a body; at least one suture element held within the body; and at least one suture capture rod within the body, the suture capture rod being operatively associated with the suture element and arranged to pass the suture element through the vessel wall such that opposed portions of the suture element extend from the vessel wall; wherein a distal tip of the body acts as a dilator that dilates the aperture in the wall of the vessel.

In another aspect, there is disclosed a device for closing an aperture in a wall of a blood vessel, the device comprising: a body; at least one suture element held within the body; at least one suture capture rod within the body, the suture capture rod being operatively associated with the suture element and arranged to pass the suture element through the vessel wall such that the opposed portions of the suture element extend from the vessel wall and the suture element defines a knot between opposed portions thereof after the suture element has been passed through the vessel wall; and a sheath positioned on a proximal end of the body, wherein the sheath slides distally over the body in a manner that permits the sheath to be positioned through the aperture in the wall of the blood vessel In another aspect, there is disclosed a device for use in accessing an artery, comprising: a distal sheath having a distal end adapted to be introduced into the artery, a proximal end, and a lumen extending between the distal and proximal ends; a Y-arm connection to a flow line having a lumen, said Y arm and flow line lumens connected to the sheath so that blood flowing into the distal end of the sheath can flow through the Y-arm and into the lumen of the flow line; a proximal extension having a distal end, a proximal end, and a lumen therebetween, wherein the distal end of the proximal extension is removably connected to the proximal end of the sheath at a junction so that the lumens of each are contiguous; and a hemostasis valve at the proximal end of the proximal extension.

In another aspect, there is disclosed a system of devices for closing an aperture in a wall of a blood vessel, the system comprising: a suture placement device with a guidewire lumen; a guidewire positioned in the guidewire lumen; and a first expandable element on the guidewire, the expandable element configured to maintain hemostasis of the aperture in the wall of the blood vessel In another aspect, there is disclosed a system of devices for closing an aperture in a wall of a blood vessel, the system comprising: a suture placement device with a guidewire lumen; a guidewire positioned in the guidewire lumen; and an expandable anchor on the guidewire configured to interact with the blood vessel to maintain a fixed position of the guidewire relative to the blood vessel.

In another aspect, there is disclosed a system of devices for closing an aperture in a wall of a blood vessel, the system comprising: a suture placement device with a guidewire lumen; a guidewire positioned in the guidewire lumen; and at least one clip that removably secures the guidewire or suture to the patient In another aspect, there is disclosed a device for closing an aperture in a wall of a blood vessel, the device comprising: a body; at least one suture element held within the body; at least one suture capture rod within the body, the suture capture rod being operatively associated with the suture element and arranged to pass the suture element through the vessel wall such that the opposed portions of the suture element extend from the vessel wall and the suture element defines a knot between opposed portions thereof after the suture element has been passed through the vessel wall; a seal element movably positioned over the body; and a pusher that pushes the seal element toward the aperture in the wall of the blood vessel to cause the seal to maintain hemostasis.

In another aspect, there is disclosed a method of applying a closing suture to an artery, comprising: inserting a suture delivery device into the artery such that a distal tip of the suture delivery device dilates an opening of an arteriotomy into the artery; drawing at least one end of a suture outside the body of the patient using the suture closure device such that the suture can be held until such time as the suture is to be tied off to create a permanent closure of the arteriotomy; and removing the suture delivery device.

In another aspect, there is disclosed a method of applying a closing suture to an artery, comprising: inserting a suture delivery device into the artery; drawing at least one end of a suture outside the body of the patient using the suture delivery device such that the suture can be held until such time as the suture is to be tied off to create a permanent closure of the arteriotomy; separating the suture from the body of the suture delivery device; advancing a pre-mounted sheath over the suture delivery body and into the artery; and removing the suture delivery device.

In another aspect, there is disclosed a method of applying a closing suture to an artery prior to inserting a procedural sheath, comprising: inserting a suture delivery device over a guidewire into the artery; drawing at least one end of a suture outside the body of the patient using the suture closure device such that the suture can be held until such time as the suture is to be tied off to create a permanent closure of the arteriotomy; removing the suture delivery device while leaving the guidewire in place; and inserting a procedural sheath over the guidewire into the artery.

In another aspect, there is disclosed a method of exchanging a suture placement device for another vessel closure device, comprising: inserting a suture delivery device over a guidewire into the artery; expanding a sealing element on the guidewire to maintain hemostasis of the artery; and removing the suture delivery device and inserting another vessel closure device over the guidewire.

In another aspect, there is disclosed a method of exchanging a suture placement device for another vessel closure device, comprising: inserting a suture delivery device over a guidewire into the artery; expanding an anchor element on the guidewire to maintain the guidewire position relative to the artery; and removing the suture delivery device and inserting another vessel closure device over the guidewire.

In another aspect, there is disclosed a method of performing a procedure on a vascular or cardiac structure, comprising: inserting a guidewire into the common carotid artery through a puncture in the wall of the common carotid artery; inserting a suture delivery device over the guidewire into the common carotid artery such that a distal tip of the suture delivery device dilates an opening of an arteriotomy into the artery; drawing at least one end of a suture outside the body of the patient using the suture closure device such that the suture can be held until such time as the suture is to be tied off to create a permanent closure of the arteriotomy; removing the suture delivery device while leaving the guidewire in place; inserting a procedural sheath over the guidewire into the common carotid artery; inserting a therapeutic device or devices through the sheath to the treatment site, performing a therapeutic procedure, and removing the therapeutic device or devices from the sheath; removing the sheath; and tying off the ends of the suture to close the arterial access site In another aspect, there is disclosed a method of performing a procedure on a vascular or cardiac structure, comprising: inserting a suture delivery device with a premounted sheath into the common carotid artery through an arteriotomy in the wall of the common carotid artery; drawing at least one end of a suture outside the body of the patient using the suture delivery device such that the suture can be held until such time as the suture is to be tied off to create a permanent closure of the arteriotomy; separating the suture from the body of the suture delivery device; advancing the premounted sheath through the arteriotomy into the common carotid artery; removing the suture delivery device; inserting a therapeutic device or devices through the sheath to the treatment site, performing a therapeutic procedure, and removing the therapeutic device or devices from the sheath; removing the sheath; and tying off the ends of the suture to close the arterial access site.

In another aspect, there is disclosed a method of performing a procedure on a vascular or cardiac structure, comprising: inserting a procedural sheath into the common carotid artery through an arteriotomy in the wall of the common carotid artery; inserting a therapeutic device or devices through the sheath to the treatment site, performing a therapeutic procedure, and removing the therapeutic device or devices from the sheath; inserting a suture delivery device into the common carotid artery through the arteriotomy; drawing at least one end of a suture outside the body of the patient using the suture delivery device such that the suture can be held until such time as the suture is to be tied off to create a permanent closure of the arteriotomy; removing the suture delivery device; and tying off the ends of the suture to close the arterial access site.

Other features and advantages should be apparent from the following description of various embodiments, which illustrate, by way of example, the principles of the invention.

BRIEF DESCRIPTION OF THE DRAWINGS

FIG. 2 shows a close-up view of a distal region of the closure device with the vessel wall locator in the deployed position.

FIG. 21A illustrates an arterial access device useful in the methods and systems of the present disclosure.

FIG. 21B illustrates an additional arterial access device construction with a reduced diameter distal end.

FIGS. 22A and 22B illustrate a tube useful with the sheath of FIG. 20A.

FIG. 23A illustrates an additional arterial access device construction with an expandable occlusion element.

FIG. 23B illustrates an additional arterial access device construction with an expandable occlusion element and a reduced diameter distal end.

FIGS. 24 and 25 show an embodiment wherein a proximal extension is removably connected to the Y-arm connector at a connection site.

FIGS. 29A-29D, FIGS. 30A-30D, FIGS. 31A and 31B, FIGS. 32A-32D, and FIGS. 33A and 33B, illustrate different embodiments of a variable flow resistance component useful in the methods and systems of the present disclosure.

FIGS. 38A-38E, 39, 40A-40E, and 41A-41F show operations in an exemplary interventional procedure.

DETAILED DESCRIPTION

Disclosed is a suture-based blood vessel closure device that can perform the dilation of an arteriotomy puncture, and therefore does not require previous dilation of the arteriotomy puncture by a separate device or by a procedural sheath dilator. The suture-based vessel closure device can place one or more sutures across a vessel access site such that, when the suture ends are tied off after sheath removal, the stitch or stitches provide hemostasis to the access site. The sutures can be applied either prior to insertion of a procedural sheath through the arteriotomy or after removal of the sheath from the arteriotomy. The device can maintain temporary hemostasis of the arteriotomy after placement of sutures but before and during placement of a procedural sheath and can also maintain temporary hemostasis after withdrawal of the procedural sheath but before tying off the suture. A suture-based vessel closure device also desirably can provide rapid access and control of suture ends in the instance of inadvertent sheath removal as well as provide a highly reliable hemostatic closure of the access site.

Figure 1A:
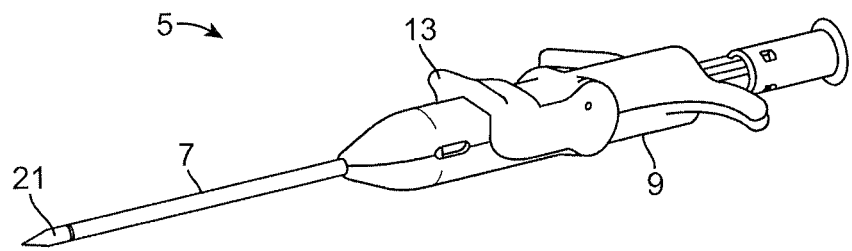
FIGS. 1A-1C show a suture-based vessel closure device or suture delivery device that can be used to position a loop of suture across a puncture in a blood vessel.

FIG. 1A shows a suture-based vessel closure device or suture delivery device 5 that can be used to position a loop of suture across a puncture in a blood vessel. The suture delivery device 5 generally includes a body comprised of a delivery shaft 7 attached to a proximal housing 9 having control elements such as a movable actuation handle 11 and/or actuation lever 13. The type, number, and shape of the control elements can vary. In an embodiment, the actuation handle 11 controls movement of a pair of suture capture rods 15 (shown in FIG. 1C). The actuation lever 13 controls positioning of a vessel wall locator 17 (shown in FIGS. 1B and 1C). At least one of the suture capture rods 15 is coupled to a suture 19 (FIG. 2) in a manner that permits a loop of the suture to be positioned across an arteriotomy for closure of the arteriotomy. The delivery device 5 may be at least partially configured in the manner described in U.S. Pat. No. 7,001,400, which is incorporated herein by reference in its entirety. As used herein, the term "proximal" means closer to the user and the term "distal" means further from the user.

With reference still to FIG. 1A, the device 5 includes a distal tip 21 that extends distally of a distal end of the delivery shaft 7. As described in detail below, in an embodiment the distal tip 21 is adapted to dilate an arteriotomy. A guidewire lumen extends entirely through the suture delivery device 5 from the distal end of the distal tip 21 to a proximal exit port of the delivery device 5. The guidewire lumen permits the entire delivery device 5 to be placed over a guidewire, for example, a 0.035 or a 0.038 inch guidewire. The axis of the delivery shaft 7 need not be straight, as the shaft may curve somewhat.

Figure 1B:
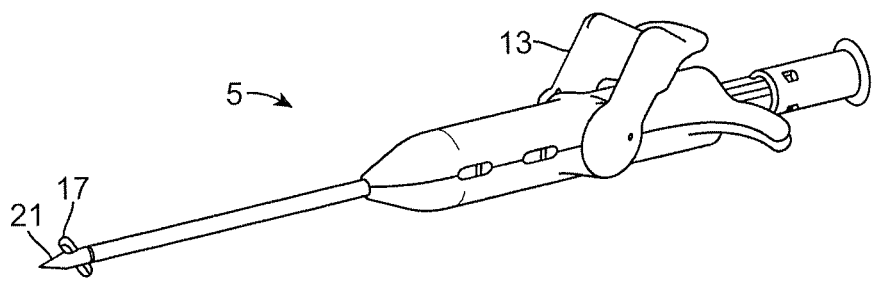
Figure 1C:
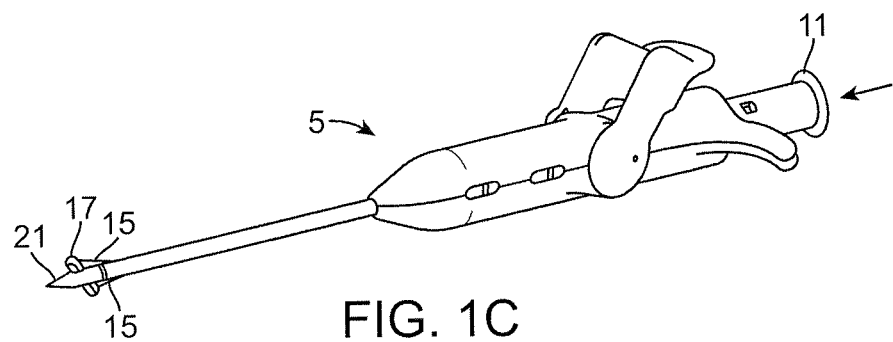

With reference to FIG. 1B, a vessel wall locator 17 in the form of a foot is movably positioned near the distal end of the delivery shaft 7. The vessel wall locator 17 moves between a stored position, in which the vessel wall locator 17 is substantially aligned along an axis of the delivery shaft 7 (as shown in FIG. 1A), and a deployed position, in which the vessel wall locator 17 extends laterally from the delivery shaft 7 (as shown in FIGS. 1B and 1C). In the stored position, the vessel wall locator 17 can be disposed within a receptacle of the delivery shaft 7 so as to minimize the cross-section of the device adjacent the vessel wall locator 17 prior to deployment.

The vessel wall locator 17 is coupled via a control element such as a control wire to the actuation element 13 on the handle 9. As shown in FIGS. 1A-1C, movement of the actuation element 13 causes movement of the vessel wall locator 17 between the stored position and deployed position. Actuation of the actuation element 13 slides the control wire (contained within the delivery shaft 7) proximally, pulling the vessel wall locator 17 from the stored position to the deployed position.

Suture capture rods 15 (FIG. 1C) are coupled to the actuation handle 11. Actuation of the actuation handle 11 cause the capture rods 15 to move between a non-deployed position wherein the capture rods 15 are contained in the delivery shaft 7 (shown in FIGS. 1A and 1B), and a deployed position (shown in FIG. 1C) wherein the capture rods advance distally outward of the delivery shaft 7 toward the vessel wall locator 17. In the deployed position, distal ends of the capture rods 15 mate with suture capture collars contained in lateral ends of the vessel wall locator 17.

Movement of the suture capture rods 15 to the deployed position causes at least one end of the suture to couple to the suture capture rods 15. The suture capture rods 15 can then be used to proximally draw the ends of the sutures through the vessel wall for forming a suture loop around the arteriotomy. At the end of the procedure after a procedural sheath has been removed, the suture can be tied in a knot and tightened distally against the arteriotomy to seal the arteriotomy. This can be achieved in various manners, some of which are described in U.S. Pat. No. 7,001,400, which is incorporated by reference in its entirety. In an embodiment, a short length of flexible filament 29 (FIG. 2) extends substantially directly between suture capture elements in the vessel wall locator 17. One suture capture rod attaches a suture 19 to one end of flexible filament. In this manner, the flexible filament links the suture 19 to the opposing suture capture rod. As the rods are drawn back using actuator 11, the flexible filament pulls the suture 19 through the vessel wall on one side of the arteriotomy, across the arteriotomy, and out the other side. When the actuator 11 has fully pulled out the suture rods 15, both ends of the suture 19 can be retrieved.

FIG. 2 shows a close-up view of a distal region of the delivery device 5 with the vessel wall locator 17 in the deployed position. The delivery device 5 is shown in partial cross-section to illustrate the internal components. The distal tip 21 tapers smoothly to the diameter of the delivery shaft 7 to permit the distal tip 21 to be used as a dilator. As mentioned, the tapered distal tip 21 dilates the arteriotomy as the delivery device 5 enters the blood vessel. In this regard, the distal tip 21 has features that are particularly adapted for dilating an arteriotomy. Such features include size, shape, materials, and/or material properties that are specifically adapted to dilate an arteriotomy. For example, the dilating distal tip 21 is constructed from materials and dimensions to reproduce the dilating function of a standard sheath dilator. For example, at least a portion of the tip may have a taper angle of 3° to 7° relative to a longitudinal midline axis of the suture closure device. In an embodiment, the distal tip has an equivalent stiffness and smoothness to polyethylene material. In an embodiment, the tapered portion of the tip 21 extends over a length of about 1 to 3 cm or about 1 to 2 cm. The tapered portion may taper outward from the distal-most location of the distal tip 21. It should be appreciated that the distal tip 21 is not required to be a dilating tip.

In addition, the distal tip 21 includes a guidewire lumen 31. As shown in FIG. 2, the guidewire lumen may extend through the entire device, or alternately through the entire distal region and delivery shaft 7 and exit distal to the proximal handle 9. In yet another alternate embodiment, the guidewire lumen extends through the dilator tip to a point on one side of the distal region of the suture delivery device distal to the vessel wall locator. In this latter case, the guidewire rides only over the distal region of the suture delivery device, rather than through the delivery shaft.

The guidewire lumen 31 forms an opening or exit at the distal end of the distal tip 21. The distal exit of the guidewire lumen 31 provides a smooth transition to the guidewire, so the device can smoothly and atraumatically be inserted into the vessel over the guidewire. Thus the diameter of the guidewire lumen may be close to the diameter of the guidewire itself when it exits the dilating tip. For example, for compatibility with an 0.035" or 0.038" guidewire, the dilating tip of the device can have a guidewire lumen of from 0.039" to 0.041" as it exits the tip (although it could be slightly larger for the remainder of the device). In addition, the leading edge of the dilating tip may be radiused, for example 0.050" to 0.075" radius, so there are no abrupt transitions as the device enters the vessel. Thus, as mentioned, a separate dilator is not needed to dilate the arteriotomy before deployment of the delivery device 5 through the arteriotomy. In an embodiment, the distal tip is located about 3 cm beyond the stitch delivery location, thus, about 3 cm distal of the vessel wall locator 17.

The distal portion of the delivery shaft 7 may include a position verification lumen that extends proximally from a position verification port just proximal to the vessel wall locator 17 to a position indicator at the housing 9. When the vessel wall locator 17 is properly positioned within the blood vessel, blood pressure causes blood to flow proximally into the position verification port, through the position verification lumen, and to the position indicator in the housing 9. Presence of blood in the position indicator provides an indication that the vessel wall locator 17 has entered the blood vessel and may be actuated to the "open" position (as in FIG. 1B). The position indicator may comprise a blood exit port, a clear receptacle in which blood is visible, or the like. It should be understood that a wide variety of alternative position verifications sensors might be used, including electrical pressure sensors, electrolytic fluid detectors, or the like.

With reference still to FIG. 2, a guidewire 33 slidably extends through the guidewire lumen 31 via an opening in the center of the distal tip 21 of the device 5. At a distal-most location, the guidewire lumen 31 is centered in the distal tip 21. That is, the guidewire 31 is aligned with the longitudinal midline or center-axis of the distal tip 21. The guidewire lumen 31 transitions toward an off-center position moving proximally through the delivery shaft 7. That is, at a location proximal of the distal most location of the distal tip 21, the guidewire lumen transitions to a position that is offset from the longitudinal center-axis of the delivery shaft 7. The vessel wall locator 17 is positioned on the delivery shaft 7 such that the suture placement site is centered around the delivery shaft 7. Thus, the sutures are placed at the center of the vessel puncture even though the guidewire 33 is off-center in the delivery shaft 7. Alternately, the guidewire lumen may be positioned in the central axis of the delivery shaft, and the vessel wall locator and suture placement sites are centered offset from the shaft central axis.

Figure 3A:
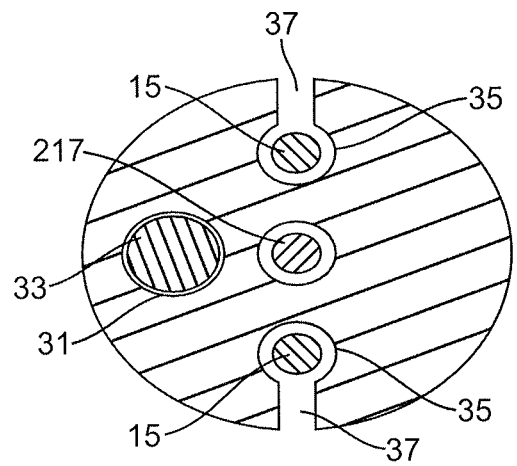
FIGS. 3A and 3B show cross-sectional views of the delivery shaft of the closure device along line 3A-3A of FIG. 2.
Figure 3B:
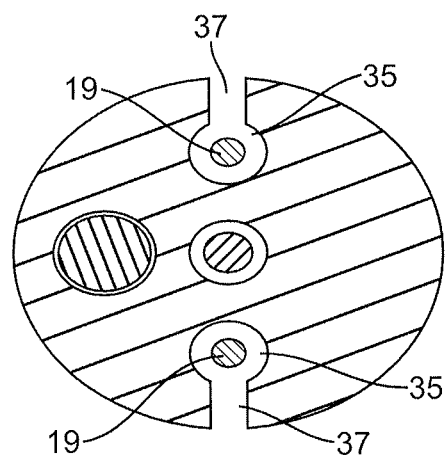

FIGS. 3A and 3B show a cross-sectional view of the delivery shaft 7 along line 3A-3A of FIG. 2. A pair of channels 35 extend longitudinally through the delivery shaft 7 near the outer surface of the delivery shaft. Each of the channels 35 communicates with a slot 37 that provides external access to the respective channel 35. In FIG. 3A, a suture capture rod 15 is positioned within each of the channels 35. The slot is sized and shaped such that the suture capture rod 15 is securely contained within the channel 35. In FIG. 3B, the suture capture rods have been pulled proximally, pulling the suture 19 with them; thus the figure shows the suture 19 positioned within each of the channels 35. As shown in FIG. 3B, the slots are larger than the suture 19 such that the suture 19 can be removed through the slots 37, such as by being peeled out of the slots 37.

Figure 4A:
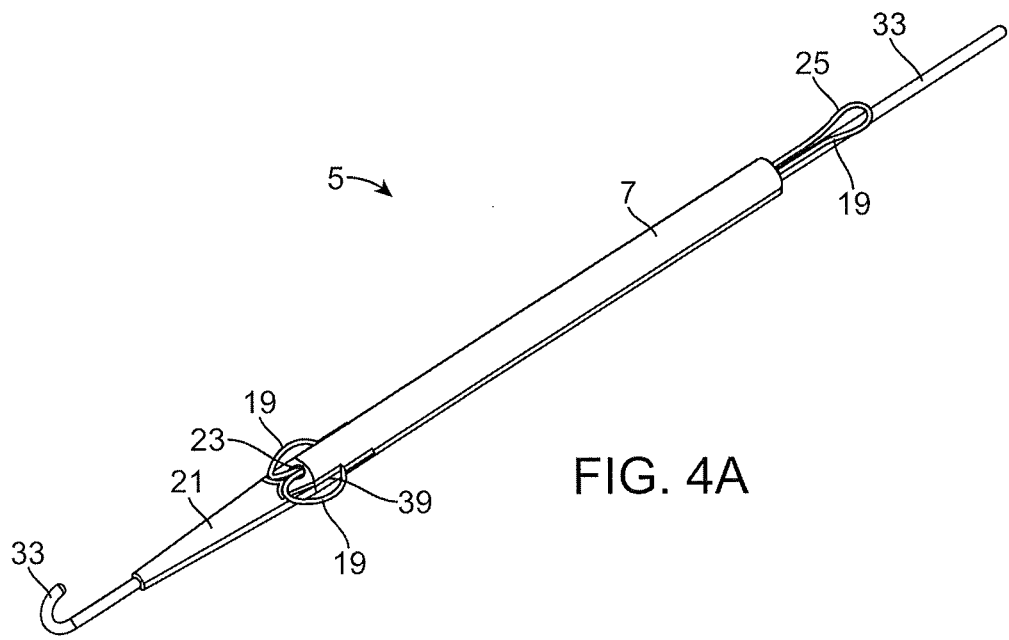
FIGS. 4A and 4B show a close-up view of an alternate embodiment of the distal portion of a suture delivery device that can be used to position a loop of suture across a puncture in a blood vessel.
Figure 4B:
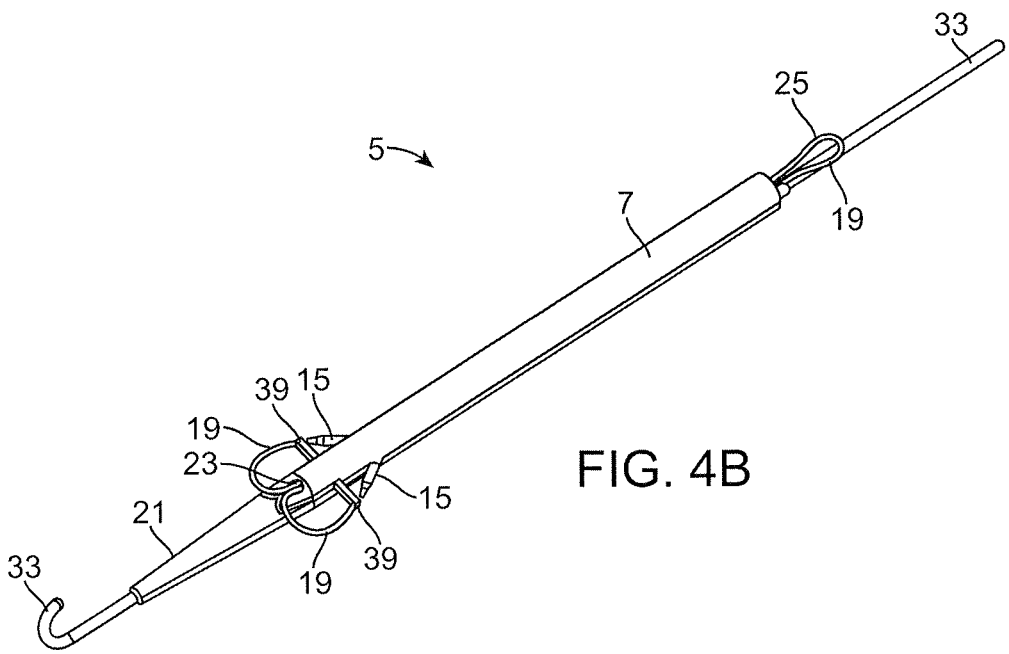

FIGS. 4A and 4B show a close-up view of an alternate embodiment of the distal portion of a suture delivery device 5 that can be used to position a loop of suture across a puncture in a blood vessel. A similar device is described in U.S. Pat. No. 7,004,952, which is incorporated by reference in its entirety. FIGS. 4A and 4B show the device 5 with a body comprised of the shaft 7 truncated in order to illustrate features of the device 5. The vessel wall locator is in the form of two extendable arms 39. As with the previous embodiment, the vessel wall locator may be coupled via a rod or other coupler to an actuation element 13 on a handle 9. A loop of suture 19 is positioned down the center of the delivery shaft 7 such that both ends of the suture 19 exit out a distal port 23 of the delivery shaft 7. The middle 25 of the loop of suture 19 exits out the proximal end of the delivery device 5. Each end of the suture loop is attached to the end of each extendable arm 39. As with the previous embodiment, the device includes a distal tip 21 with a central lumen for a guide wire 33. The distal tip 21 can optionally be a dilating tip as described above in the previous embodiment. Also as in the previous embodiment, the guide wire lumen may extend along the entire length of the delivery device, such that a guidewire can ride along the entire length of the suture delivery device 5 and exit out the proximal end, or may exit at a point in the delivery shaft distal to the proximal handle 9.

FIG. 4A shows the device with the extendable arms 39 in the retracted position. In this configuration, the delivery device 5 may be advanced over a guidewire into an arterial puncture. Once the device is in place, the extendable arms 39 may be extended outward which allows the device to be positioned accurately with respect to the vessel wall. FIG. 4B shows the device with the arms 39 in the extended position, with the ends of the suture loop 19 now also extended outwards. The suture capture rods 15 can now be extended and pierce the vessel wall to each side of the arterial puncture through which the delivery shaft 7 is located. The suture capture rods 15 are configured to capture each end of the suture loop 19. When the capture rods 15 are retracted, they draw the suture loop 19 through the vessel wall across the arterial puncture, until the loop of suture is entirely in the vessel wall and no length of suture loop remains in the delivery shaft. The extendable arms 39 can now be retracted to enable removal of the device from the arterial puncture.

In a method of use, the ends of the suture 19 are held in tension during removal of the suture delivery device 5 while the guidewire 33 remains in place. A procedural sheath and dilator is then placed over the guidewire and through the pre-placed sutures into the vessel. The guidewire and dilator are removed, and the procedural sheath remains in place. The sutures may be relaxed during the subsequent procedure. However, they may be tagged or anchored in some manner so that they may be grasped and held in tension to achieve rapid hemostasis in the case of inadvertent sheath removal. After completion of the procedure, the sutures are again held in tension during removal of the procedural sheath. The ends of the suture are tied and the knot pushed against the arteriotomy to achieve permanent hemostasis.

Figure 5:
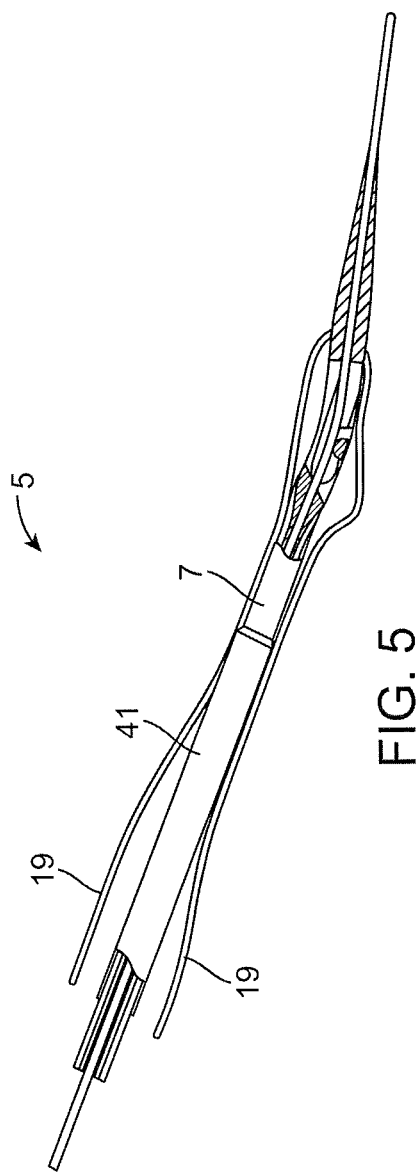
FIGS. 5 and 6 show two embodiments of a pre-mounted sheath being advanced along the closure device after the suture has been placed across the arteriotomy.

In an embodiment shown in FIG. 5, a sheath 41 is pre-mounted on the suture delivery device 5 (which can be any of the embodiments of delivery devices described herein). The sheath 41 is an elongated body, such as a tubular body, having an internal lumen sized to receive the delivery shaft 7 of the suture delivery device 5. The pre-mounted sheath 41 is initially positioned in a parked configuration wherein the sheath 41 is located on the proximal end or proximal region of the delivery shaft 7. The sheath 41 can remain in the parked configuration during suture placement. After the suture is deployed across the arteriotomy, the ends of the suture are captured and peeled away from the delivery shaft 7. The sheath 41 can then slide distally over the delivery device 5 into the arteriotomy. FIG. 5 shows the pre-mounted sheath being advanced after the suture 19 has been placed across the arteriotomy. Alternately, the step of advancing the pre-mounted sheath 41 may facilitate peeling away the sutures from the delivery shaft 7 in that the sheath 41, as it moves, physically abuts the sutures to cause the sutures to peel away. Once the pre-mounted sheath has been advanced into the arteriotomy, the delivery device 5 can then be removed through the sheath 41.

In an embodiment, the pre-mounted sheath 41 is an exchange sheath that provides a means for maintaining hemostasis of the arteriotomy while removing the suture delivery device 5 and then inserting a separate procedural sheath (such as the arterial access sheath 605 described below) for performing a procedure in the blood vessel. Once the suture is deployed across the arteriotomy, the exchange sheath 41 is positioned through the arteriotomy and then the suture delivery device 5 is removed. The procedural sheath is then inserted into the blood vessel through the exchange sheath 41. Once the procedural sheath is placed, the exchange sheath 41 can be removed. In an embodiment, the exchange sheath 41 is configured to be removed from the procedural sheath in a peel-away fashion. The pre-mounted sheath 41 may have a hemostasis valve either on its distal end or on its proximal end to prevent bleeding during this exchange. The hemostasis valve may be in the form of a closed end or membrane, with a slit or cross slit, or other expandable opening. The membrane is normally closed and opens to allow passage of a procedural sheath therethrough.

Figure 6:
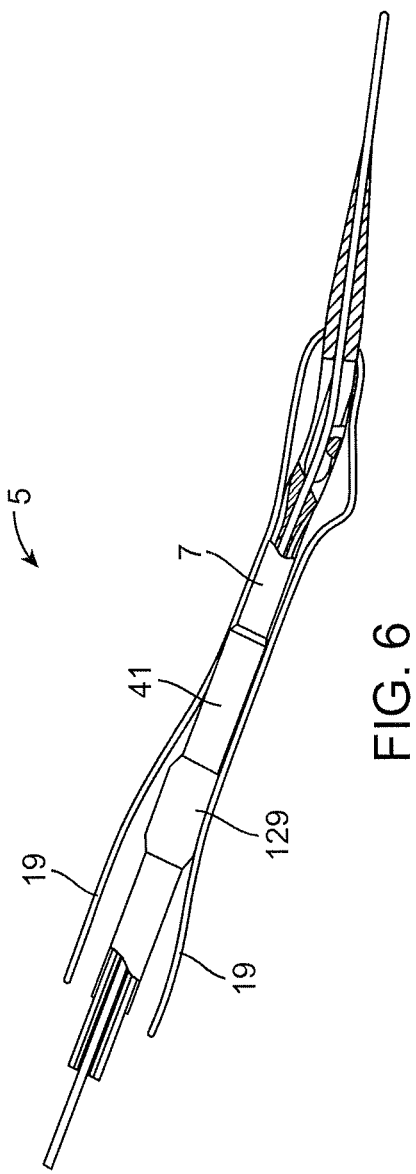

In another embodiment, the pre-mounted sheath 41 is an outer sheath which remains in place during the procedure. The outer sheath 41 may include an occlusion element 129, as shown in FIG. 6, that is adapted to increase in size within the blood vessel to occlude the blood vessel. Once the pre-mounted outer sheath 41 sheath is positioned in the vessel, the procedural sheath is inserted through the outer sheath 41 into the blood vessel. The procedural sheath is then used to introduce one or more interventional devices into the blood vessel. In an embodiment, the procedural sheath is a sheath such as the sheath 605 (described below), which is used to connect the blood vessel to a reverse flow shunt, such as the reverse flow shunt described below. The occlusion element 129 on the sheath 41 is used to occlude the blood vessel during the procedure. The intravascular occlusion element may be an inflatable balloon, an expandable member such as a braid, cage, or slotted tube around which is a sealing membrane, or the like. The outer sheath 41 may also include a sheath retention element such as an inflatable structure or an expandable wire, cage, or articulating structure which prevents inadvertent sheath removal when deployed.

This dual sheath configuration allows the pre-mounted sheath to be relatively short compared to the procedural sheath. The procedural sheath may require an extended proximal section such that the proximal adaptor where interventional devices are introduced into the sheath are at a site distance from the vessel access site, which may be advantageous in procedures where the vessel access site is near the fluoroscopy field. By keeping the pre-mounted sheath relatively short, the delivery shaft 7 may be kept shorter.

In another embodiment, the pre-mounted sheath 41 is the procedural sheath itself, such that use of an exchange or outer sheath is not necessary. The procedural sheath 41 may have a hemostasis valve, such as on the proximal end of the procedural sheath. Thus, when the suture delivery device 5 is removed, hemostasis is maintained. If a procedural sheath 41 is used which requires a proximal extended section, an extension can be added to the proximal end of the procedural sheath 41 after removal of the suture delivery device 5. Alternately, the delivery shaft 7 can have an extended length to allow pre-mounting of both the procedural sheath and proximal extension. The procedural sheath 41 may include an intravascular occlusion element for procedures requiring arterial occlusion. The intravascular occlusion element may be an inflatable balloon, an expandable member such as a braid, cage, or slotted tube around which is a sealing membrane, or the like. The procedural sheath may also include a sheath retention element such as an inflatable structure or an expandable wire, cage, or articulating structure which prevents inadvertent sheath removal when deployed.

An exemplary method of use of the suture delivery device 5 of FIGS. 1A-1C is now described. A puncture is formed into a blood vessel to provide access to the interior of the vessel. After accessing the blood vessel, a guidewire is inserted so that the guidewire extends into the skin and down through tissue along tissue tract. The suture delivery device 5 is advanced over the guidewire via the guidewire lumen 31 (FIG. 2) such that the guidewire directs the suture delivery device 5 along the tissue tract and into the vessel through the arteriotomy. As mentioned, the distal tip of the delivery device acts as a dilator such that it dilates the arteriotomy to facilitate entry. The distal tip of the delivery device can be used to dilate the arteriotomy without using any separate dilator device to dilate the arteriotomy. The delivery shaft 7 includes a position verification lumen. When the vessel wall locator 17 enters the blood vessel, blood flows through the position verification lumen to the proximal indicator to notify the operator that the vessel wall locator has entered the blood vessel.

When the vessel wall locator 17 is positioned inside the blood vessel, the actuation lever 13 on the handle 9 is actuated to move the vessel wall locator 17 to the deployed position inside the blood vessel. The deployed vessel wall locator 17 extends laterally from the delivery shaft 7, so that the vessel wall locator 17 can be drawn up against the vessel wall by pulling the delivery shaft 7.

The actuation handle 11 is then actuated to deploy the suture capture rods 15 toward the vessel wall locator 17. The suture capture rods mate with ends of the flexible link 29 contained in lateral ends of the vessel wall locator 17. This couples at least one end of the suture 19 to one end of the flexible link 29, and a suture capture rod 15 to the other end of the flexible link. The suture capture rods 15 can then be used to proximally draw the flexible link, and with it the suture 19, through the vessel wall for forming a suture loop across the arteriotomy. Alternately, the suture capture rods 15 mate directly with ends of the suture 19, which are located in the lateral ends of the vessel locator. The suture capture rods 15 are then used to draw the ends of the suture 19 through the vessel wall to form a suture loop across the arteriotomy. The suture capture rods then pull the suture ends out of the tissue tract above the skin, where then may be retrieved by the user.

As the suture ends are held in tension to maintain hemostasis, the suture delivery device 5 is removed over the guidewire, and exchanged for the procedure sheath. Manual compression may be applied over the arteriotomy site if needed for additional hemostasis control during the exchange of the suture delivery device 5 for the procedure sheath.

At the conclusion of the procedure, the procedure sheath is removed and the pre-placed suture ends are knotted and the knot pushed in place, in a similar manner to standard percutaneous suture closure devices. The suture ends may be pre-tied in a knot, in which case the knot is simply pushed into place. The tied suture ends are then trimmed.

In variation to this method, the suture delivery device 5 is inserted into the artery and the sutures are placed across the arteriotomy and drawn out of the tissue tract and above the skin, where they are retrieved by the user, as described above. The sutures are then separated from the delivery shaft 7. Prior suture delivery devices do not allow the sutures to "peel away" from the delivery shaft. Instead, in prior devices, the sutures are pulled out through the proximal end of the delivery device. The delivery device 5 disclosed herein permits the sutures to be peeled from the side of the delivery shaft 7. As mentioned, the sutures and suture capture rods are disposed in open-sided channels in the delivery shaft 7, as shown in FIGS. 3A and 3B. The channels are sized relative to the sutures such that the sutures can be lifted or pulled out of the channels. The suture capture rods still exit out the proximal end of the delivery device 5. The suture end that is attached to the suture capture rod is extracted from the delivery shaft 7 using a hook or pre-applied loop, and cut free of the suture capture rods. The other suture end can simply be pulled out of the side channels 35. The suture may have a pre-tied knot, as is disclosed in prior art. In this configuration, the knot must be located outside the body of the patient such that both ends of the suture may be grasped below the knot after the suture ends are retrieved.

With the suture free from the delivery device 5, the delivery device 5 can then be removed from the vessel while the guidewire 33 remains in the vessel. As mentioned, the guidewire channel extends entirely through the delivery device 5 to permit the delivery device to be easily removed from the guidewire. Prior to removing the delivery device 5, a pre-mounted sheath 41 is slid distally from the parked position (on the proximal end of the delivery shaft 7) into the tissue tract and through the arteriotomy. The act of pushing the sheath 41 forward can assist in pushing the sutures out of the channels 35 and away from the delivery shaft 7. As described above, the pre-mounted sheath may be an exchange sheath, an outer sheath for a dual-sheath configuration, or the procedural sheath itself. The sheath may further contain an intravascular occlusion element.

A variation on this configuration is to insert the suture delivery device 5 in the opposite direction from the ultimate direction of the sheath 41. This method may be used if there are anatomic restraints on the amount of blood vessel which may be entered, for example in a transcervical approach to carotid artery stenosis treatment. In this retrograde delivery, the delivery device is inserted into the vessel in a more perpendicular approach, so that the tissue tract from the skin to the artery created by the initial wire puncture and subsequently the suture delivery device may also be used to approach the artery with the procedural sheath in the opposite direction. Once the suture has been deployed and the suture ends have been retrieved, the suture delivery device is removed while keeping the guidewire in place. The guidewire is then re-positioned such that the tip is now in the opposite direction. The guidewire is advanced enough to provide support for the procedural sheath, which can now be advanced over the guidewire and inserted into the vessel. As it is critical not to lose the position of the guidewire during this change in guidewire direction, a feature may be added to the guidewire which prevents it from being removed from the vessel, for example an expandable element as described below.

In an embodiment, the suture delivery device 5 and the sheath 41 are used to gain access to the common carotid artery pursuant to treatment of a carotid artery stenosis, or an intracerebral arterial procedure such as treatment of acute ischemic stroke, intracerebral artery stenosis, intracerebral aneurysm, or other neurointerventional procedure. In another embodiment, the suture delivery device 5 and the sheath 41 are used to gain access to the common carotid artery pursuant to treatment of a vascular or cardiac structure such as transcatheter aortic valve replacement. In this particular embodiment, the sheath 41 is directed in a proximal or caudal direction. In an embodiment, transcervical access to the common carotid artery is achieved percutaneously via an incision or puncture in the skin through which the arterial access device 110 is inserted. However, it should be appreciated that the suture delivery device as well as any of the devices and methods described herein can be used with a variety of interventional procedures.

In another embodiment, the suture delivery device does not have a dilating tip and does not have a premounted sheath. Rather, the suture delivery device is configured as described, for example, in U.S. Pat. No. 7,001,400. The suture delivery device is used to suture an arteriotomy performed in the common carotid artery via transcervical access. In this embodiment, shown in FIGS. 7A and 7B, the suture delivery device generally has a shaft 7 having a proximal end 14 and a distal end 16. A proximal housing 18 supports a needle actuation handle 20. A flexible, atraumatic monorail guidebody 22 extends distally of distal end 16 of shaft 12.

Figure 7A:
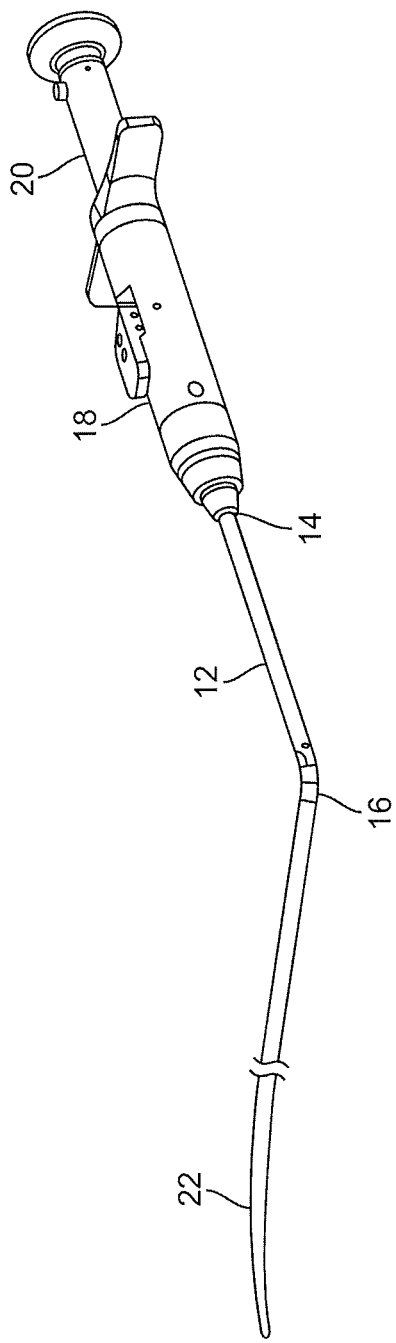
FIGS. 7A-7B show another embodiment of a suture-based vessel closure device or suture delivery device.
Figure 7B:
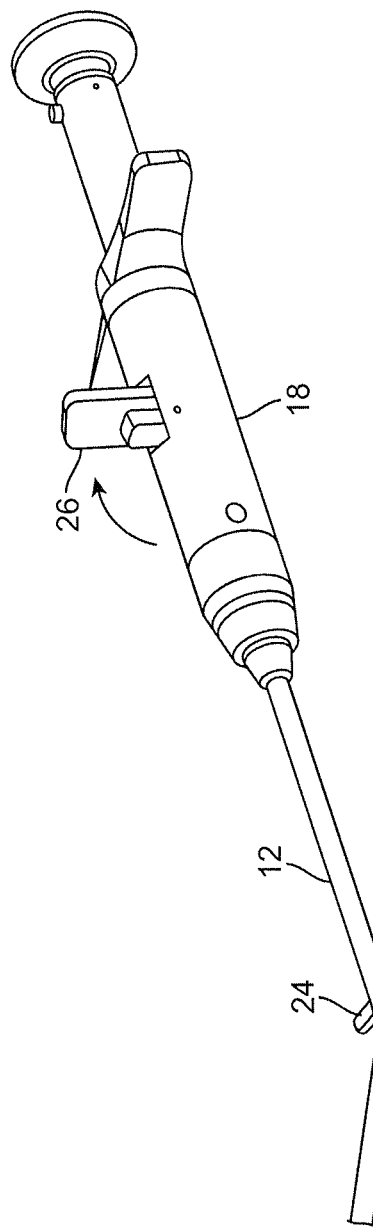

As shown in FIG. 7B, a foot 17 is articulatably mounted near the distal end of shaft 12. The foot 17 moves between a low profile configuration, in which the foot is substantially aligned along an axis of shaft 12 (as illustrated in FIG. 7A), to a deployed position, in which the foot extends laterally from the shaft, upon actuation of a foot actuation handle 26 disposed on proximal housing 18. The suture delivery device shown in FIGS. 7A-7B delivers the sutures in a similar manner to the way that the suture delivery device of FIGS. 1A-1C delivers the suture.

Figure 8:
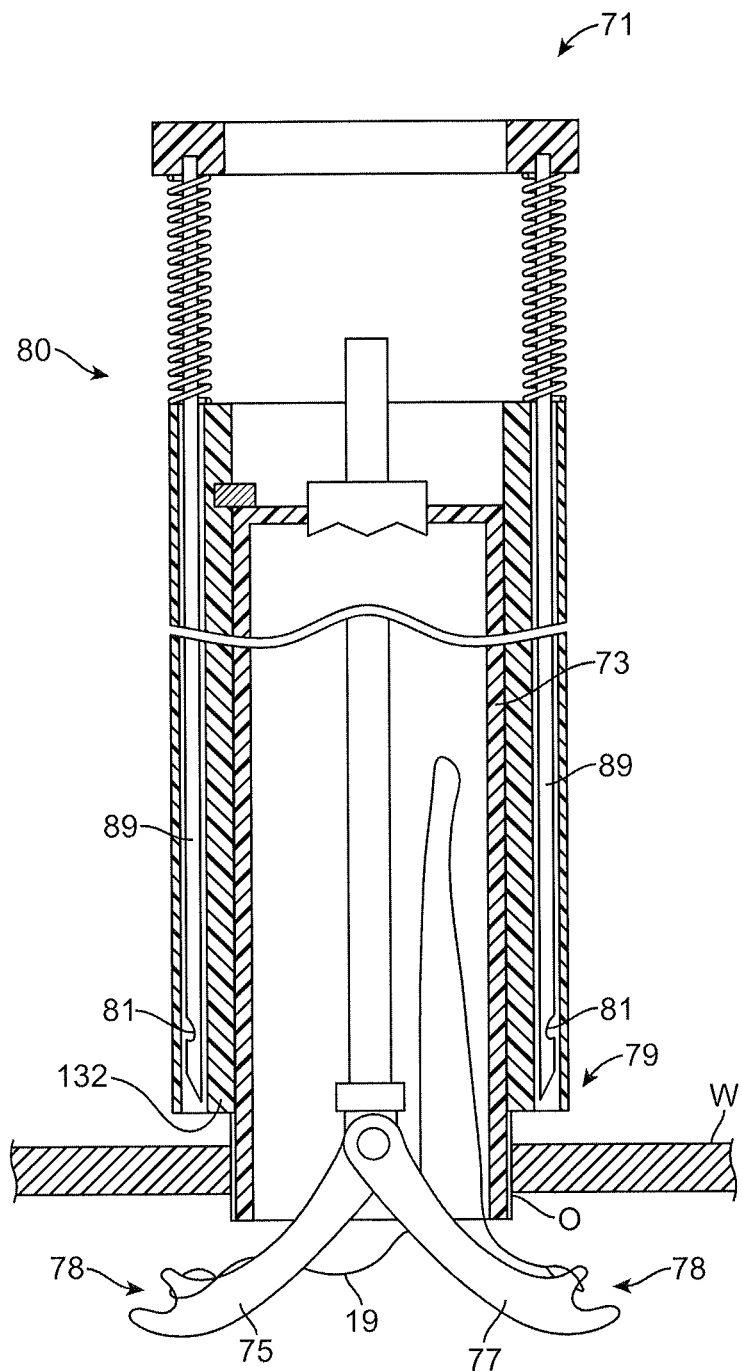
FIGS. 8 and 9 show portions of another embodiment of a suture delivery device.

FIG. 8 shows another embodiment of a suture delivery device, generally designated 71, for suturing vessel walls and other biological tissue. The device is for use in suturing an arterial vessel walls W. The device 71 comprises a suture introducer housing 73 for insertion into an opening O in the arterial wall W. A vessel wall locators in the form of suture clasp arms 75, 77 are deployably housed in the housing during insertion, and after insertion into the vessel, the arms are deployed to the position shown in FIG. 8. When deployed, the suture clasp arms extend outside the circumference of the suture introducer housing 73. Each arm has at least one means, generally designated 78 and schematically illustrated, for clasping a suture 19. A penetrating mechanism, generally designated 79, with needles 89 is provided for penetrating the vessel wall W. The penetrating mechanism is provided on either the suture introducer housing 73 or on a suture catch assembly, generally designated 80. When, as shown in FIG. 8, the penetrating mechanism is part of the suture catch assembly 80, the penetrating mechanism also comprises a suture catch 81 for catching the suture 19 and dislodging it from the clasping means 78. The suture catch assembly operates to pull the suture held by the suture catch through the vessel wall. After the ends of the suture are pulled outside the vessel, the introducing housing can be removed and the suture tied to close the vessel.

Figure 9:
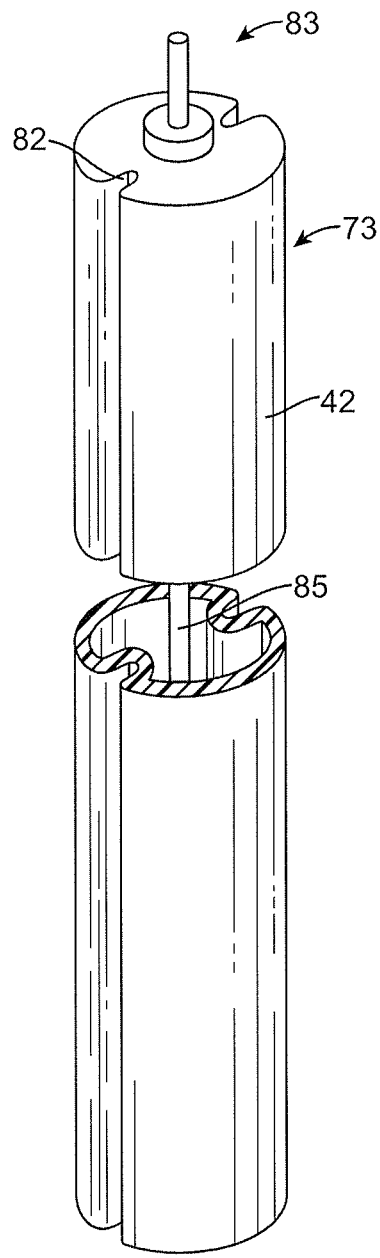

In an embodiment shown in FIG. 9, the suture introducer housing 73 is a generally cylindrical and thin walled hypo tube such as a hollow elongated cylindrical member with a thin wall such that the inner diameter and outer diameter vary by a relatively small amount in the range of few thousandths of an inch to tens of thousandths of an inch. The outer surface 42 of the housing comprises a key way groove 82 (exaggerated for clarity) to align the housing with a key on the inner surface of the suture catch assembly 80 (FIG. 8). An arm actuation assembly 83 for deploying the suture clasp arms protrudes from the proximal end of the housing, and an actuating rod 85 extends from the actuation assembly through the housing to the suture clasp arms. The suture delivery device of FIGS. 8 and 9 is described in U.S. Pat. No. 5,860,990 and U.S. Pat. No. 7,004,952, both of which are incorporated by reference in their entirety.

The suture delivery device of FIGS. 8 and 9 generally works by actuating an arm on the suture delivery device from a first position wherein the arm is within the suture delivery device to a second position wherein the arm is extended away from the elongate body. The arm holds a portion of a suture. At least one of the needles 89 is advanced in a proximal to distal direction along at least a portion of the suture delivery device toward the arm, the needle being advanced through tissue of the artery. A portion of the needle is engaged with the portion of the suture and the needle is retracted in a distal to proximal direction to draw the suture through the artery tissue.

Figure 10A:
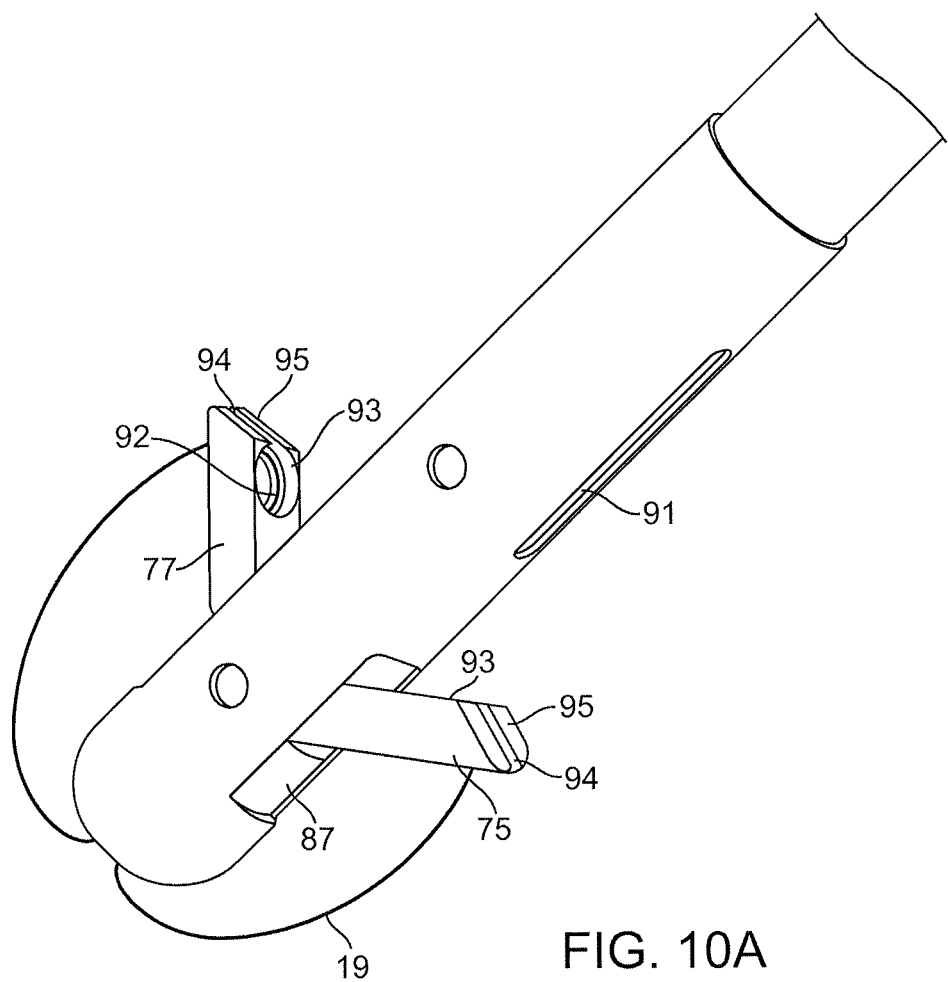
FIG. 10A is a perspective view of an embodiment of a distal region of a suture delivery device with the suture clasp arms partially deployed.
Figure 10B:
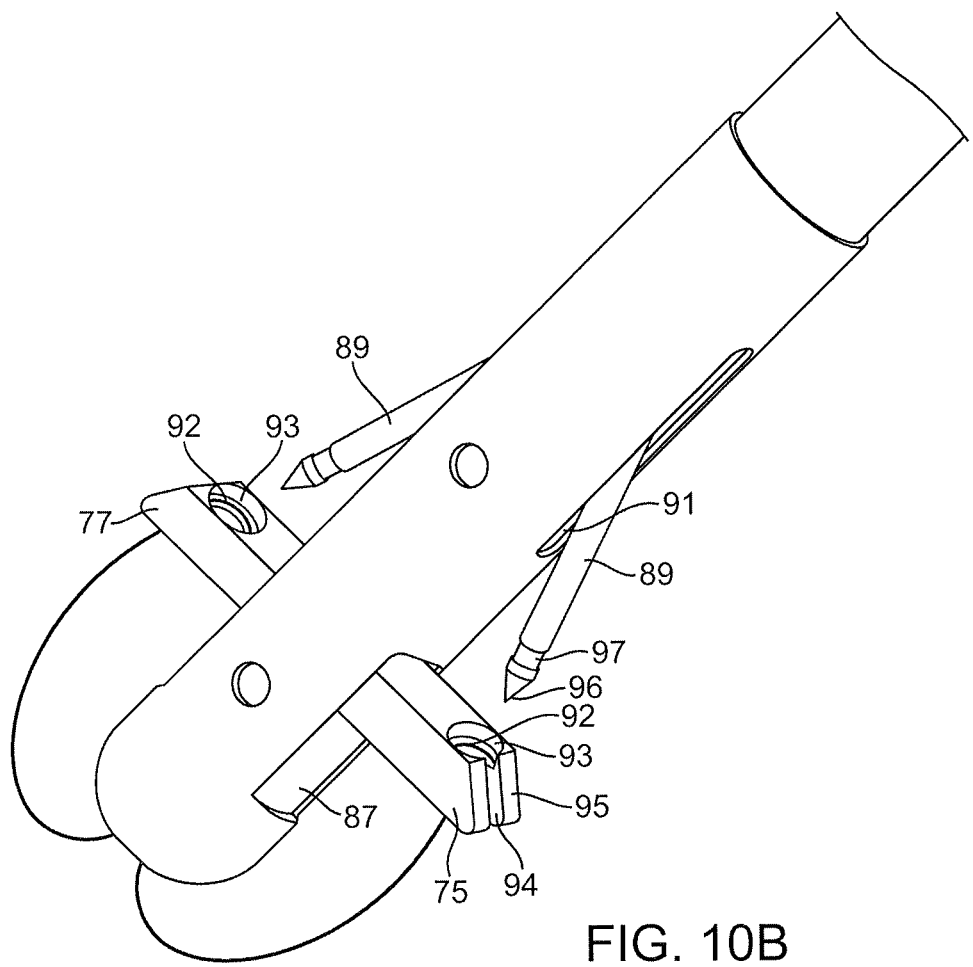
FIG. 10B is a perspective view of the suture delivery device with the suture clasp arms fully deployed.
Figure 10C:
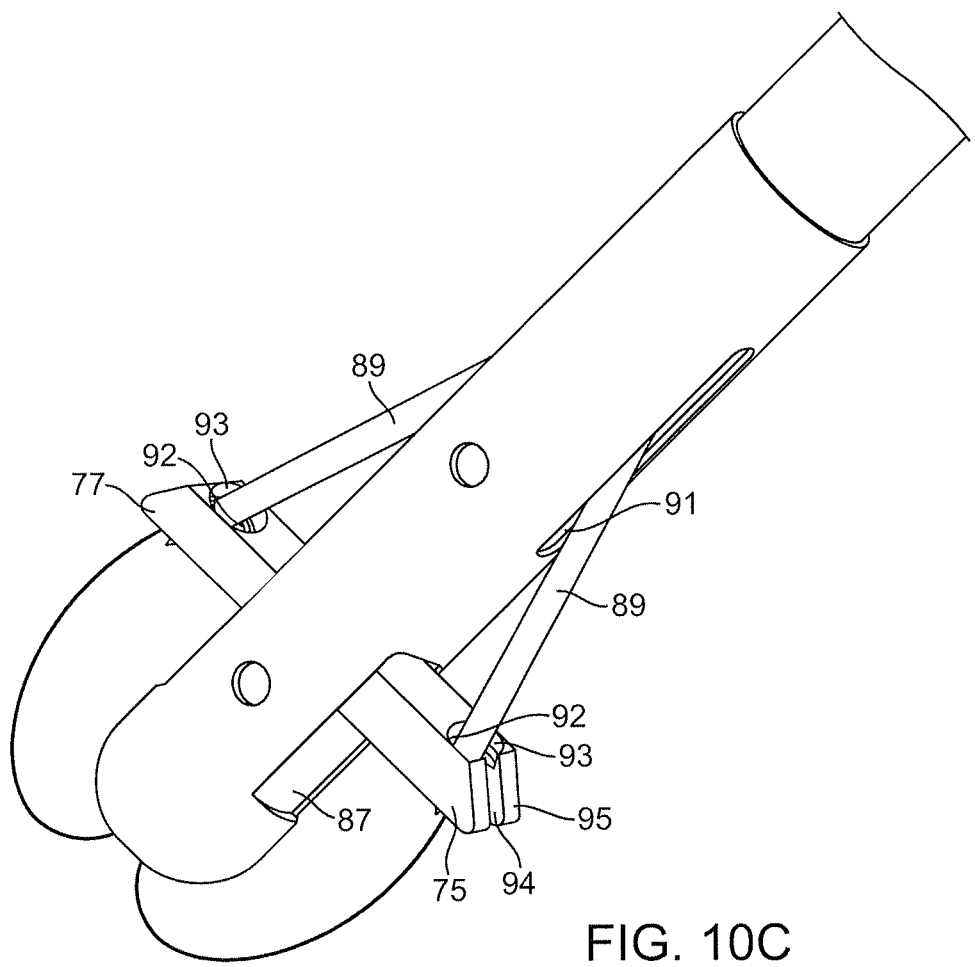
FIG. 10C shows two flexible needles extending out of needle apertures and engaging the suture clasp arms.

FIG. 10A is a perspective view of an embodiment of a distal region of a suture delivery device with the suture clasp arms 75, 77 partially deployed out of apertures 87. FIG. 10B is a perspective view of the suture delivery device with the suture clasp arms 75, 77 fully deployed. FIG. 10C shows two flexible needles 89 extending out of needle apertures 91 and engaging the suture clasp arms 75, 77. The device of FIGS. 10A-10C is not shown with a dilating tip although it should be appreciated that the device could be configured with a dilating tip pursuant to this disclosure.

The ends of the suture 19 are provided with loops 92 that are configured to engage with the needles 89. The suture clasp arms 75, 77 each comprise an annular recess 93 for holding the suture looped end 92, a slit 94 for the length of the suture 19, and a sloped end 95. Each of the flexible needles 89 comprises an extended shaft, a penetrating distal tip 96, and a groove 97 near the distal tip 96. The needle groove 97 acts as a detent mechanism or suture catch. In an embodiment, the grooves 97 extend around the complete circumference of the needles 89. In other embodiments, the grooves 97 are partially circumferential along the radial edge of the needles 89. The loops 92 correspond generally in diameter to grooves 97 of the needles 89, but are sufficiently resilient to expand in diameter in response to the downward force of the needles 89.

The general use and operation of the suture clasp arms 75, 77 is now described. The looped ends 92 of the suture 19 are placed within the annular recess 93 of the suture clasp arms 75, 77. The distal end of the device is inserted into biological tissue, and the suture clasp arms 75, 77 are deployed radially outward, as shown in FIG. 10B. The penetrating flexible needles 89 pass distally through the biological tissue (e.g., artery tissue) to be sutured and engage the suture clasp arms 75, 77, as shown in FIG. 10C.

When the distal tips 96 pass through the looped ends 92 of the suture 19, the looped ends 92 flex radially outward momentarily. As the needles 89 continue to advance distally, the looped ends 92 come in contact with the grooves 97. The looped ends flex radially inward and fasten around the needle grooves 97, such that pulling the needles 89 proximally causes the suture ends 92 to follow the proximal movement of the needles 89 to draw the suture proximally through the artery tissue.

Additional Embodiments

Figure 11A:
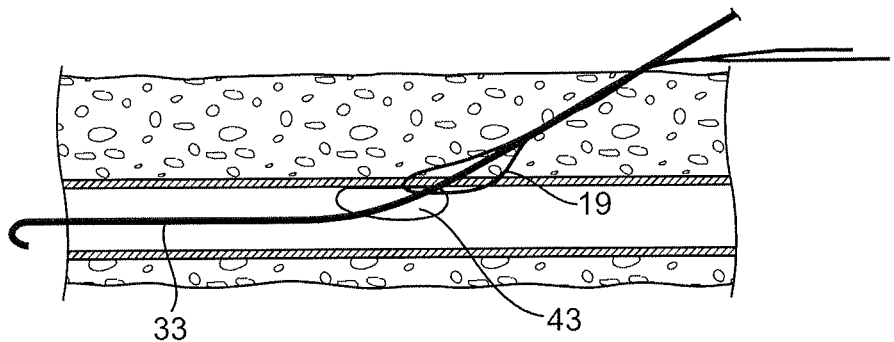
FIGS. 11A-13 show a guidewire with deployment of an expandable sealing element or elements to be used with a closure device

In another embodiment, the guidewire 33 includes at least one expandable sealing element 43 mounted on the guidewire. The expandable element 43, shown in FIGS. 11A-11C, can expand against the interior vessel wall to maintain hemostasis of the vessel access site, such as during exchange of the suture delivery device 5 for the procedural sheath, and during removal of procedural sheath. Alternately, the guidewire can be used to maintain hemostasis if the suture delivery device did not adequately place the suture in the tissue, and the device is needed to be exchanged for another vessel closure device. The second vessel closure device may be another suture delivery device, or may be another type of vessel closure device. This guidewire with sealing element may be used to exchange vessel closure devices either if the sutures are placed before the procedural sheath is placed or at the end of the procedure after sheath removal.

The expandable element 43 can be positioned a predetermined distance proximal from the distal tip of the guidewire. In an embodiment, the expandable element 43 is positioned about 3 cm proximal of the distal tip of the guidewire. This ensures that the distal tip of the guidewire is inserted a predetermined distance beyond the expandable element 43.

The expandable element must be collapsed when the suture delivery device is inserted into the vessel. The dilator tip 21 of the suture delivery device 5 may have an indicator lumen 45 for a blood mark. Thus, as soon as the dilator tip 21 of the delivery device 5 enters the blood vessel, an indication is provided to the operator so that the operator knows to deflate or collapse the expandable element 43 on the guidewire. The expandable element 43 can vary in structure. For example, the expandable element 43 can be a balloon, an expandable member such as a braid, cage, or slotted tube around which is a sealing membrane, or the like.

Figure 11B:
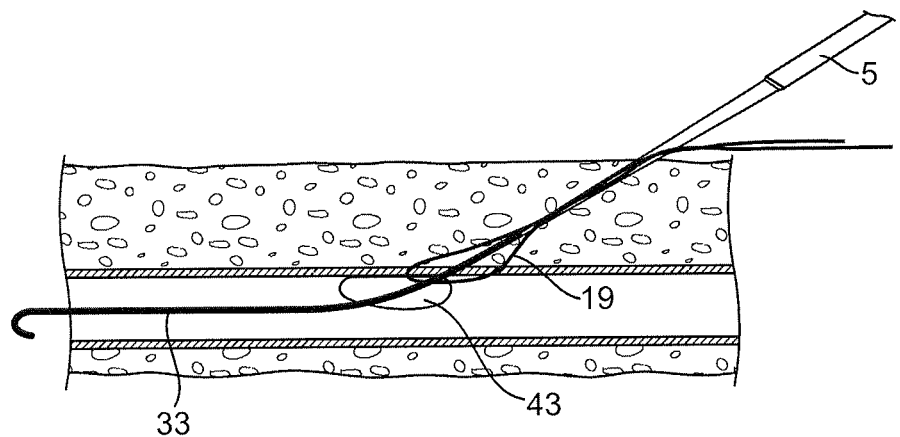
Figure 11C:
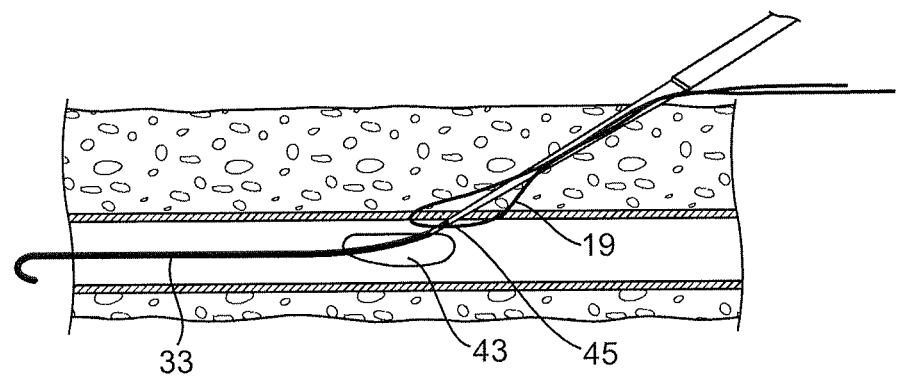
Figure 12:
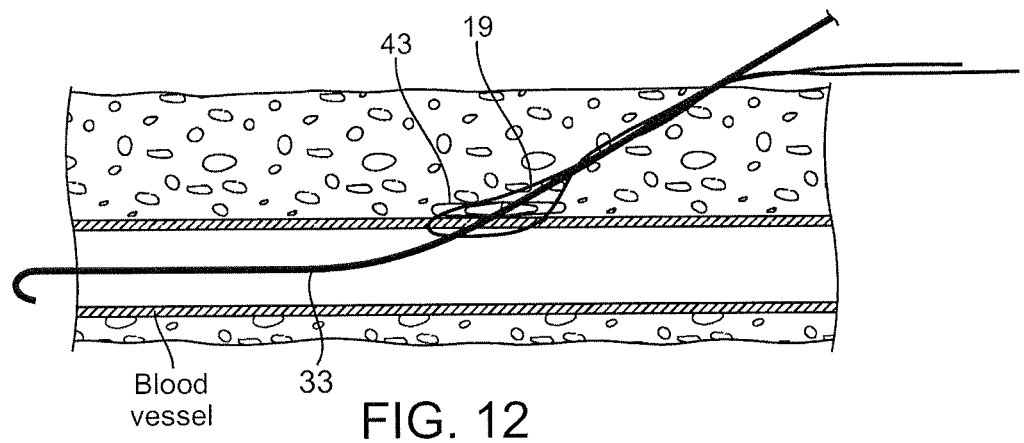

As shown in FIGS. 11B-11C, the expandable sealing element 43 can be positioned inside the blood vessel during use. Once the expandable element 43 is positioned in the blood vessel, the operator can pull it back proximally such that the expandable element 43 is sealed against the interior vessel wall. Arterial blood pressure within the vessel will also help exert pressure of the sealing element against the interior vessel wall, so that only a small amount of force, if any, may be needed to maintain hemostasis. In another embodiment, shown in FIG. 12, the expandable element 43 is positioned outside the blood vessel. The operator pushes the expandable element forward against the exterior vessel wall such that the expandable element 43 exerts pressure against the exterior vessel wall to achieve and maintain hemostasis.

Figure 13:
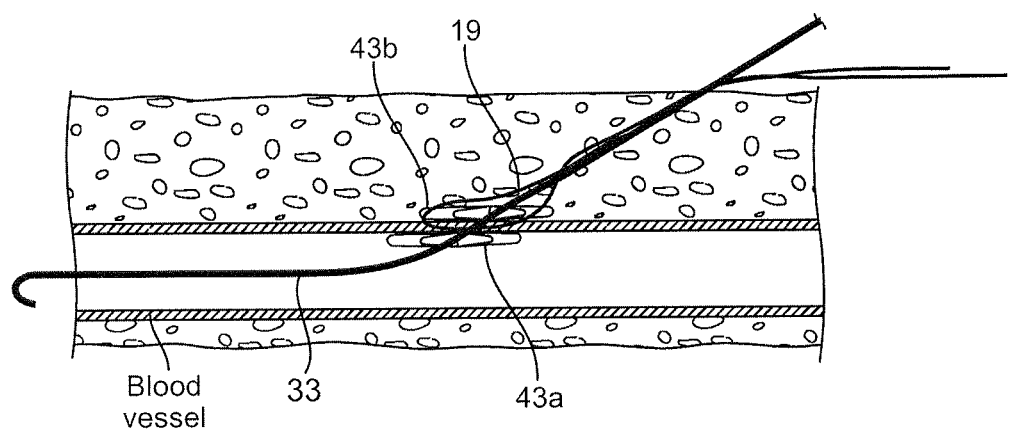

In yet another embodiment, the guidewire includes a pair of expandable sealing elements 43a and 43b, as shown in FIG. 13. During use the blood vessel wall is interposed between the expandable elements 43a and 43b with the expandable elements 43 exerting pressure on the vessel wall. This advantageously locks the position of the guidewire against movement relative to the vessel wall. The expandable elements 43a and 43b may be spring-loaded toward each other to achieve the pressure on the vessel wall. In a variation of the multi-expandable element embodiment, the expandable elements 43 are inflatable balloons. During use, care is taken that expandable portion does not increase the size of the arteriotomy, unless it is to be used to "pre-dilate" the arteriotomy.

Figure 14:
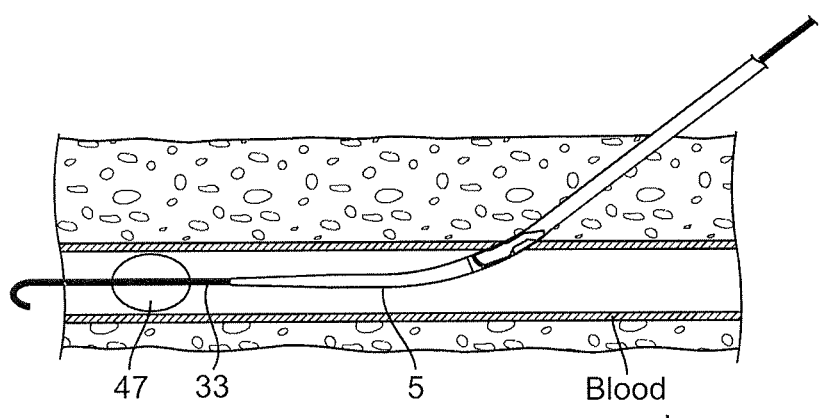
FIG. 14 shows a guidewire embodiment having an intravascular anchor.

In another embodiment, the guidewire includes an intravascular anchor that maintains the position of the guidewire relative to the blood vessel during insertion of the delivery device 5 and/or the procedural sheath into the blood vessel. As shown in FIG. 14, the anchor 47 can be, for example, an inflatable balloon, expandable cage or braid, or other element that secures to the interior vessel wall. In the case of an expandable or inflatable anchor 47, the anchor 47 expands to a size such that the anchor 47 exerts sufficient force against the vessel wall to secure the anchor 47 in place.

In an embodiment, the expandable element may serve as both an expandable sealing element and an intravascular anchor. For example if the expandable element was a balloon, inflation at one diameter may be sufficient to create a seal around the arteriotomy as well as anchor the guidewire in the vessel. Alternately, the expandable element is inflated to one diameter to seal the arteriotomy, and a greater diameter to anchor against the vessel wall. Similarly, a mechanically expandable element may be expanded to both seal and anchor, or be expanded to one state sufficient to create a seal, and expanded further to anchor against the vessel wall. The device may need to be repositioned between the sealing expansion and the anchor expansion states.

Figure 15:
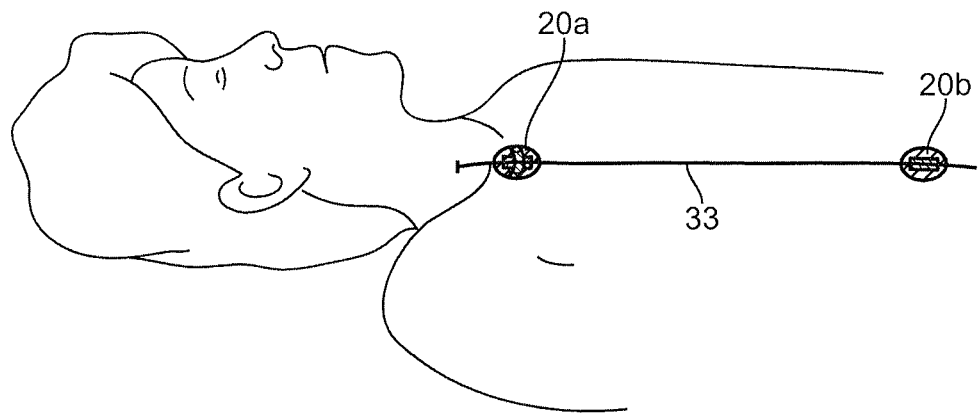
FIGS. 15-17 shows another guidewire anchor embodiment wherein the guidewire attaches to one or more clips that can be secured to the skin of the patient to hold the guidewire in place.

FIG. 15 shows another embodiment wherein the guidewire 33 attaches to one or more clips 51 that can be secured to the skin of the patient to hold the guidewire in place. The clips 51 can be secured to the patient using various means including an adhesive backing. The clips 51 can be positioned on the patient's skin in any of a variety of configurations. In the embodiment of FIG. 15, two clips 51 are used including one clip 51a near the entry location into skin and another clip 51b further from the entry location. The clips 51 serve to hold the guidewire in place at all times. The clip 51b may be released as the delivery device 5 device is loaded onto wire, then re-clipped and the clip 51a is released as the delivery device 5 inserted into skin and positioned into the blood vessel. In a similar fashion, the clips can be used to maintain the guidewire 33 position while the delivery device is removed, and while the procedural sheath is inserted into the blood vessel.

Figure 16:
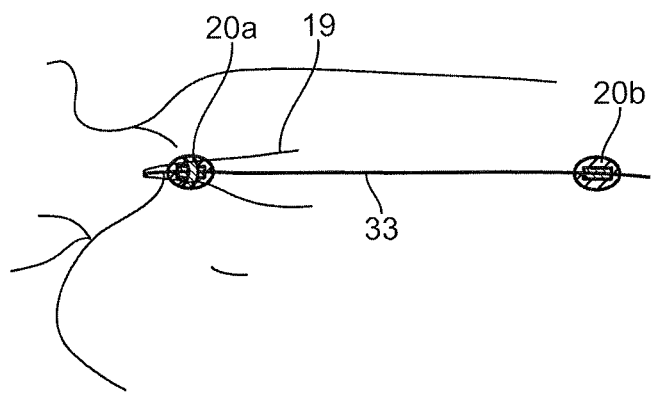
Figure 17:
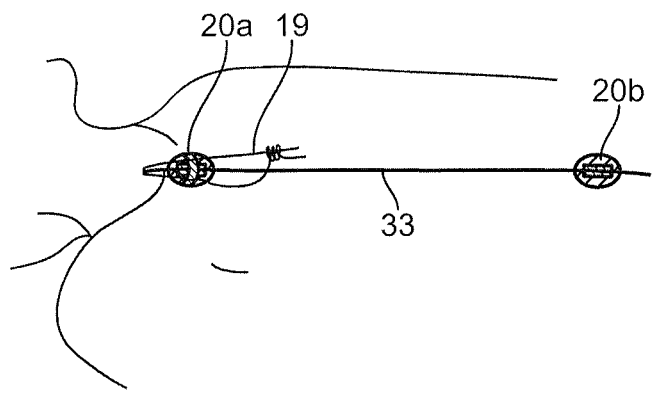

The clips 51 can also be used for management of the closure suture 19. The clips 51 can include one or more attachment means, such as slots, into which the suture can be inserted and held. FIGS. 16 and 17 show an example wherein the suture is not pre-tied (FIG. 16) and when the suture is pre-tied (FIG. 17). The sutures could also be both placed to the same side of the clip 51. The clips 51 may be configure to hold the suture in tension, such as during times when hemostasis is needed to keep sutures in tension to maintain hemostasis until procedural sheath can be placed. In this case, the knot is either not pre-tied or tied but far enough back that it is outside the skin and both sides of the stitch can be held in tension. The suture can be held in tension either manually, or with a clip or cleat on the skin. The suture back end can be attached to a tag or handle, or preattached to the clip or cleat which is then secured to the skin, to make this process easier. The sutures can either be kept in this clip or cleat during the intervention, or be removed if they are in the way, then reinserted after sheath removal but before knot tying. Or, the sutures can be manually held in tension and then the knot tied immediately afterwards. Or, if the knot is pre-tied, the knot can simply pushed down in to place.

Figure 18A:
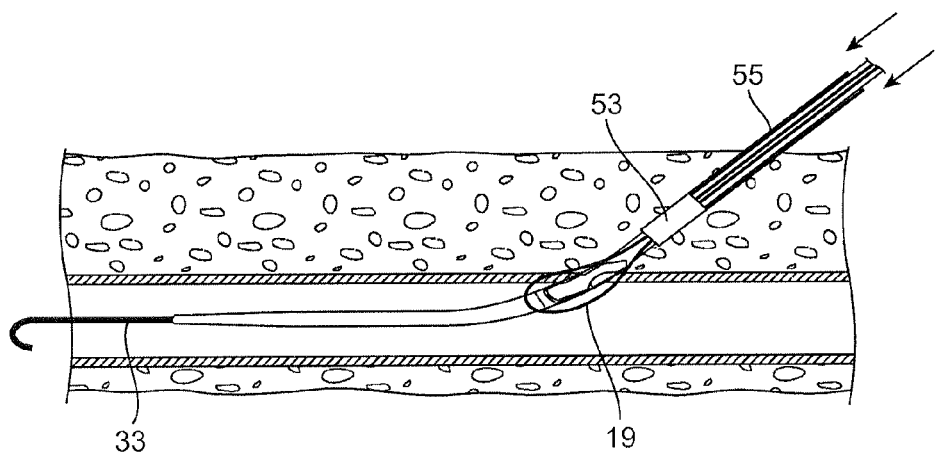
FIGS. 18A-18C show an embodiment of the closure device wherein a self-closing material is pre-loaded on a proximal region of the delivery shaft.
Figure 18B:
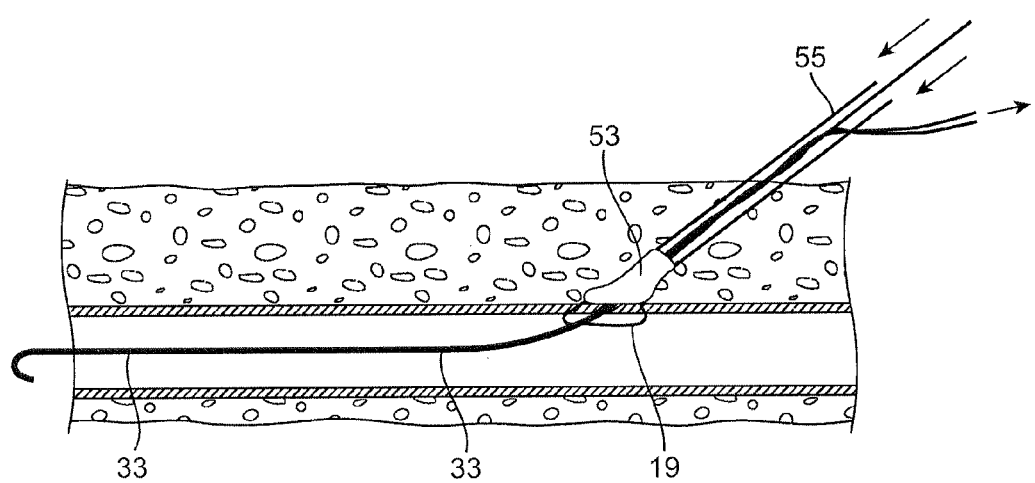
Figure 18C:
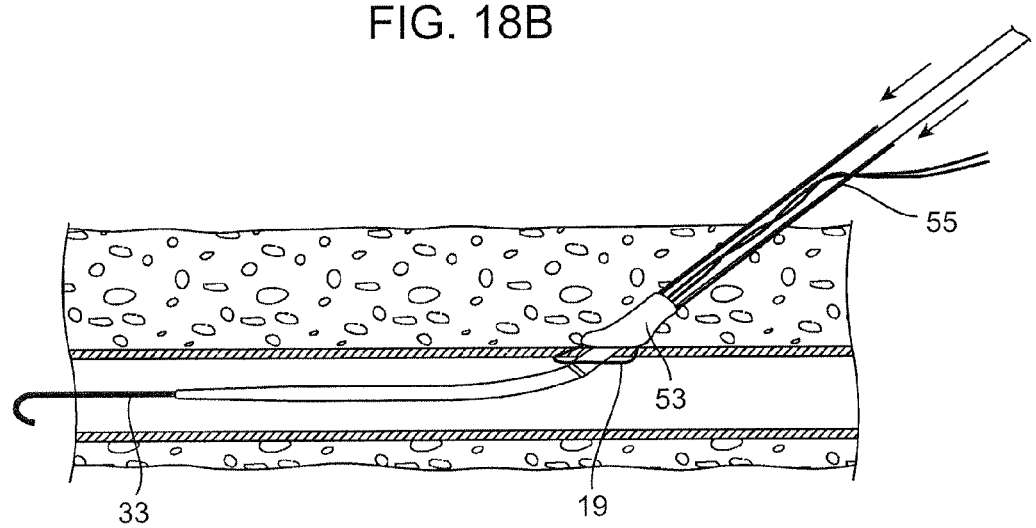

In another embodiment, shown in FIGS. 18A-18C, a self-closing material 53 is pre-loaded on a proximal region of the delivery shaft 7. A hole extends through the center of the self-closing material and the delivery shaft 7 is positioned through the hole. The self-closing material is configured to automatically close over the hole when the delivery device 5 is pulled out of the hole. The self-closing material can be a rubber plug or membrane with a hole, slit, cross slit, duck-bill valve, or a compressible material such as a foam, or simply a pair of spring members (such as a wire or a flat spring) that close over the arteriotomy when the device 5 is pulled out. The self-closing material can also be a collagen plug, a bioabsorbable polymer, a non-bioabsorbable polymer such as Dacron or ePTFE, or other appropriate biocompatible material. If the self-closing material is temporary, the material cab be a soft elastomer, such as silicone rubber, or polyurethane.

Just prior to removing the delivery device 5 from the arteriotomy, the self-closing material is pushed distally over the arteriotomy such as with a pushing element 55 such as push rod or tube, as shown in FIG. 18A. The pushing element 55 may be integral to the delivery device 5 or it may be a separate accessory item. The self-closing material is held in compression over the arteriotomy to maintain hemostasis, as shown in FIG. 18B. The sutures 19 that were just placed, as well as the guidewire which remains in place, pass through the center opening of the self-closing material. The procedural sheath is then placed over the guidewire through the self-closing material, through the arteriotomy and into the blood vessel, as shown in FIG. 18C. The pusher holding the self-closing material in compression against outside of vessel wall can then be relaxed. After the procedure is completed, the pusher can again be pushed to apply compression to arteriotomy until a knot is tied in the suture. Where the pusher is a rigid sleeve, the pusher can double as a means to provide a channel for facilitating device exchange through tissue tract.

In a variation of this embodiment, the self-closing material remains in place to act as a hemostasis material at the end of the procedure. The material is pre-loaded on the delivery shaft, and the suture capture rods are threaded through locations to each side of the delivery shaft. Thus when the sutures are pulled out of the delivery shaft, they are also pulled through two side holes of the self-closing material. As above, the material is pushed into place and acts as temporary hemostasis during device exchange. However, at the end of the procedure, the material remains in place when the suture ends are tied off to achieve permanent hemostasis.

Figure 19A:
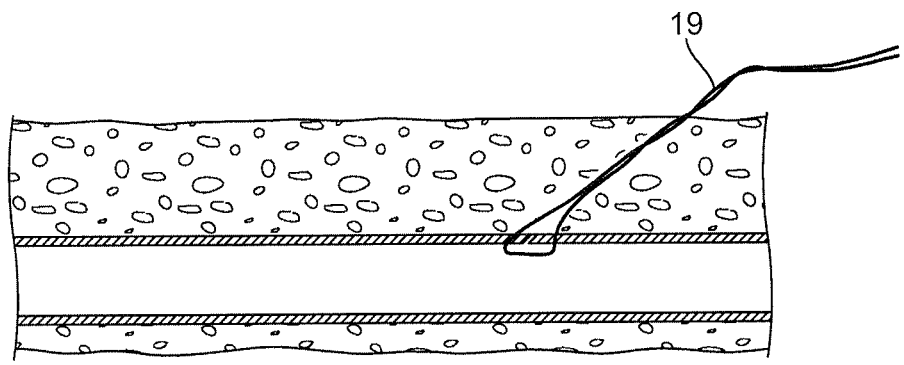
FIGS. 19A-19C show an embodiment wherein a hemostasis material is positioned over the arteriotomy location after removal of a procedural sheath.
Figure 19B:
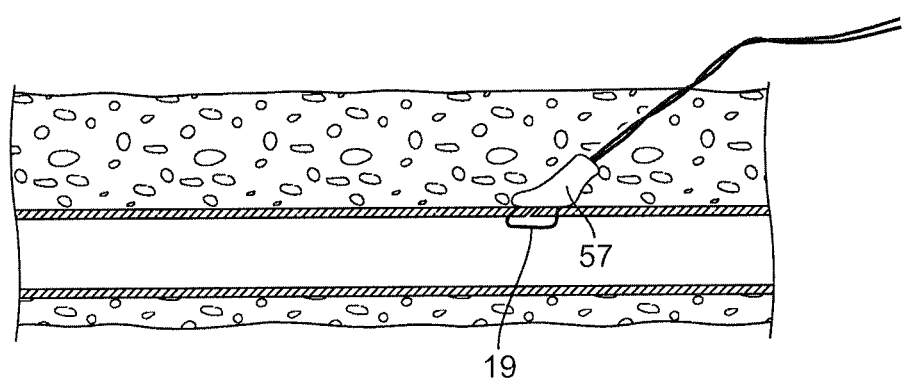
Figure 19C:
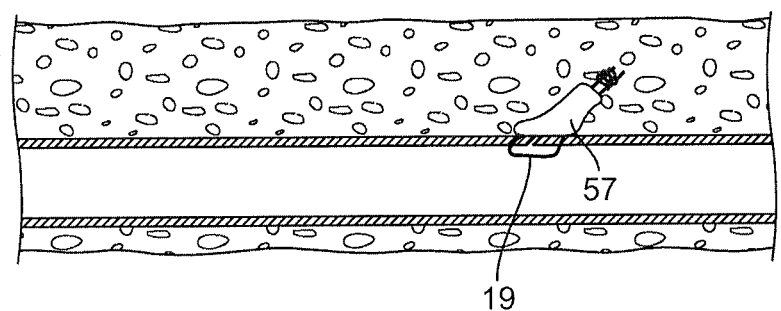

In another embodiment, shown in FIGS. 19A-19C, a hemostasis material 57 is positioned over the arteriotomy location after removal of the procedural sheath. The hemostasis material 57 is placed over the suture 19 before the suture knot is tied or during the tying of the suture knot. The knot secures the hemostasis material in place over the arteriotomy. Alternately, the hemostasis material is inserted over the arteriotomy after the suture knot is tied, and either another tie or a clip can be used to hold the hemostasis material against the arteriotomy. The hemostasis material can be, for example, a collagen plug, a bioabsorbable polymer, a non-bioabsorbable polymer such as Dacron or ePTFE, or other appropriate biocompatible material. The hemostasis material can be a temporary or a permanent material. U.S. Pat. No. 5,549,633, which is incorporated herein by reference in its entirety, described exemplary devices and methods for coupling a sealing material to a suture.

Reverse Flow System

Any of the embodiments of the suture closure devices discussed above may be used in combination with a retrograde flow system that may be used in conjunction with a variety of interventional procedures. Exemplary embodiments of a retrograde flow system and exemplary interventional procedures are now described. The system is sometimes described in the context of use with a carotid artery stenting procedure although it should be appreciated that the system can be used with various procedures not limited to carotid artery stenting.

Figure 20:
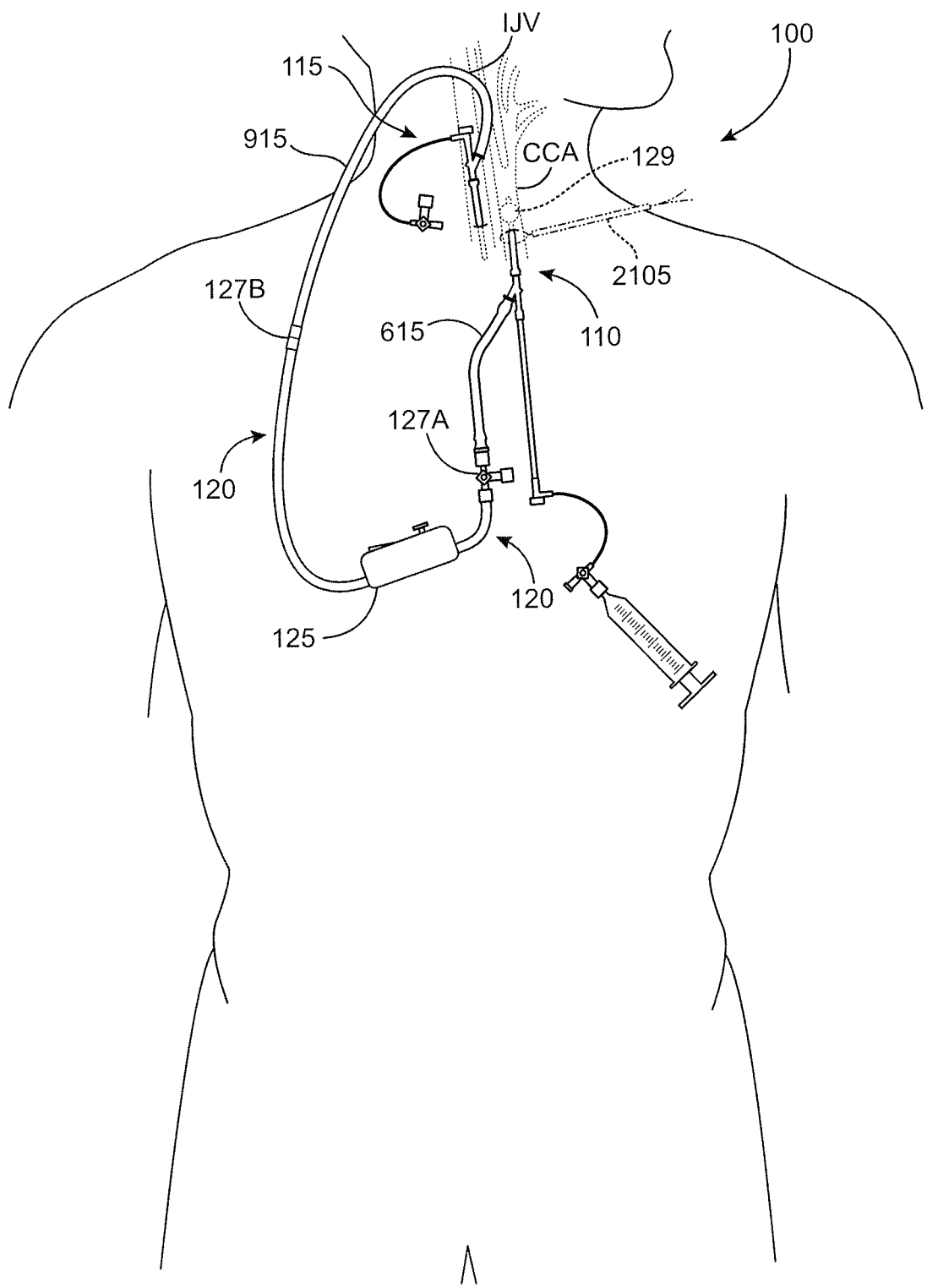
FIG. 20 shows a first embodiment of a retrograde flow system that is adapted to establish and facilitate retrograde or reverse flow blood circulation.

FIG. 20 shows a first embodiment of a retrograde flow system 100 that is adapted to establish and facilitate retrograde or reverse flow blood circulation in the region of the carotid artery bifurcation in order to limit or prevent the release of emboli into the cerebral vasculature, particularly into the internal carotid artery. The system 100 interacts with the carotid artery to provide retrograde flow from the carotid artery to a venous return site, such as the internal jugular vein (or to another return site such as another large vein or an external receptacle in alternate embodiments.) The retrograde flow system 100 includes an arterial access device 110, a venous return device 115, and a shunt 120 that provides a passageway for retrograde flow from the arterial access device 110 to the venous return device 115. A flow control assembly 125 interacts with the shunt 120. The flow control assembly 125 is adapted to regulate and/or monitor the retrograde flow from the common carotid artery to the internal jugular vein, as described in more detail below. The flow control assembly 125 interacts with the flow pathway through the shunt 120, either external to the flow path, inside the flow path, or both.

The arterial access device 110 at least partially inserts into the common carotid artery CCA and the venous return device 115 at least partially inserts into a venous return site such as the internal jugular vein IJV, as described in more detail below. The arterial access device 110 and the venous return device 115 couple to the shunt 120 at connection locations 127a and 127b. When flow through the common carotid artery is blocked, the natural pressure gradient between the internal carotid artery and the venous system causes blood to flow in a retrograde or reverse direction RG from the cerebral vasculature through the internal carotid artery and through the shunt 120 into the venous system. The flow control assembly 125 modulates, augments, assists, monitors, and/or otherwise regulates the retrograde blood flow.

In the embodiment of FIG. 20, the arterial access device 110 accesses the common carotid artery CCA via a transcervical approach. Transcervical access provides a short length and non-tortuous pathway from the vascular access point to the target treatment site thereby easing the time and difficulty of the procedure, compared for example to a transfemoral approach. Additionally, this access route reduces the risk of emboli generation from navigation of diseased, angulated, or tortuous aortic arch or common carotid artery anatomy. At least a portion of the venous return device 115 is placed in the internal jugular vein IJV. In an embodiment, transcervical access to the common carotid artery is achieved percutaneously via an incision or puncture in the skin through which the arterial access device 110 is inserted. If an incision is used, then the incision can be about 0.5 cm in length. An occlusion element 129, such as an expandable balloon, can be used to occlude the common carotid artery CCA at a location proximal of the distal end of the arterial access device 110. The occlusion element 129 can be located on the arterial access device 110 or it can be located on a separate device. In an alternate embodiment, the arterial access device 110 accesses the common carotid artery CCA via a direct surgical transcervical approach. In the surgical approach, the common carotid artery can be occluded using a tourniquet 2105. The tourniquet 2105 is shown in phantom to indicate that it is a device that is used in the optional surgical approach.

In another embodiment, shown in the arterial access device 110 accesses the common carotid artery CCA via a transcervical approach while the venous return device 115 access a venous return site other than the jugular vein, such as a venous return site comprised of the femoral vein FV. The venous return device 115 can be inserted into a central vein such as the femoral vein FV via a percutaneous puncture in the groin.

In another embodiment, the arterial access device 110 accesses the common carotid artery via a femoral approach. According to the femoral approach, the arterial access device 110 approaches the CCA via a percutaneous puncture into the femoral artery FA, such as in the groin, and up the aortic arch AA into the target common carotid artery CCA. The venous return device 115 can communicate with the jugular vein JV or the femoral vein FV.

In another embodiment the system provides retrograde flow from the carotid artery to an external receptacle 130 rather than to a venous return site. The arterial access device 110 connects to the receptacle 130 via the shunt 120, which communicates with the flow control assembly 125. The retrograde flow of blood is collected in the receptacle 130. If desired, the blood could be filtered and subsequently returned to the patient. The pressure of the receptacle 130 could be set at zero pressure (atmospheric pressure) or even lower, causing the blood to flow in a reverse direction from the cerebral vasculature to the receptacle 130. Optionally, to achieve or enhance reverse flow from the internal carotid artery, flow from the external carotid artery can be blocked, typically by deploying a balloon or other occlusion element in the external carotid artery just above the bifurcation with the internal carotid artery.

Detailed Description of Retrograde Blood Flow System

As discussed, the retrograde flow system 100 includes the arterial access device 110, venous return device 115, and shunt 120 which provides a passageway for retrograde flow from the arterial access device 110 to the venous return device 115. The system also includes the flow control assembly 125, which interacts with the shunt 120 to regulate and/or monitor retrograde blood flow through the shunt 120. Exemplary embodiments of the components of the retrograde flow system 100 are now described.

Arterial Access Device

FIG. 21A shows an exemplary embodiment of the arterial access device 110, which comprises a distal sheath 605, a proximal extension 610, a flow line 615, an adaptor or Y-connector 620, and a hemostasis valve 625. The distal sheath 605 is adapted to be introduced through an incision or puncture in a wall of a common carotid artery, either an open surgical incision or a percutaneous puncture established, for example, using the Seldinger technique. The length of the sheath can be in the range from 5 to 15 cm, usually being from 10 cm to 12 cm. The inner diameter is typically in the range from 7 Fr (1 Fr=0.33 mm), to 10 Fr, usually being 8 Fr. Particularly when the sheath is being introduced through the transcervical approach, above the clavicle but below the carotid bifurcation, it is desirable that the sheath 605 be highly flexible while retaining hoop strength to resist kinking and buckling. Thus, the distal sheath 605 can be circumferentially reinforced, such as by braid, helical ribbon, helical wire, or the like. In an alternate embodiment, the distal sheath is adapted to be introduced through a percutaneous puncture into the femoral artery, such as in the groin, and up the aortic arch AA into the target common carotid artery CCA The distal sheath 605 can have a stepped or other configuration having a reduced diameter distal region 630, as shown in FIG. 21B, which shows an enlarged view of the distal region 630 of the sheath 605. The distal region 630 of the sheath can be sized for insertion into the carotid artery, typically having an inner diameter in the range from 2.16 mm (0.085 inch) to 2.92 mm (0.115 inch) with the remaining proximal region of the sheath having larger outside and luminal diameters, with the inner diameter typically being in the range from 2.794 mm (0.110 inch) to 3.43 mm (0.135 inch). The larger luminal diameter of the proximal region minimizes the overall flow resistance of the sheath. In an embodiment, the reduced-diameter distal section 630 has a length of approximately 2 cm to 4 cm. The relatively short length of the reduced-diameter distal section 630 permits this section to be positioned in the common carotid artery CCA via the transcervical approach with reduced risk that the distal end of the sheath 605 will contact the bifurcation B. Moreover, the reduced diameter section 630 also permits a reduction in size of the arteriotomy for introducing the sheath 605 into the artery while having a minimal impact in the level of flow resistance.

With reference again to FIG. 21A, the proximal extension 610 has an inner lumen which is contiguous with an inner lumen of the sheath 605. The lumens can be joined by the Y-connector 620 which also connects a lumen of the flow line 615 to the sheath. In the assembled system, the flow line 615 connects to and forms a first leg of the retrograde shunt 120. The proximal extension 610 can have a length sufficient to space the hemostasis valve 625 well away from the Y-connector 620, which is adjacent to the percutaneous or surgical insertion site. By spacing the hemostasis valve 625 away from a percutaneous insertion site, the physician can introduce a stent delivery system or other working catheter into the proximal extension 610 and sheath 605 while staying out of the fluoroscopic field when fluoroscopy is being performed.

A flush line 635 can be connected to the side of the hemostasis valve 625 and can have a stopcock 640 at its proximal or remote end. The flush-line 635 allows for the introduction of saline, contrast fluid, or the like, during the procedures. The flush line 635 can also allow pressure monitoring during the procedure. A dilator 645 having a tapered distal end 650 can be provided to facilitate introduction of the distal sheath 605 into the common carotid artery. The dilator 645 can be introduced through the hemostasis valve 625 so that the tapered distal end 650 extends through the distal end of the sheath 605, as best seen in FIG. 22A. The dilator 645 can have a central lumen to accommodate a guide wire. Typically, the guide wire is placed first into the vessel, and the dilator/sheath combination travels over the guide wire as it is being introduced into the vessel.

Optionally, a tube 705 may be provided which is coaxially received over the exterior of the distal sheath 605, also as seen in FIG. 22A. The tube 705 has a flared proximal end 710 which engages the adapter 620 and a distal end 715. Optionally, the distal end 715 may be beveled, as shown in FIG. 22B. The tube 705 may serve at least two purposes. First, the length of the tube 705 limits the introduction of the sheath 605 to the exposed distal portion of the sheath 605, as seen in FIG. 22A. Second, the tube 705 can engage a pre-deployed puncture closure device disposed in the carotid artery wall, if present, to permit the sheath 605 to be withdrawn without dislodging the closure device.

The distal sheath 605 can be configured to establish a curved transition from a generally anterior-posterior approach over the common carotid artery to a generally axial luminal direction within the common carotid artery. The transition in direction is particularly useful when a percutaneous access is provided through the common carotid wall. While an open surgical access may allow for some distance in which to angle a straight sheath into the lumen of the common carotid artery, percutaneous access will generally be in a normal or perpendicular direction relative to the access of the lumen, and in such cases, a sheath that can flex or turn at an angle will find great use.

In an embodiment, the sheath 605 includes a retention feature that is adapted to retain the sheath within a blood vessel (such as the common carotid artery) into which the sheath 605 has been inserted. The retention features reduces the likelihood that the sheath 605 will be inadvertently pulled out of the blood vessel. In this regard, the retention feature interacts with the blood vessel to resist and/or eliminate undesired pull-out. In addition, the retention feature may also include additional elements that interact with the vessel wall to prevent the sheath from entering too far into the vessel. The retention feature may also include sealing elements which help seal the sheath against arterial blood pressure at the puncture site.

The sheath 605 can be formed in a variety of ways. For example, the sheath 605 can be pre-shaped to have a curve or an angle some set distance from the tip, typically 2 to 3 cm. The pre-shaped curve or angle can typically provide for a turn in the range from 20° to 90°, preferably from 30° to 70°. For initial introduction, the sheath 605 can be straightened with an obturator or other straight or shaped instrument such as the dilator 645 placed into its lumen. After the sheath 605 has been at least partially introduced through the percutaneous or other arterial wall penetration, the obturator can be withdrawn to allow the sheath 605 to reassume its pre-shaped configuration into the arterial lumen.

Other sheath configurations include having a deflection mechanism such that the sheath can be placed and the catheter can be deflected in situ to the desired deployment angle. In still other configurations, the catheter has a non-rigid configuration when placed into the lumen of the common carotid artery. Once in place, a pull wire or other stiffening mechanism can be deployed in order to shape and stiffen the sheath into its desired configuration. One particular example of such a mechanism is commonly known as "shape-lock" mechanisms as well described in medical and patent literature.

Another sheath configuration comprises a curved dilator inserted into a straight but flexible sheath, so that the dilator and sheath are curved during insertion. The sheath is flexible enough to conform to the anatomy after dilator removal.

In an embodiment, the sheath has built-in puncturing capability and atraumatic tip analogous to a guide wire tip. This eliminates the need for needle and wire exchange currently used for arterial access according to the micropuncture technique, and can thus save time, reduce blood loss, and require less surgeon skill.

FIG. 23A shows another embodiment of the arterial access device 110. This embodiment is substantially the same as the embodiment shown in FIG. 21A, except that the distal sheath 605 includes an occlusion element 129 for occluding flow through, for example the common carotid artery. If the occluding element 129 is an inflatable structure such as a balloon or the like, the sheath 605 can include an inflation lumen that communicates with the occlusion element 129. The occlusion element 129 can be an inflatable balloon, but it could also be an inflatable cuff, a conical or other circumferential element which flares outwardly to engage the interior wall of the common carotid artery to block flow therepast, a membrane-covered braid, a slotted tube that radially enlarges when axially compressed, or similar structure which can be deployed by mechanical means, or the like. In the case of balloon occlusion, the balloon can be compliant, non-compliant, elastomeric, reinforced, or have a variety of other characteristics. In an embodiment, the balloon is an elastomeric balloon which is closely received over the exterior of the distal end of the sheath prior to inflation. When inflated, the elastomeric balloon can expand and conform to the inner wall of the common carotid artery. In an embodiment, the elastomeric balloon is able to expand to a diameter at least twice that of the non-deployed configuration, frequently being able to be deployed to a diameter at least three times that of the undeployed configuration, more preferably being at least four times that of the undeployed configuration, or larger.

As shown in FIG. 23B, the distal sheath 605 with the occlusion element 129 can have a stepped or other configuration having a reduced diameter distal region 630. The distal region 630 can be sized for insertion into the carotid artery with the remaining proximal region of the sheath 605 having larger outside and luminal diameters, with the inner diameter typically being in the range from 2.794 mm (0.110 inch) to 3.43 mm (0.135 inch). The larger luminal diameter of the proximal region minimizes the overall flow resistance of the sheath. In an embodiment, the reduced-diameter distal section 630 has a length of approximately 2 cm to 4 cm. The relatively short length of the reduced-diameter distal section 630 permits this section to be positioned in the common carotid artery CCA via the transcervical approach with reduced risk that the distal end of the sheath 605 will contact the bifurcation B.

In an embodiment as shown in FIGS. 24 and 25, the proximal extension 610 is removably connected to the Y-arm connector 620 at a connection site. In this embodiment, an additional hemostasis valve 621 may be included at the connection site of the proximal extension 610 to the Y-arm connector 620, so that hemostasis is maintained when the proximal extension is not attached. FIG. 24 shows the arterial access sheath 605, with the proximal extension 610 attached to the Y-connector 620. FIG. 24 also shows an additional connection line 623 for balloon inflation of an occlusion element 129. FIG. 25 shows the proximal extension 610 removed from the Y-connector 620.

Venous Return Device

Figure 26:
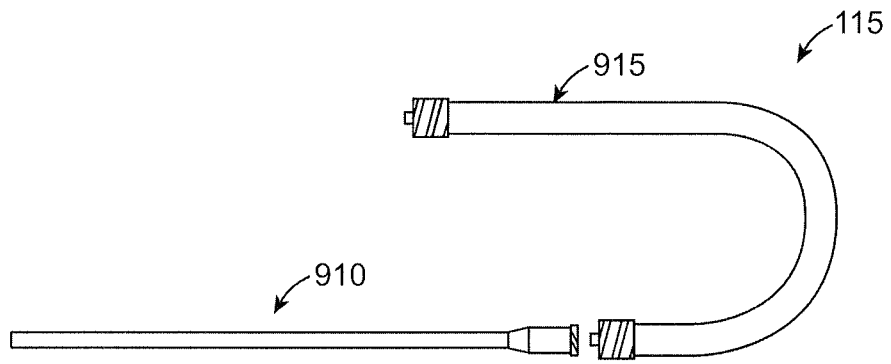
FIG. 26 illustrates a first embodiment of a venous return device useful in the methods and systems of the present disclosure.
Figure 27:
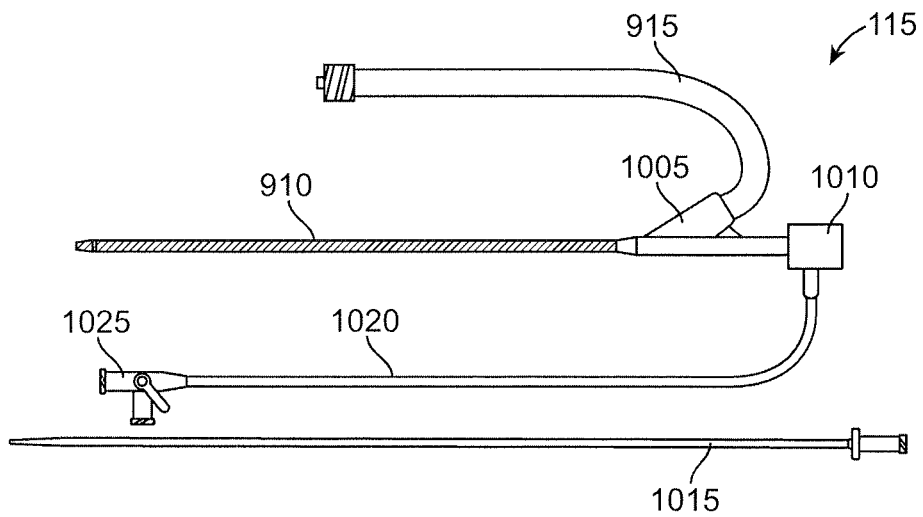
FIG. 27 illustrates an alternative venous return device useful in the methods and systems of the present disclosure.

Referring now to FIG. 26, the venous return device 115 can comprise a distal sheath 910 and a flow line 915, which connects to and forms a leg of the shunt 120 when the system is in use. The distal sheath 910 is adapted to be introduced through an incision or puncture into a venous return location, such as the jugular vein or femoral vein. The distal sheath 910 and flow line 915 can be permanently affixed, or can be attached using a conventional luer fitting, as shown in FIG. 26. Optionally, as shown in FIG. 27, the sheath 910 can be joined to the flow line 915 by a Y-connector 1005. The Y-connector 1005 can include a hemostasis valve 1010, permitting insertion of a dilator 1015 to facilitate introduction of the venous return device into the internal jugular vein or other vein. As with the arterial access dilator 645, the venous dilator 1015 includes a central guide wire lumen so the venous sheath and dilator combination can be placed over a guide wire. Optionally, the venous sheath 910 can include a flush line 1020 with a stopcock 1025 at its proximal or remote end.

In order to reduce the overall system flow resistance, the arterial access flow line 615 and the venous return flow line 915, and Y-connectors 620 and 1005, can each have a relatively large flow lumen inner diameter, typically being in the range from 2.54 mm (0.100 inch) to 5.08 mm (0.200 inch), and a relatively short length, typically being in the range from 10 cm to 20 cm. The low system flow resistance is desirable since it permits the flow to be maximized during portions of a procedure when the risk of emboli is at its greatest. The low system flow resistance also allows the use of a variable flow resistance for controlling flow in the system, as described in more detail below. The dimensions of the venous return sheath 910 can be generally the same as those described for the arterial access sheath 605 above. In the venous return sheath, an extension for the hemostasis valve 1010 is not required.

Retrograde Shunt

The shunt 120 can be formed of a single tube or multiple, connected tubes that provide fluid communication between the arterial access catheter 110 and the venous return catheter 115 to provide a pathway for retrograde blood flow therebetween. The shunt 120 connects at one end (via connector 127a) to the flow line 615 of the arterial access device 110, and at an opposite end (via connector 127b) to the flow line 915 of the venous return catheter 115.

In an embodiment, the shunt 120 can be formed of at least one tube that communicates with the flow control assembly 125. The shunt 120 can be any structure that provides a fluid pathway for blood flow. The shunt 120 can have a single lumen or it can have multiple lumens. The shunt 120 can be removably attached to the flow control assembly 125, arterial access device 110, and/or venous return device 115. Prior to use, the user can select a shunt 120 with a length that is most appropriate for use with the arterial access location and venous return location. In an embodiment, the shunt 120 can include one or more extension tubes that can be used to vary the length of the shunt 120. The extension tubes can be modularly attached to the shunt 120 to achieve a desired length. The modular aspect of the shunt 120 permits the user to lengthen the shunt 120 as needed depending on the site of venous return. For example, in some patients, the internal jugular vein IJV is small and/or tortuous. The risk of complications at this site may be higher than at some other locations, due to proximity to other anatomic structures. In addition, hematoma in the neck may lead to airway obstruction and/or cerebral vascular complications. Consequently, for such patients it may be desirable to locate the venous return site at a location other than the internal jugular vein IJV, such as the femoral vein. A femoral vein return site may be accomplished percutaneously, with lower risk of serious complication, and also offers an alternative venous access to the central vein if the internal jugular vein IJV is not available. Furthermore, the femoral venous return changes the layout of the reverse flow shunt such that the shunt controls may be located closer to the "working area" of the intervention, where the devices are being introduced and the contrast injection port is located.

In an embodiment, the shunt 120 has an internal diameter of 4.76 mm (3/16 inch) and has a length of 40-70 cm. As mentioned, the length of the shunt can be adjusted.

Flow Control Assembly—Regulation and Monitoring of Retrograde Flow

The flow control assembly 125 interacts with the retrograde shunt 120 to regulate and/or monitor the retrograde flow rate from the common carotid artery to the venous return site, such as the internal jugular vein, or to the external receptacle 130. In this regard, the flow control assembly 125 enables the user to achieve higher maximum flow rates than existing systems and to also selectively adjust, set, or otherwise modulate the retrograde flow rate. Various mechanisms can be used to regulate the retrograde flow rate, as described more fully below. The flow control assembly 125 enables the user to configure retrograde blood flow in a manner that is suited for various treatment regimens, as described below.

In general, the ability to control the continuous retrograde flow rate allows the physician to adjust the protocol for individual patients and stages of the procedure. The retrograde blood flow rate will typically be controlled over a range from a low rate to a high rate. The high rate can be at least two fold higher than the low rate, typically being at least three fold higher than the low rate, and often being at least five fold higher than the low rate, or even higher. In an embodiment, the high rate is at least three fold higher than the low rate and in another embodiment the high rate is at least six fold higher than the low rate. While it is generally desirable to have a high retrograde blood flow rate to maximize the extraction of emboli from the carotid arteries, the ability of patients to tolerate retrograde blood flow will vary. Thus, by having a system and protocol which allows the retrograde blood flow rate to be easily modulated, the treating physician can determine when the flow rate exceeds the tolerable level for that patient and set the reverse flow rate accordingly. For patients who cannot tolerate continuous high reverse flow rates, the physician can chose to turn on high flow only for brief, critical portions of the procedure when the risk of embolic debris is highest. At short intervals, for example between 15 seconds and 1 minute, patient tolerance limitations are usually not a factor.

In specific embodiments, the continuous retrograde blood flow rate can be controlled at a base line flow rate in the range from 10 ml/min to 200 ml/min, typically from 20 ml/min to 100 ml/min. These flow rates will be tolerable to the majority of patients. Although flow rate is maintained at the base line flow rate during most of the procedure, at times when the risk of emboli release is increased, the flow rate can be increased above the base line for a short duration in order to improve the ability to capture such emboli. For example, the retrograde blood flow rate can be increased above the base line when the stent catheter is being introduced, when the stent is being deployed, pre- and post-dilatation of the stent, removal of the common carotid artery occlusion, and the like.

The flow rate control system can be cycled between a relatively low flow rate and a relatively high flow rate in order to "flush" the carotid arteries in the region of the carotid bifurcation prior to reestablishing antegrade flow. Such cycling can be established with a high flow rate which can be approximately two to six fold greater than the low flow rate, typically being about three fold greater. The cycles can typically have a length in the range from 0.5 seconds to 10 seconds, usually from 2 seconds to 5 seconds, with the total duration of the cycling being in the range from 5 seconds to 60 seconds, usually from 10 seconds to 30 seconds.

Figure 28:
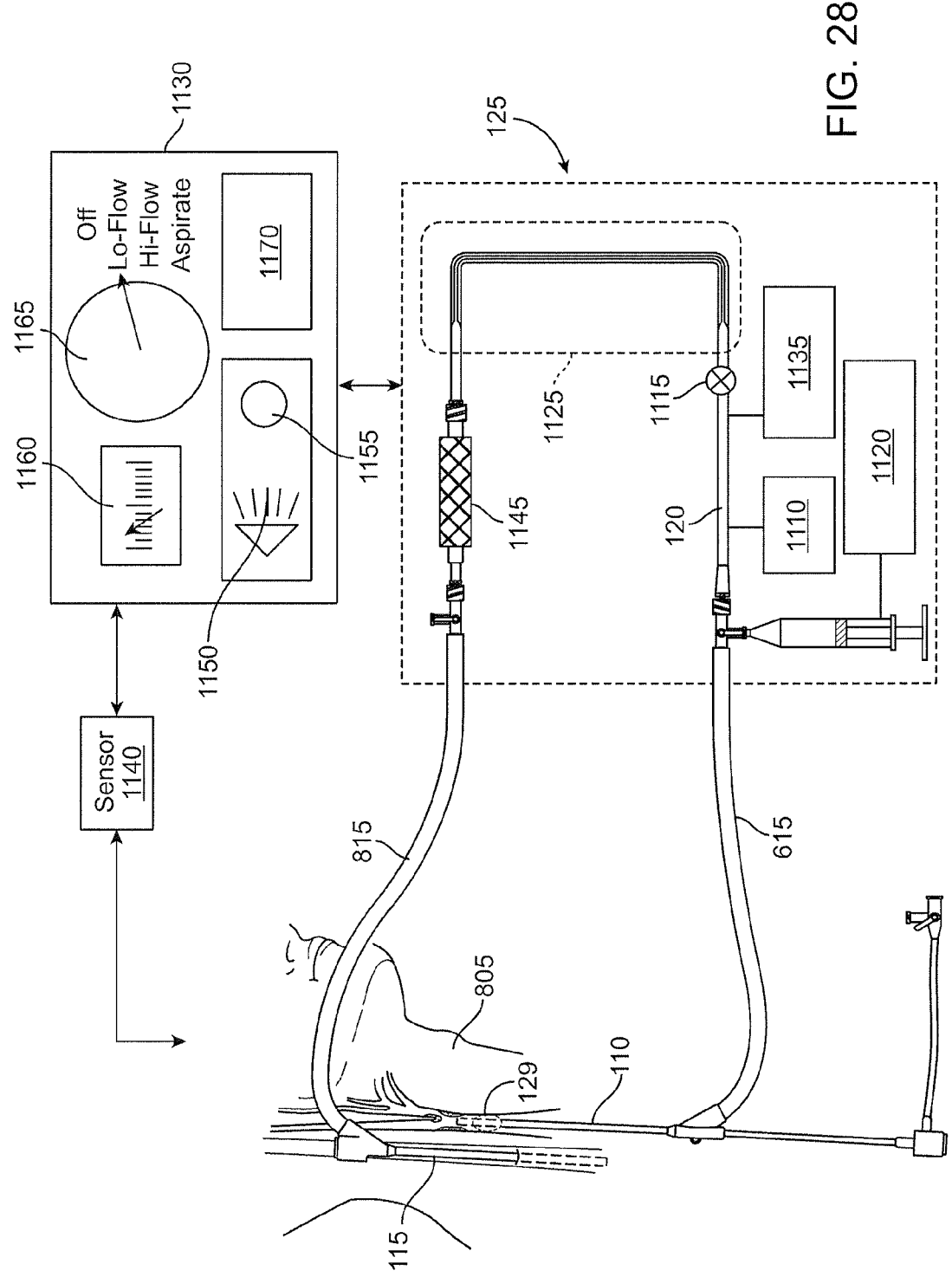
FIG. 28 illustrates the system of FIG. 20 including a flow control assembly.

FIG. 28 shows an example of the system 100 with a schematic representation of the flow control assembly 125, which is positioned along the shunt 120 such that retrograde blood flow passes through or otherwise communicates with at least a portion of the flow control assembly 125. The flow control assembly 125 can include various controllable mechanisms for regulating and/or monitoring retrograde flow. The mechanisms can include various means of controlling the retrograde flow, including one or more pumps 1110, valves 1115, syringes 1120 and/or a variable resistance component 1125. The flow control assembly 125 can be manually controlled by a user and/or automatically controlled via a controller 1130 to vary the flow through the shunt 120. For example, varying the flow resistance, the rate of retrograde blood flow through the shunt 120 can be controlled. The controller 1130, which is described in more detail below, can be integrated into the flow control assembly 125 or it can be a separate component that communicates with the components of the flow control assembly 125.

In addition, the flow control assembly 125 can include one or more flow sensors 1135 and/or anatomical data sensors 1140 (described in detail below) for sensing one or more aspects of the retrograde flow. A filter 1145 can be positioned along the shunt 120 for removing emboli before the blood is returned to the venous return site. When the filter 1145 is positioned upstream of the controller 1130, the filter 1145 can prevent emboli from entering the controller 1145 and potentially clogging the variable flow resistance component 1125. It should be appreciated that the various components of the flow control assembly 125 (including the pump 1110, valves 1115, syringes 1120, variable resistance component 1125, sensors 1135/1140, and filter 1145) can be positioned at various locations along the shunt 120 and at various upstream or downstream locations relative to one another. The components of the flow control assembly 125 are not limited to the locations shown in FIG. 28. Moreover, the flow control assembly 125 does not necessarily include all of the components but can rather include various sub-combinations of the components. For example, a syringe could optionally be used within the flow control assembly 125 for purposes of regulating flow or it could be used outside of the assembly for purposes other than flow regulation, such as to introduce fluid such as radiopaque contrast into the artery in an antegrade direction via the shunt 120.

Both the variable resistance component 1125 and the pump 1110 can be coupled to the shunt 120 to control the retrograde flow rate. The variable resistance component 1125 controls the flow resistance, while the pump 1110 provides for positive displacement of the blood through the shunt 120. Thus, the pump can be activated to drive the retrograde flow rather than relying on the perfusion stump pressures of the ECA and ICA and the venous back pressure to drive the retrograde flow. The pump 1110 can be a peristaltic tube pump or any type of pump including a positive displacement pump. The pump 1110 can be activated and deactivated (either manually or automatically via the controller 1130) to selectively achieve blood displacement through the shunt 120 and to control the flow rate through the shunt 120. Displacement of the blood through the shunt 120 can also be achieved in other manners including using the aspiration syringe 1120, or a suction source such as a vacutainer, vaculock syringe, or wall suction may be used. The pump 1110 can communicate with the controller 1130.

One or more flow control valves 1115 can be positioned along the pathway of the shunt. The valve(s) can be manually actuated or automatically actuated (via the controller 1130). The flow control valves 1115 can be, for example one-way valves to prevent flow in the antegrade direction in the shunt 120, check valves, or high pressure valves which would close off the shunt 120, for example during high-pressure contrast injections (which are intended to enter the arterial vasculature in an antegrade direction).

The controller 1130 communicates with components of the system 100 including the flow control assembly 125 to enable manual and/or automatic regulation and/or monitoring of the retrograde flow through the components of the system 100 (including, for example, the shunt 120, the arterial access device 110, the venous return device 115 and the flow control assembly 125). For example, a user can actuate one or more actuators on the controller 1130 to manually control the components of the flow control assembly 125. Manual controls can include switches or dials or similar components located directly on the controller 1130 or components located remote from the controller 1130 such as a foot pedal or similar device. The controller 1130 can also automatically control the components of the system 100 without requiring input from the user. In an embodiment, the user can program software in the controller 1130 to enable such automatic control. The controller 1130 can control actuation of the mechanical portions of the flow control assembly 125. The controller 1130 can include circuitry or programming that interprets signals generated by sensors 1135/1140 such that the controller 1130 can control actuation of the flow control assembly 125 in response to such signals generated by the sensors.

The representation of the controller 1130 in FIG. 28 is merely exemplary. It should be appreciated that the controller 1130 can vary in appearance and structure. The controller 1130 is shown in FIG. 28 as being integrated in a single housing. This permits the user to control the flow control assembly 125 from a single location. It should be appreciated that any of the components of the controller 1130 can be separated into separate housings. Further, FIG. 28 shows the controller 1130 and flow control assembly 125 as separate housings. It should be appreciated that the controller 1130 and flow control regulator 125 can be integrated into a single housing or can be divided into multiple housings or components.

Flow State Indicator(s)

The controller 1130 can include one or more indicators that provides a visual and/or audio signal to the user regarding the state of the retrograde flow. An audio indication advantageously reminds the user of a flow state without requiring the user to visually check the flow controller 1130. The indicator(s) can include a speaker 1150 and/or a light 1155 or any other means for communicating the state of retrograde flow to the user. The controller 1130 can communicate with one or more sensors of the system to control activation of the indicator. Or, activation of the indicator can be tied directly to the user actuating one of the flow control actuators 1165. The indicator need not be a speaker or a light. The indicator could simply be a button or switch that visually indicates the state of the retrograde flow. For example, the button being in a certain state (such as a pressed or down state) may be a visual indication that the retrograde flow is in a high state. Or, a switch or dial pointing toward a particular labeled flow state may be a visual indication that the retrograde flow is in the labeled state.

The indicator can provide a signal indicative of one or more states of the retrograde flow. In an embodiment, the indicator identifies only two discrete states: a state of "high" flow rate and a state of "low" flow rate. In another embodiment, the indicator identifies more than two flow rates, including a "high" flow rate, a "medium" flow rate, and a "low" rate. The indicator can be configured to identify any quantity of discrete states of the retrograde flow or it can identify a graduated signal that corresponds to the state of the retrograde flow. In this regard, the indicator can be a digital or analog meter 1160 that indicates a value of the retrograde flow rate, such as in ml/min or any other units.

In an embodiment, the indicator is configured to indicate to the user whether the retrograde flow rate is in a state of "high" flow rate or a "low" flow rate. For example, the indicator may illuminate in a first manner (e.g., level of brightness) and/or emit a first audio signal when the flow rate is high and then change to a second manner of illumination and/or emit a second audio signal when the flow rate is low. Or, the indicator may illuminate and/or emit an audio signal only when the flow rate is high, or only when the flow rate is low. Given that some patients may be intolerant of a high flow rate or intolerant of a high flow rate beyond an extended period of time, it can be desirable that the indicator provide notification to the user when the flow rate is in the high state. This would serve as a fail safe feature.

In another embodiment, the indicator provides a signal (audio and/or visual) when the flow rate changes state, such as when the flow rate changes from high to low and/or vice-versa. In another embodiment, the indicator provides a signal when no retrograde flow is present, such as when the shunt 120 is blocked or one of the stopcocks in the shunt 120 is closed.

Flow Rate Actuators

The controller 1130 can include one or more actuators that the user can press, switch, manipulate, or otherwise actuate to regulate the retrograde flow rate and/or to monitor the flow rate. For example, the controller 1130 can include a flow control actuator 1165 (such as one or more buttons, knobs, dials, switches, etc.) that the user can actuate to cause the controller to selectively vary an aspect of the reverse flow. For example, in the illustrated embodiment, the flow control actuator 1165 is a knob that can be turned to various discrete positions each of which corresponds to the controller 1130 causing the system 100 to achieve a particular retrograde flow state. The states include, for example, (a) OFF; (b) LO-FLOW; (c) HI-FLOW; and (d) ASPIRATE. It should be appreciated that the foregoing states are merely exemplary and that different states or combinations of states can be used. The controller 1130 achieves the various retrograde flow states by interacting with one or more components of the system, including the sensor(s), valve(s), variable resistance component, and/or pump(s). It should be appreciated that the controller 1130 can also include circuitry and software that regulates the retrograde flow rate and/or monitors the flow rate such that the user wouldn't need to actively actuate the controller 1130.

The OFF state corresponds to a state where there is no retrograde blood flow through the shunt 120. When the user sets the flow control actuator 1165 to OFF, the controller 1130 causes the retrograde flow to cease, such as by shutting off valves or closing a stop cock in the shunt 120. The LO-FLOW and HI-FLOW states correspond to a low retrograde flow rate and a high retrograde flow rate, respectively. When the user sets the flow control actuator 1165 to LO-FLOW or HI-FLOW, the controller 1130 interacts with components of the flow control regulator 125 including pump(s) 1110, valve(s) 1115 and/or variable resistance component 1125 to increase or decrease the flow rate accordingly. Finally, the ASPIRATE state corresponds to opening the circuit to a suction source, for example a vacutainer or suction unit, if active retrograde flow is desired.

The system can be used to vary the blood flow between various states including an active state, a passive state, an aspiration state, and an off state. The active state corresponds to the system using a means that actively drives retrograde blood flow. Such active means can include, for example, a pump, syringe, vacuum source, etc. The passive state corresponds to when retrograde blood flow is driven by the perfusion stump pressures of the ECA and ICA and possibly the venous pressure. The aspiration state corresponds to the system using a suction source, for example a vacutainer or suction unit, to drive retrograde blood flow. The off state corresponds to the system having zero retrograde blood flow such as the result of closing a stopcock or valve. The low and high flow rates can be either passive or active flow states. In an embodiment, the particular value (such as in ml/min) of either the low flow rate and/or the high flow rate can be predetermined and/or pre-programmed into the controller such that the user does not actually set or input the value. Rather, the user simply selects "high flow" and/or "low flow" (such as by pressing an actuator such as a button on the controller 1130) and the controller 1130 interacts with one or more of the components of the flow control assembly 125 to cause the flow rate to achieve the predetermined high or low flow rate value. In another embodiment, the user sets or inputs a value for low flow rate and/or high flow rate such as into the controller. In another embodiment, the low flow rate and/or high flow rate is not actually set. Rather, external data (such as data from the anatomical data sensor 1140) is used as the basis for affects the flow rate.

The flow control actuator 1165 can be multiple actuators, for example one actuator, such as a button or switch, to switch state from LO-FLOW to HI-FLOW and another to close the flow loop to OFF, for example during a contrast injection where the contrast is directed antegrade into the carotid artery. In an embodiment, the flow control actuator 1165 can include multiple actuators. For example, one actuator can be operated to switch flow rate from low to high, another actuator can be operated to temporarily stop flow, and a third actuator (such as a stopcock) can be operated for aspiration using a syringe. In another example, one actuator is operated to switch to LO-FLOW and another actuator is operated to switch to HI-FLOW. Or, the flow control actuator 1165 can include multiple actuators to switch states from LO-FLOW to HI-FLOW and additional actuators for fine-tuning flow rate within the high flow state and low flow state. Upon switching between LO-FLOW and HI-FLOW, these additional actuators can be used to fine-tune the flow rates within those states. Thus, it should be appreciated that within each state (i.e. high flow state and low flow states) a variety of flow rates can be dialed in and fine-tuned. A wide variety of actuators can be used to achieve control over the state of flow.

The controller 1130 or individual components of the controller 1130 can be located at various positions relative to the patient and/or relative to the other components of the system 100. For example, the flow control actuator 1165 can be located near the hemostasis valve where any interventional tools are introduced into the patient in order to facilitate access to the flow control actuator 1165 during introduction of the tools. The location may vary, for example, based on whether a transfemoral or a transcervical approach is used. The controller 1130 can have a wireless connection to the remainder of the system 100 and/or a wired connection of adjustable length to permit remote control of the system 100. The controller 1130 can have a wireless connection with the flow control regulator 125 and/or a wired connection of adjustable length to permit remote control of the flow control regulator 125. The controller 1130 can also be integrated in the flow control regulator 125. Where the controller 1130 is mechanically connected to the components of the flow control assembly 125, a tether with mechanical actuation capabilities can connect the controller 1130 to one or more of the components. In an embodiment, the controller 1130 can be positioned a sufficient distance from the system 100 to permit positioning the controller 1130 outside of a radiation field when fluoroscopy is in use.

The controller 1130 and any of its components can interact with other components of the system (such as the pump(s), sensor(s), shunt, etc) in various manners. For example, any of a variety of mechanical connections can be used to enable communication between the controller 1130 and the system components. Alternately, the controller 1130 can communicate electronically or magnetically with the system components. Electro-mechanical connections can also be used. The controller 1130 can be equipped with control software that enables the controller to implement control functions with the system components. The controller itself can be a mechanical, electrical or electro-mechanical device. The controller can be mechanically, pneumatically, or hydraulically actuated or electromechanically actuated (for example in the case of solenoid actuation of flow control state). The controller 1130 can include a computer, computer processor, and memory, as well as data storage capabilities.

Sensor(s)

As mentioned, the flow control assembly 125 can include or interact with one or more sensors, which communicate with the system 100 and/or communicate with the patient's anatomy. Each of the sensors can be adapted to respond to a physical stimulus (including, for example, heat, light, sound, pressure, magnetism, motion, etc.) and to transmit a resulting signal for measurement or display or for operating the controller 1130. In an embodiment, the flow sensor 1135 interacts with the shunt 120 to sense an aspect of the flow through the shunt 120, such as flow velocity or volumetric rate of blood flow. The flow sensor 1135 could be directly coupled to a display that directly displays the value of the volumetric flow rate or the flow velocity. Or the flow sensor 1135 could feed data to the controller 1130 for display of the volumetric flow rate or the flow velocity.

The type of flow sensor 1135 can vary. The flow sensor 1135 can be a mechanical device, such as a paddle wheel, flapper valve, rolling ball, or any mechanical component that responds to the flow through the shunt 120. Movement of the mechanical device in response to flow through the shunt 120 can serve as a visual indication of fluid flow and can also be calibrated to a scale as a visual indication of fluid flow rate. The mechanical device can be coupled to an electrical component. For example, a paddle wheel can be positioned in the shunt 120 such that fluid flow causes the paddle wheel to rotate, with greater rate of fluid flow causing a greater speed of rotation of the paddle wheel. The paddle wheel can be coupled magnetically to a Hall-effect sensor to detect the speed of rotation, which is indicative of the fluid flow rate through the shunt 120.

In an embodiment, the flow sensor 1135 is an ultrasonic or electromagnetic flow meter, which allows for blood flow measurement without contacting the blood through the wall of the shunt 120. An ultrasonic or electromagnetic flow meter can be configured such that it does not have to contact the internal lumen of the shunt 120. In an embodiment, the flow sensor 1135 at least partially includes a Doppler flow meter, such as a Transonic flow meter, that measures fluid flow through the shunt 120. It should be appreciated that any of a wide variety of sensor types can be used including an ultrasound flow meter and transducer. Moreover, the system can include multiple sensors.

The system 100 is not limited to using a flow sensor 1135 that is positioned in the shunt 120 or a sensor that interacts with the venous return device 115 or the arterial access device 110. For example, an anatomical data sensor 1140 can communicate with or otherwise interact with the patient's anatomy such as the patient's neurological anatomy. In this manner, the anatomical data sensor 1140 can sense a measurable anatomical aspect that is directly or indirectly related to the rate of retrograde flow from the carotid artery. For example, the anatomical data sensor 1140 can measure blood flow conditions in the brain, for example the flow velocity in the middle cerebral artery, and communicate such conditions to a display and/or to the controller 1130 for adjustment of the retrograde flow rate based on predetermined criteria. In an embodiment, the anatomical data sensor 1140 comprises a transcranial Doppler ultrasonography (TCD), which is an ultrasound test that uses reflected sound waves to evaluate blood as it flows through the brain. Use of TCD results in a TCD signal that can be communicated to the controller 1130 for controlling the retrograde flow rate to achieve or maintain a desired TCD profile. The anatomical data sensor 1140 can be based on any physiological measurement, including reverse flow rate, blood flow through the middle cerebral artery, TCD signals of embolic particles, or other neuromonitoring signals.

In an embodiment, the system 100 comprises a closed-loop control system. In the closed-loop control system, one or more of the sensors (such as the flow sensor 1135 or the anatomical data sensor 1140) senses or monitors a predetermined aspect of the system 100 or the anatomy (such as, for example, reverse flow rate and/or neuromonitoring signal). The sensor(s) feed relevant data to the controller 1130, which continuously adjusts an aspect of the system as necessary to maintain a desired retrograde flow rate. The sensors communicate feedback on how the system 100 is operating to the controller 1130 so that the controller 1130 can translate that data and actuate the components of the flow control regulator 125 to dynamically compensate for disturbances to the retrograde flow rate. For example, the controller 1130 may include software that causes the controller 1130 to signal the components of the flow control assembly 125 to adjust the flow rate such that the flow rate is maintained at a constant state despite differing blood pressures from the patient. In this embodiment, the system 100 need not rely on the user to determine when, how long, and/or what value to set the reverse flow rate in either a high or low state. Rather, software in the controller 1130 can govern such factors. In the closed loop system, the controller 1130 can control the components of the flow control assembly 125 to establish the level or state of retrograde flow (either analog level or discreet state such as high, low, baseline, medium, etc.) based on the retrograde flow rate sensed by the sensor 1135.

In an embodiment, the anatomical data sensor 1140 (which measures a physiologic measurement in the patient) communicates a signal to the controller 1130, which adjusts the flow rate based on the signal. For example the physiological measurement may be based on flow velocity through the MCA, TCD signal, or some other cerebral vascular signal. In the case of the TCD signal, TCD may be used to monitor cerebral flow changes and to detect microemboli. The controller 1130 may adjust the flow rate to maintain the TCD signal within a desired profile. For example, the TCD signal may indicate the presence of microemboli ("TCD hits") and the controller 1130 can adjust the retrograde flow rate to maintain the TCD hits below a threshold value of hits. (See, Ribo, et al., "Transcranial Doppler Monitoring of Transcervical Carotid Stenting with Flow Reversal Protection: A Novel Carotid Revascularization Technique", *Stroke* 2006, 37, 2846-2849; Shekel, et al., "Experience of 500 Cases of Neurophysiological Monitoring in Carotid Endarterectomy", *Acta Neurochir*, 2007, 149:681-689, which are incorporated by reference in their entirety.

In the case of the MCA flow, the controller 1130 can set the retrograde flow rate at the "maximum" flow rate that is tolerated by the patient, as assessed by perfusion to the brain. The controller 1130 can thus control the reverse flow rate to optimize the level of protection for the patient without relying on the user to intercede. In another embodiment, the feedback is based on a state of the devices in the system 100 or the interventional tools being used. For example, a sensor may notify the controller 1130 when the system 100 is in a high risk state, such as when an interventional catheter is positioned in the sheath 605. The controller 1130 then adjusts the flow rate to compensate for such a state.

The controller 1130 can be used to selectively augment the retrograde flow in a variety of manners. For example, it has been observed that greater reverse flow rates may cause a resultant greater drop in blood flow to the brain, most importantly the ipsilateral MCA, which may not be compensated enough with collateral flow from the Circle of Willis. Thus a higher reverse flow rate for an extended period of time may lead to conditions where the patient's brain is not getting enough blood flow, leading to patient intolerance as exhibited by neurologic symptoms. Studies show that MCA blood velocity less than 10 cm/sec is a threshold value below which patient is at risk for neurological blood deficit. There are other markers for monitoring adequate perfusion to the brains, such as EEG signals. However, a high flow rate may be tolerated even up to a complete stoppage of MCA flow for a short period, up to about 15 seconds to 1 minute.

Thus, the controller 1130 can optimize embolic debris capture by automatically increasing the reverse flow only during limited time periods which correspond to periods of heightened risk of emboli generation during a procedure. These periods of heightened risk include the period of time while an interventional device (such as a dilatation balloon for pre or post stenting dilatation or a stent delivery device) crosses the plaque P. Another period is during an interventional maneuver such as deployment of the stent or inflation and deflation of the balloon pre- or post-dilatation. A third period is during injection of contrast for angiographic imaging of treatment area. During lower risk periods, the controller can cause the reverse flow rate to revert to a lower, baseline level. This lower level may correspond to a low reverse flow rate in the ICA, or even slight antegrade flow in those patients with a high ECA to ICA perfusion pressure ratio.

In a flow regulation system where the user manually sets the state of flow, there is risk that the user may not pay attention to the state of retrograde flow (high or low) and accidentally keep the circuit on high flow. This may then lead to adverse patient reactions. In an embodiment, as a safety mechanism, the default flow rate is the low flow rate. This serves as a fail safe measure for patient's that are intolerant of a high flow rate. In this regard, the controller 1130 can be biased toward the default rate such that the controller causes the system to revert to the low flow rate after passage of a predetermined period of time of high flow rate. The bias toward low flow rate can be achieved via electronics or software, or it can be achieved using mechanical components, or a combination thereof. In an embodiment, the flow control actuator 1165 of the controller 1130 and/or valve(s) 1115 and/or pump(s) 1110 of the flow control regulator 125 are spring loaded toward a state that achieves a low flow rate. The controller 1130 is configured such that the user may over-ride the controller 1130 such as to manually cause the system to revert to a state of low flow rate if desired.

In another safety mechanism, the controller 1130 includes a timer 1170 (FIG. 28) that keeps time with respect to how long the flow rate has been at a high flow rate. The controller 1130 can be programmed to automatically cause the system 100 to revert to a low flow rate after a predetermined time period of high flow rate, for example after 15, 30, or 60 seconds or more of high flow rate. After the controller reverts to the low flow rate, the user can initiate another predetermined period of high flow rate as desired. Moreover, the user can override the controller 1130 to cause the system 100 to move to the low flow rate (or high flow rate) as desired.

In an exemplary procedure, embolic debris capture is optimized while not causing patient tolerance issues by initially setting the level of retrograde flow at a low rate, and then switching to a high rate for discreet periods of time during critical stages in the procedure. Alternately, the flow rate is initially set at a high rate, and then verifying patient tolerance to that level before proceeding with the rest of the procedure. If the patient shows signs of intolerance, the retrograde flow rate is lowered. Patient tolerance may be determined automatically by the controller based on feedback from the anatomical data sensor 1140 or it may be determined by a user based on patient observation. The adjustments to the retrograde flow rate may be performed automatically by the controller or manually by the user. Alternately, the user may monitor the flow velocity through the middle cerebral artery (MCA), for example using TCD, and then to set the maximum level of reverse flow which keeps the MCA flow velocity above the threshold level. In this situation, the entire procedure may be done without modifying the state of flow. Adjustments may be made as needed if the MCA flow velocity changes during the course of the procedure, or the patient exhibits neurologic symptoms.

Exemplary Mechanisms to Regulate Flow

The system 100 is adapted to regulate retrograde flow in a variety of manners. Any combination of the pump 1110, valve 1115, syringe 1120, and/or variable resistance component 1125 can be manually controlled by the user or automatically controlled via the controller 1130 to adjust the retrograde flow rate. Thus, the system 100 can regulate retrograde flow in various manners, including controlling an active flow component (e.g., pump, syringe, etc.), reducing the flow restriction, switching to an aspiration source (such as a pre-set VacLock syringe, Vacutainer, suction system, or the like), or any combination thereof.

In the situation where an external receptacle or reservoir is used, the retrograde flow may be augmented in various manners. The reservoir has a head height comprised of the height of the blood inside the reservoir and the height of the reservoir with respect to the patient. Reverse flow into the reservoir may be modulated by setting the reservoir height to increase or decrease the amount of pressure gradient from the CCA to the reservoir. In an embodiment, the reservoir is raised to increase the reservoir pressure to a pressure that is greater than venous pressure. Or, the reservoir can be positioned below the patient, such as down to a level of the floor, to lower the reservoir pressure to a pressure below venous or atmospheric pressure.

The variable flow resistance in shunt 120 may be provided in a wide variety of ways. In this regard, flow resistance component 1125 can cause a change in the size or shape of the shunt to vary flow conditions and thereby vary the flow rate. Or, the flow resistance component 1125 can re-route the blood flow through one or more alternate flow pathways in the shunt to vary the flow conditions. Some exemplary embodiments of the flow resistance component 1125 are now described.

As shown in FIGS. 29A, 29B, 29C, and 29D, in an embodiment the shunt 120 has an inflatable bladder 1205 formed along a portion of its interior lumen. As shown in FIGS. 29A and 29C, when the bladder 1205 is deflated, the inner lumen of the shunt 120 remains substantially unrestricted, providing for a low resistance flow. By inflating the bladder 1205, however, as shown in FIGS. 29B and 29D, the flow lumen can be greatly restricted, thus greatly increasing the flow resistance and reducing the flow rate of atrial blood to the venous vasculature. The controller 1130 can control inflation/deflation of the bladder 1205 or it can be controlled manually by the user.

Rather than using an inflatable internal bladder, as shown in FIGS. 29A-29D, the cross-sectional area of the lumen in the shunt 120 may be decreased by applying an external force, such as flattening the shunt 120 with a pair of opposed plates 1405, as shown in FIGS. 30A-30D. The opposed plates are adapted to move toward and away from one another with the shunt 120 positioned between the plates. When the plates 1405 are spaced apart, as shown in FIGS. 30A and 30C, the lumen of the shunt 120 remains unrestricted. When the plates 1405 are closed on the shunt 120, as shown in FIGS. 30B and 30D, in contrast, the plates 1405 constrict the shunt 120. In this manner, the lumen remaining in shunt 120 can be greatly decreased to increase flow resistance through the shunt. The controller 1130 can control movement of the plates 1405 or such movement can be controlled manually by the user.

Referring now to FIGS. 31A and 31B, the available cross-sectional area of the shunt 120 can also be restricted by axially elongating a portion 1505 of the shunt 120. Prior to axial elongation, the portion 1505 will be generally unchanged, providing a full luminal flow area in the portion 1505, as shown in FIG. 31A. By elongating the portion 1505, however, as shown in FIG. 31B, the internal luminal area of the shunt 120 in the portion 1505 can be significantly decreased and the length increased, both of which have the effect of increasing the flow resistance. When employing axial elongation to reduce the luminal area of shunt 120, it will be advantageous to employ a mesh or braid structure in the shunt at least in the portion 1505. The mesh or braid structure provides the shunt 120 with a pliable feature that facilitates axial elongation without breaking. The controller 1130 can control elongation of the shunt 120 or such it can be controlled manually by the user.

Referring now to FIGS. 32A-32D, instead of applying an external force to reduce the cross-sectional area of shunt 120, a portion of the shunt 120 can be made with a small diameter to begin with, as shown in FIGS. 32A and 32C. The shunt 120 passes through a chamber 1600 which is sealed at both ends. A vacuum is applied within the chamber 1600 exterior of the shunt 120 to cause a pressure gradient. The pressure gradient cause the shunt 120 to increase in size within the chamber 120, as shown in FIGS. 32B and 32D. The vacuum may be applied in a receptacle 1605 attached to a vacuum source 1610. Conversely, a similar system may be employed with a shunt 120 whose resting configuration is in the increased size. Pressure may be applied to the chamber to shrink or flatten the shunt to decrease the flow resistance. The controller 1130 can control the vacuum or it can be controlled manually by the user.

Figure 33A:
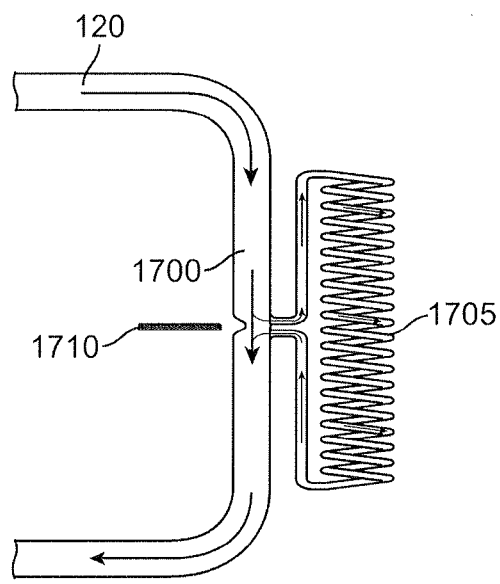
Figure 33B:
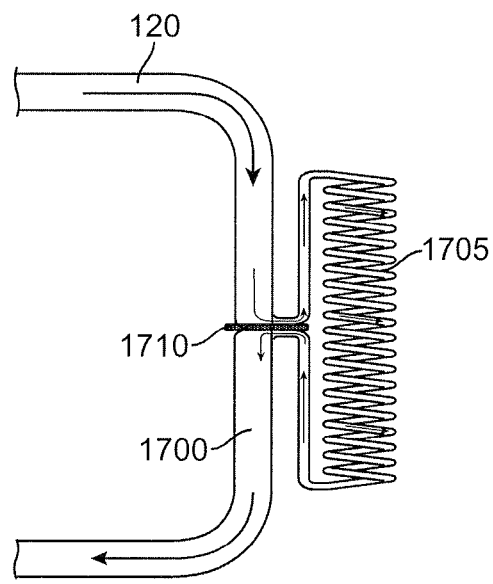

As yet another alternative, the flow resistance through shunt 120 may be changed by providing two or more alternative flow paths. As shown in FIG. 33A, the flow through shunt 120 passes through a main lumen 1700 as well as secondary lumen 1705. The secondary lumen 1705 is longer and/or has a smaller diameter than the main lumen 1700. Thus, the secondary lumen 1705 has higher flow resistance than the main lumen 1700. By passing the blood through both these lumens, the flow resistance will be at a minimum. Blood is able to flow through both lumens 1700 and 1705 due to the pressure drop created in the main lumen 1700 across the inlet and outlet of the secondary lumen 1705. This has the benefit of preventing stagnant blood. As shown in FIG. 33B, by blocking flow through the main lumen 1700 of shunt 120, the flow can be diverted entirely to the secondary lumen 1705, thus increasing the flow resistance and reducing the blood flow rate. It will be appreciated that additional flow lumens could also be provided in parallel to allow for a three, four, or more discrete flow resistances. The shunt 120 may be equipped with a valve 1710 that controls flow to the main lumen 1700 and the secondary lumen 1705 with the valve 1710 being controlled by the controller 1130 or being controlled manually by the user. The embodiment of FIGS. 33A and 33B has an advantage in that this embodiment in that it does not require as small of lumen sizes to achieve desired retrograde flow rates as some of the other embodiments of variable flow resistance mechanisms. This is a benefit in blood flow lines in that there is less chance of clogging and causing clots in larger lumen sizes than smaller lumen sizes.

Figure 34A:
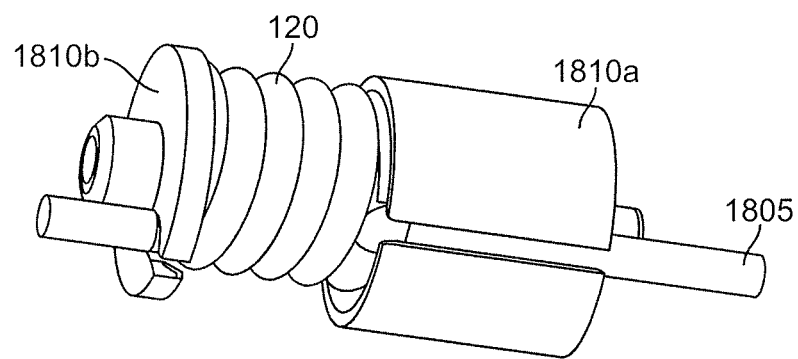
FIGS. 34A-34B, FIGS. 35A-35B, FIGS. 36A-36D, and FIGS. 37A-37B illustrate further embodiments of a variable flow resistance system useful in the methods and systems of the present disclosure.
Figure 34B:
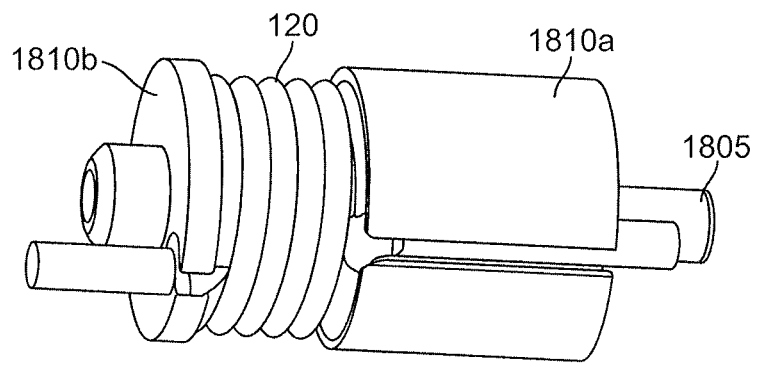

The shunt 120 can also be arranged in a variety of coiled configurations which permit external compression to vary the flow resistance in a variety of ways. Arrangement of a portion of the shunt 120 in a coil contains a long section of the shunt in a relatively small area. This allows compression of a long length of the shunt 120 over a small space. As shown in FIGS. 34A and 33B, a portion of the shunt 120 is wound around a dowel 1805 to form a coiled region. The dowel 1805 has plates 1810a and 1810b which can move toward and away from each other in an axial direction. When plates 1810a and 1810b are moved away from each other, the coiled portion of the shunt 105 is uncompressed and flow resistance is at a minimum. The shunt 120 is large diameter, so when the shunt is non-compressed, the flow resistance is low, allowing a high-flow state. To down-regulate the flow, the two plates 1810a and 1810b are pushed together, compressing the coil of shunt 120. By moving the plates 1810a and 1810b together, as shown in FIG. 34B, the coiled portion of the shunt 120 is compressed to increase the flow resistance. The controller 1130 can control the plates or they can be controlled manually by the user.

Figure 35A:
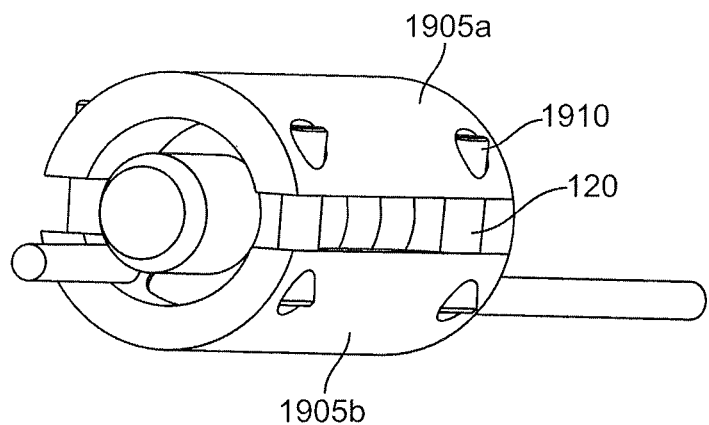
Figure 35B:
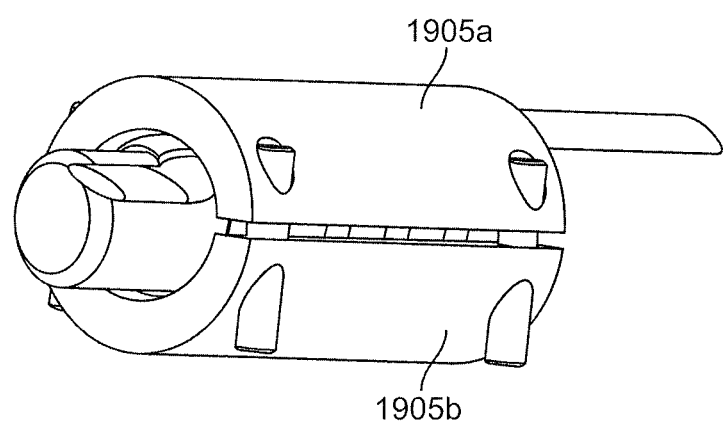

A similar compression apparatus is shown in FIGS. 35A and 35B. In this configuration, the coiled shunt 120 is encased between two movable cylinder halves 1905a and 1905b. The halves 1905a and 1905b can slide along dowel pins 1910 to move toward and away from one another. When the cylinder halves 1905 are moved apart, the coiled shunt 120 is uncompressed and flow resistance is at a minimum. When the cylinder halves 1905 are brought together, the coiled shunt 120 is compressed circumferentially to increase flow resistance. The controller 1130 can control the halves 1905 or they can be controlled manually by the user.

Figure 36C:
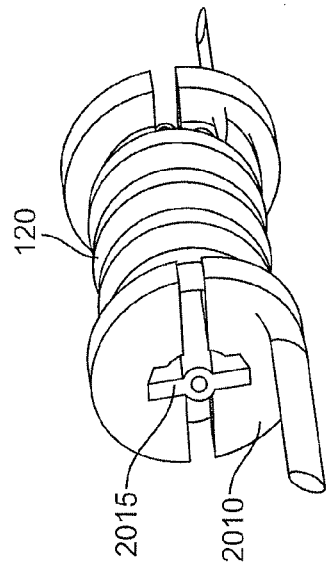
Figure 36D:
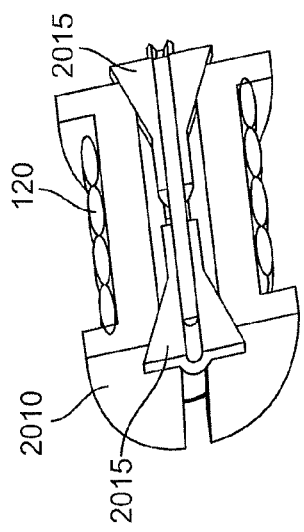
Figure 36A:
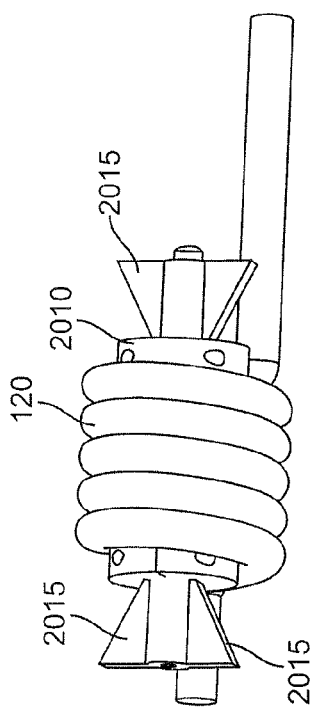
Figure 36B:
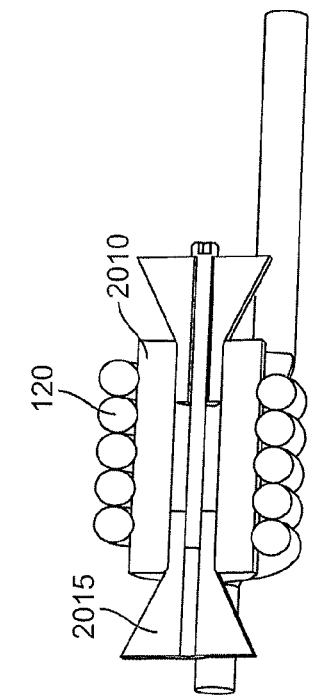

As shown in FIGS. 36A through 36D, the shunt 120 may also be wound around an axially split mandrel 2010 having wedge elements 2015 on opposed ends. By axially translating wedge elements 2015 in and out of the split mandrel 2010, the split portions of the mandrel are opened and closed relative to one another, causing the coil of tubing to be stretched (when the mandrel portions 2010 are spread apart, FIG. 36C, 36D) or relaxed (when the mandrel portions 2010 are closed, FIG. 36A, 36B.) Thus, when the wedge elements 2015 are spaced apart, as shown in FIGS. 36A and 36B, the outward pressure on the shunt 120 is at a minimum and the flow resistance is also at a minimum. By driving the wedge elements 2015 inwardly, as shown in FIGS. 36C and 36D, the split mandrel halves 2020 are forced apart and the coil of shunt 120 is stretched. This has the dual effect of decreasing the cross sectional area of the shunt and lengthening the shunt in the coiled region, both of which lead to increased flow resistance.

Figure 37A:
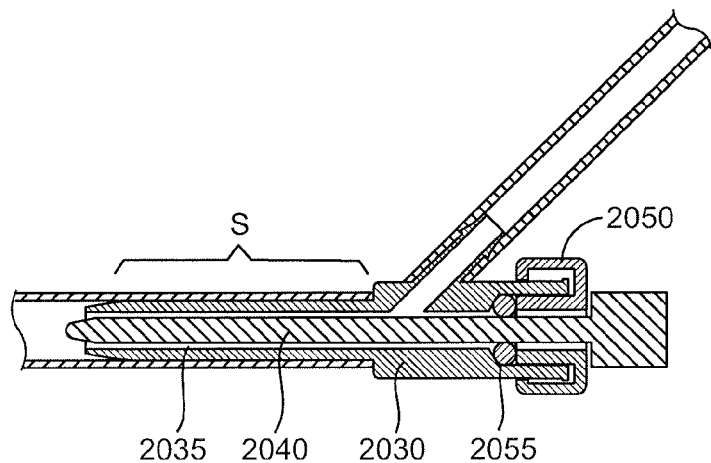
Figure 37B:
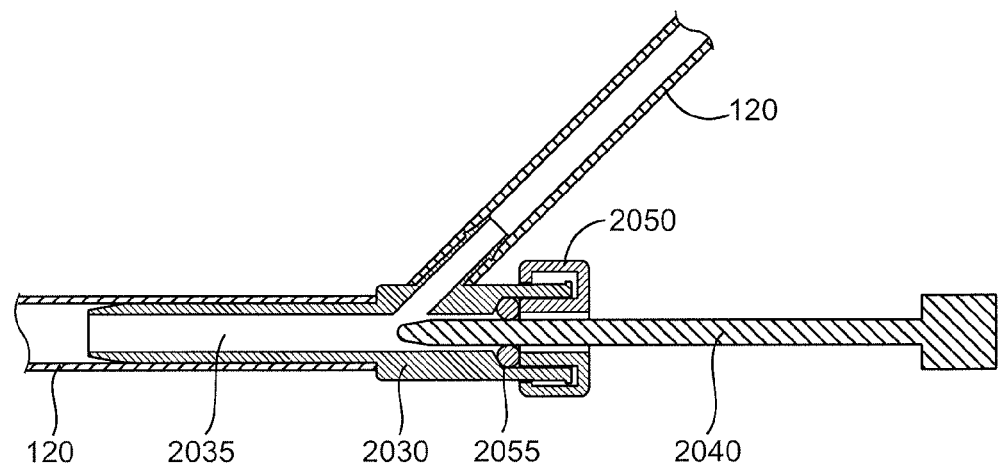

FIGS. 37A and 37B show an embodiment of the variable resistance component 1125 that uses a dowel to vary the resistance to flow. A housing 2030 is inserted into a section of the shunt 120. The housing 2030 has an internal lumen 2035 that is contiguous with the internal lumen of the shunt 120. A dowel 2040 can move into and out of a portion of the internal lumen 2035. As shown in FIG. 37A, when the dowel 2040 is inserted into the internal lumen 2035, the internal lumen 2035 is annular with a cross-sectional area that is much smaller than the cross-sectional area of the internal lumen 2035 when the dowel is not present. Thus, flow resistance increases when the dowel 2040 is positioned in the internal lumen 2035. The annular internal lumen 2035 has a length S that can be varied by varying the portion of the dowel 2040 that is inserted into the lumen 2035. Thus, as more of the dowel 2040 is inserted, the length S of the annular lumen 2035 increases and vice-versa. This can be used to vary the level of flow resistance caused by the presence of the dowel 2040.

The dowel 2040 enters the internal lumen 2035 via a hemostasis valve in the housing 2030. A cap 2050 and an O-ring 2055 provide a sealing engagement that seals the housing 2030 and dowel 2040 against leakage. The cap 2050 may have a locking feature, such as threads, that can be used to lock the cap 2050 against the housing 2030 and to also fix the position of the dowel 2040 in the housing 2040. When the cap 2050 is locked or tightened, the cap 2050 exerts pressure against the O-ring 2055 to tighten it against the dowel 2040 in a sealed engagement. When the cap 2050 is unlocked or untightened, the dowel 2040 is free to move in and out of the housing 2030.

Exemplary Intervention Procedure

Figure 38A:
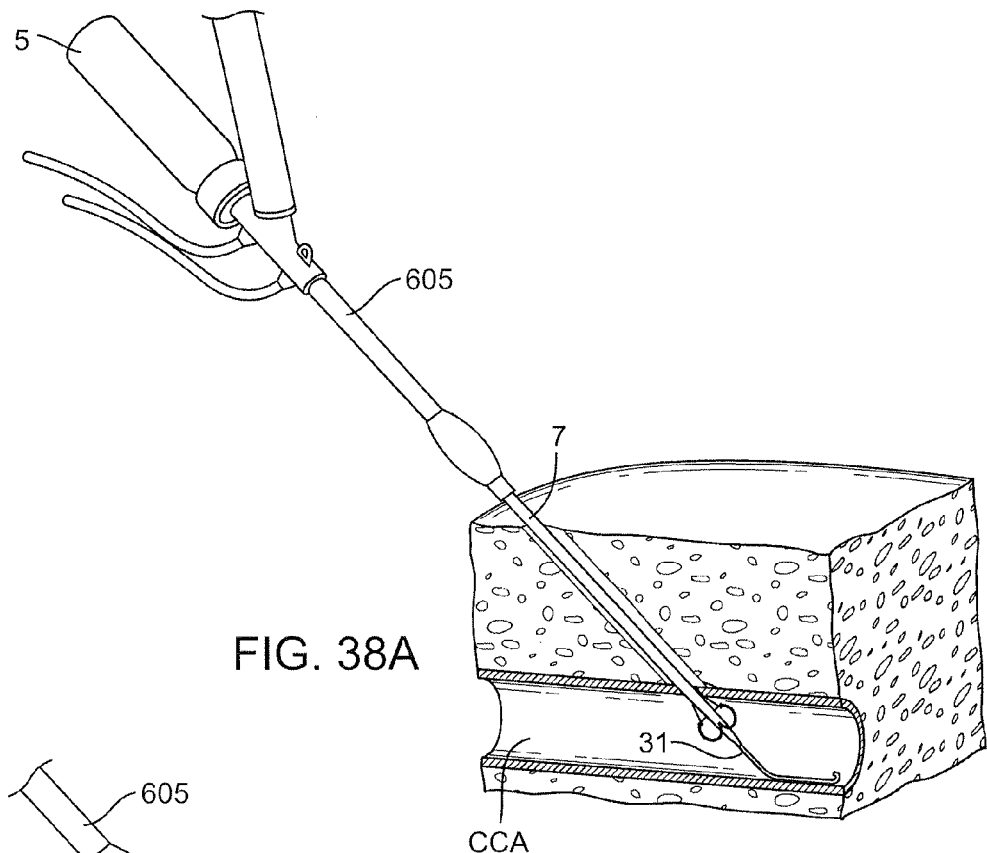

Referring now to FIGS. 38A-38E, 39, 40A-40E, and 41A-41F, an exemplary interventional procedure is described. The procedure is described as a carotid artery stenting procedure although it should be appreciated that the devices described herein can be used with various types of transcatheter and interventional procedures. Initially, as shown in FIG. 38A, the suture delivery device 5 with a pre-mounted distal sheath 41 is inserted into the common carotid artery CCA over a pre-placed guidewire 31. (The common carotid artery CCA is shown schematically in FIGS. 38A-38B and it should be appreciated that the actual anatomical details may differ.) The suture delivery device 5 is positioned relative to the pre-mounted sheath 41 such that a distal region of the suture delivery device's shaft 7 protrudes out of the distal end of the sheath 41 to provide access to the blood vessel wall for the suture delivery device 5. The pre-mounted distal sheath 41 can be in the form of the sheath 605 described above. That is, the pre-mounted distal sheath 41 and the sheath 605 can be one and the same. Or, the pre-mounted distal sheath 41 can be separate from the sheath 605. The following procedure is described in the context of the pre-mounted distal sheath 41 being the sheath 605.

Figure 38B:
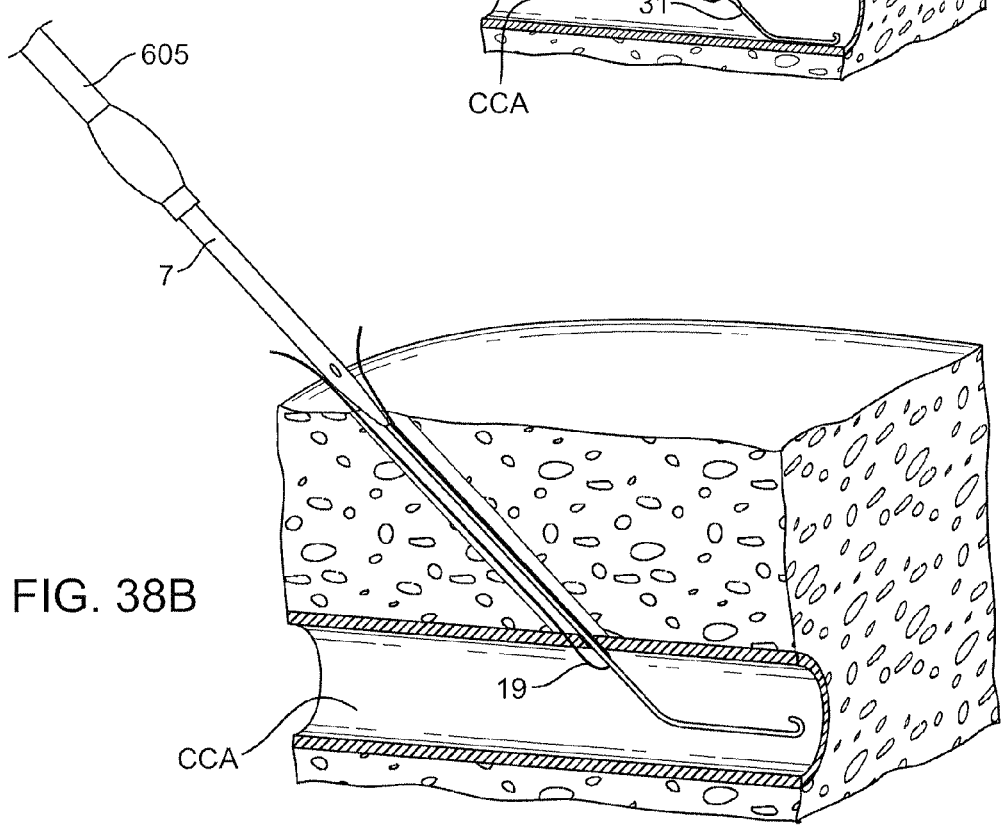
Figure 38C:
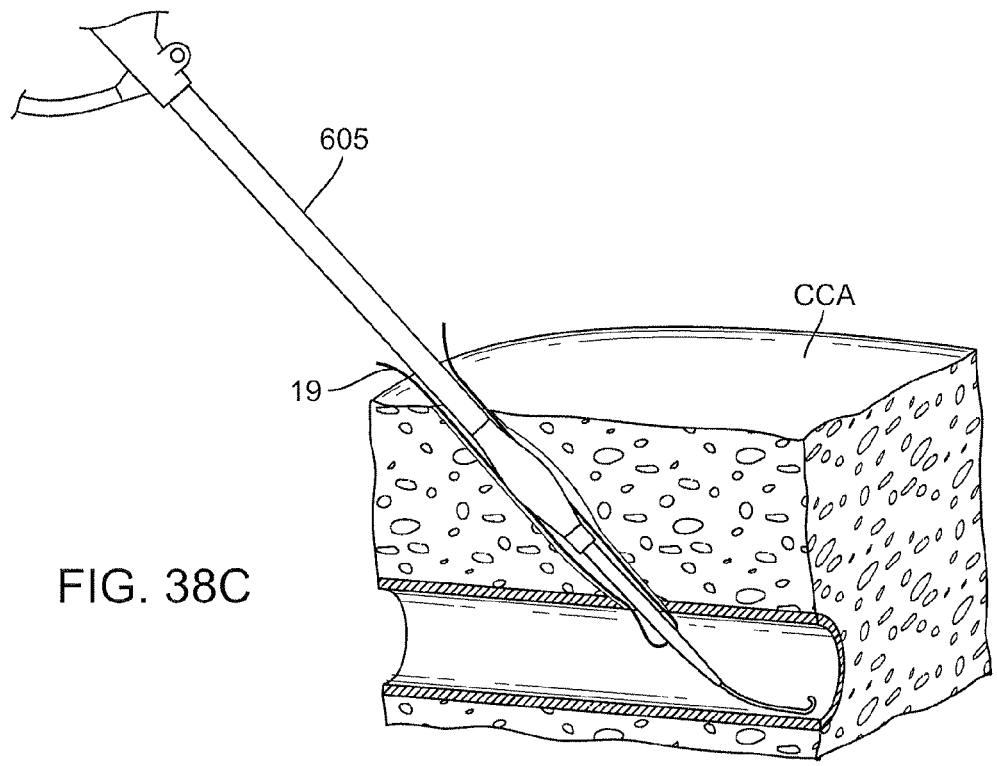

With reference to FIG. 38B, the suture delivery device 5 is then used to deploy closing suture 19 into the vessel wall as described above to achieve pre-placement of the closing suture prior to insertion of the sheath 605 into the vessel. At least one end of the suture 19 is drawn outside the body of the patient using the suture delivery device such that the suture 19 can be held until such time as the suture is to be tied off to create a permanent closure of the arteriotomy. With the suture 19 placed, the distal sheath 605 is then advanced distally over the shaft 7 of the suture delivery device 5 into the vessel such that the distal end of the sheath 605 is positioned in the vessel and a proximal end of the sheath 605 protrudes out of the patient, as shown in FIG. 38C. In this manner, the sheath 605 provides access to the inside of the vessel.

Figure 38D:
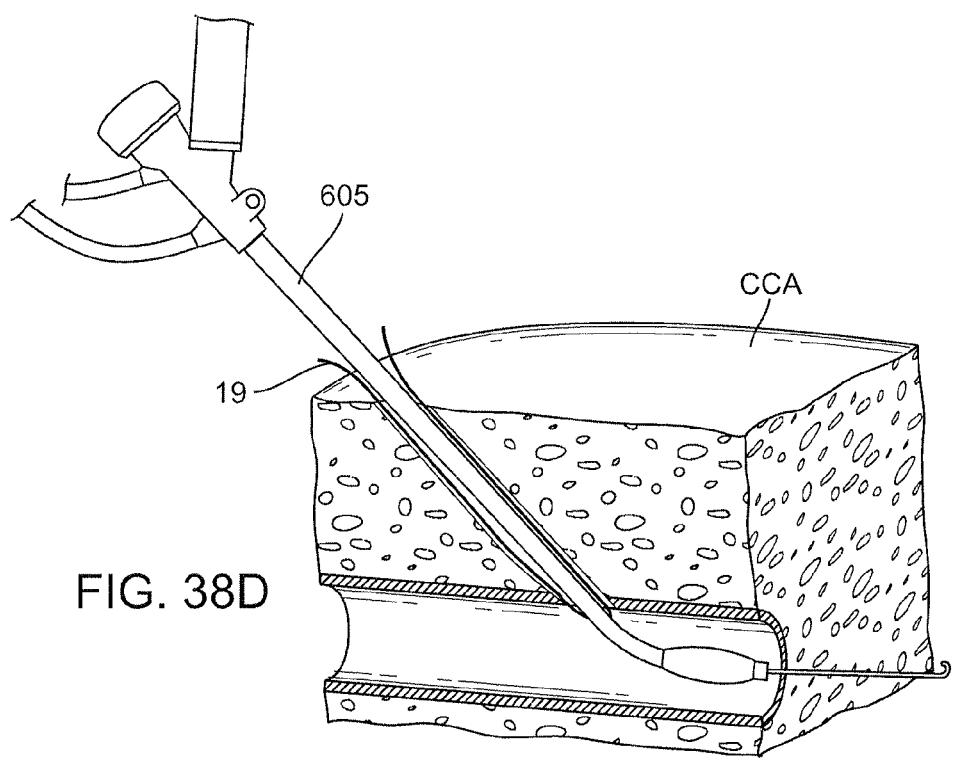
Figure 38E:
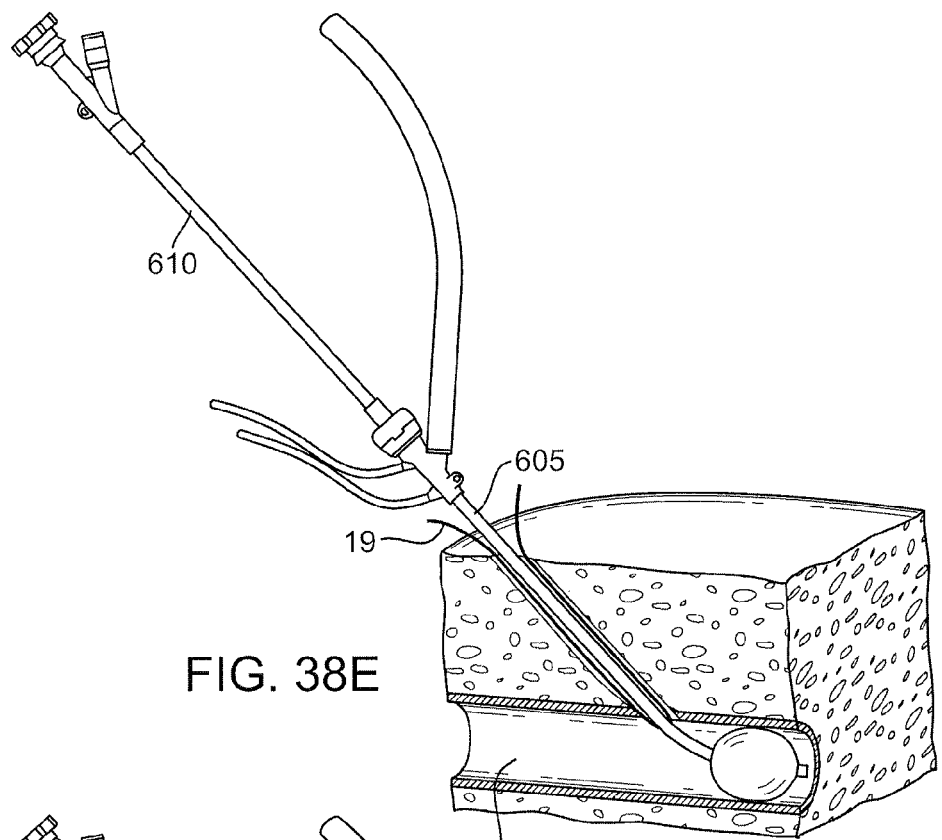

The suture delivery device 5 is then removed from the sheath 605. FIG. 38D shows the sheath 605 positioned to provide access to the interior of the vessel with the suture delivery device removed. In an embodiment, a detachable proximal extension tube 610 may then be attached to the procedural sheath, as shown in FIG. 38E.

Figure 39:
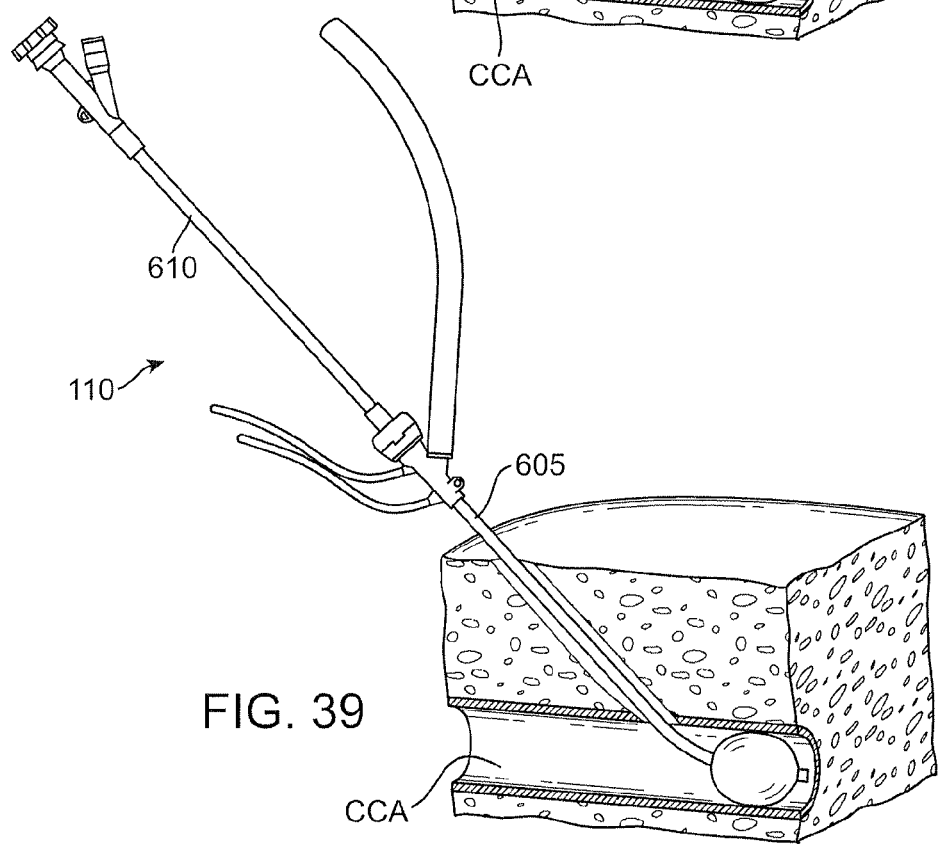

Alternately, as shown in FIG. 39, the arterial access device 110, with the proximal extension tube 610 pre-attached or permanently affixed to the distal sheath 610, may be inserted into the common carotid artery CCA without pre-placement of closing sutures, using either a direct surgical access or a percutaneous access. After the sheath 605 of the arterial access device 110 has been introduced into the common carotid artery CCA, the blood flow will continue in antegrade direction AG with flow from the common carotid artery entering both the internal carotid artery ICA and the external carotid artery ECA, as shown in FIG. 40A.

The venous return device 115 is then inserted into a venous return site, such as the internal jugular vein. The shunt 120 is used to connect the flow lines 615 and 915 of the arterial access device 110 and the venous return device 115, respectively. In this manner, the shunt 120 provides a passageway for retrograde flow from the arterial access device 110 to the venous return device 115. This entire circuit is shown in FIG. 28. In another embodiment, the shunt 120 connects to an external receptacle 130 rather than to the venous return device 115.

Once all components of the system are in place and connected, flow through the common carotid artery CCA is stopped, typically using the occlusion element 129 as shown in FIG. 40B. The occlusion element 129 is expanded at a location proximal to the distal opening of the sheath 605 to occlude the CCA. Alternately, a tourniquet or other external vessel occlusion device can be used to occlude the common carotid artery CCA to stop flow therethrough. In an alternative embodiment, the occlusion element 129 is introduced on second occlusion device 112 separate from the distal sheath 605 of the arterial access device 110. The ECA may also be occluded with a separate occlusion element, either on the same device 110 or on a separate occlusion device.

At that point retrograde flow RG from the external carotid artery ECA and internal carotid artery ICA will begin and will flow through the sheath 605, the flow line 615, the shunt 120, and into the venous return device 115 via the flow line 915. The flow control assembly 125 regulates the retrograde flow as described above. FIG. 40B shows the occurrence of retrograde flow RG. While the retrograde flow is maintained, a stent delivery catheter 2110 is introduced into the sheath 605, as shown in FIG. 40C. The stent delivery catheter 2110 is introduced into the sheath 605 through the hemostasis valve 615 and the proximal extension 610 (not shown in FIGS. 40A-40E) of the arterial access device 110. The stent delivery catheter 2110 is advanced into the internal carotid artery ICA and a stent 2115 deployed at the bifurcation B, as shown in FIG. 40D.

The rate of retrograde flow can be increased during periods of higher risk for emboli generation for example while the stent delivery catheter 2110 is being introduced and optionally while the stent 2115 is being deployed. The rate of retrograde flow can be increased also during placement and expansion of balloons for dilatation prior to or after stent deployment. An atherectomy can also be performed before stenting under retrograde flow.

Still further optionally, after the stent 2115 has been expanded, the bifurcation B can be flushed by cycling the retrograde flow between a low flow rate and high flow rate. The region within the carotid arteries where the stent has been deployed or other procedure performed may be flushed with blood prior to reestablishing normal blood flow. In particular, while the common carotid artery remains occluded, a balloon catheter or other occlusion element may be advanced into the internal carotid artery and deployed to fully occlude that artery. The same maneuver may also be used to perform a post-deployment stent dilatation, which is typically done currently in self-expanding stent procedures. Flow from the common carotid artery and into the external carotid artery may then be reestablished by temporarily opening the occluding means present in the artery. The resulting flow will thus be able to flush the common carotid artery which saw slow, turbulent, or stagnant flow during carotid artery occlusion into the external carotid artery. In addition, the same balloon may be positioned distally of the stent during reverse flow and forward flow then established by temporarily relieving occlusion of the common carotid artery and flushing. Thus, the flushing action occurs in the stented area to help remove loose or loosely adhering embolic debris in that region.

Optionally, while flow from the common carotid artery continues and the internal carotid artery remains blocked, measures can be taken to further loosen emboli from the treated region. For example, mechanical elements may be used to clean or remove loose or loosely attached plaque or other potentially embolic debris within the stent, thrombolytic or other fluid delivery catheters may be used to clean the area, or other procedures may be performed. For example, treatment of in-stent restenosis using balloons, atherectomy, or more stents can be performed under retrograde flow In another example, the occlusion balloon catheter may include flow or aspiration lumens or channels which open proximal to the balloon. Saline, thrombolytics, or other fluids may be infused and/or blood and debris aspirated to or from the treated area without the need for an additional device. While the emboli thus released will flow into the external carotid artery, the external carotid artery is generally less sensitive to emboli release than the internal carotid artery. By prophylactically removing potential emboli which remain, when flow to the internal carotid artery is reestablished, the risk of emboli release is even further reduced. The emboli can also be released under retrograde flow so that the emboli flows through the shunt 120 to the venous system, a filter in the shunt 120, or the receptacle 130.

After the bifurcation has been cleared of emboli, the occlusion element 129 or alternately the tourniquet 2105 can be released, reestablishing antegrade flow, as shown in FIG. 40E.

Figure 41A:
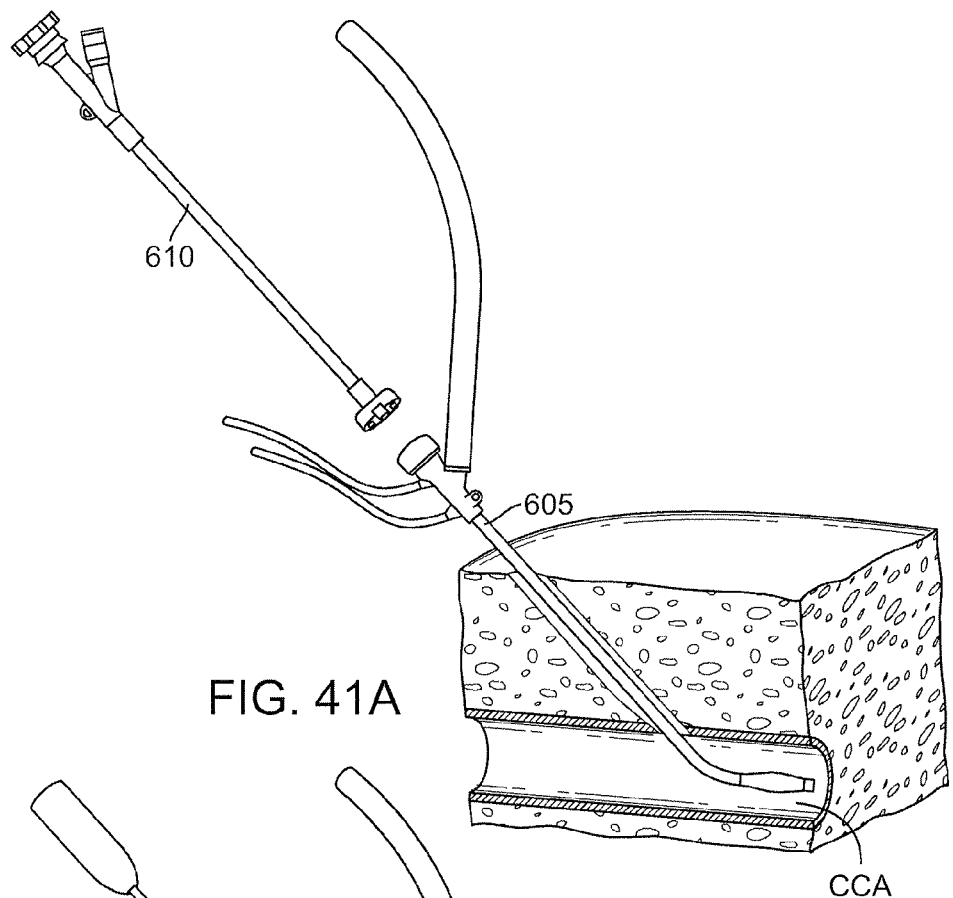
Figure 41B:
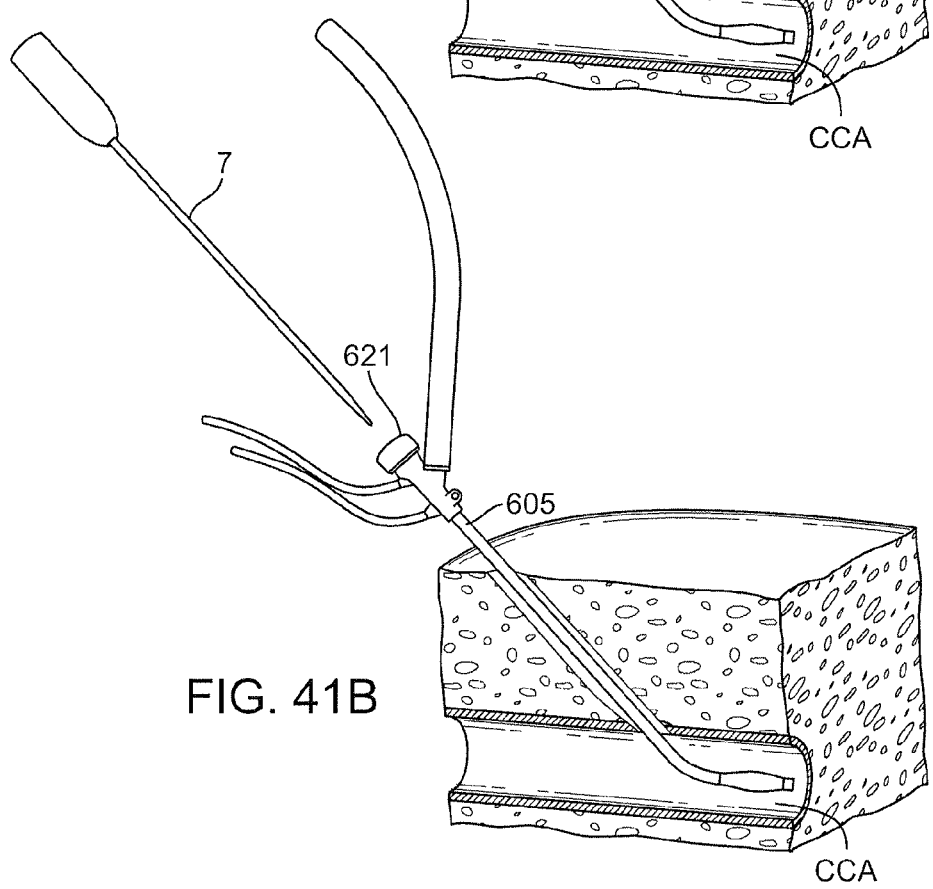
Figure 41C:
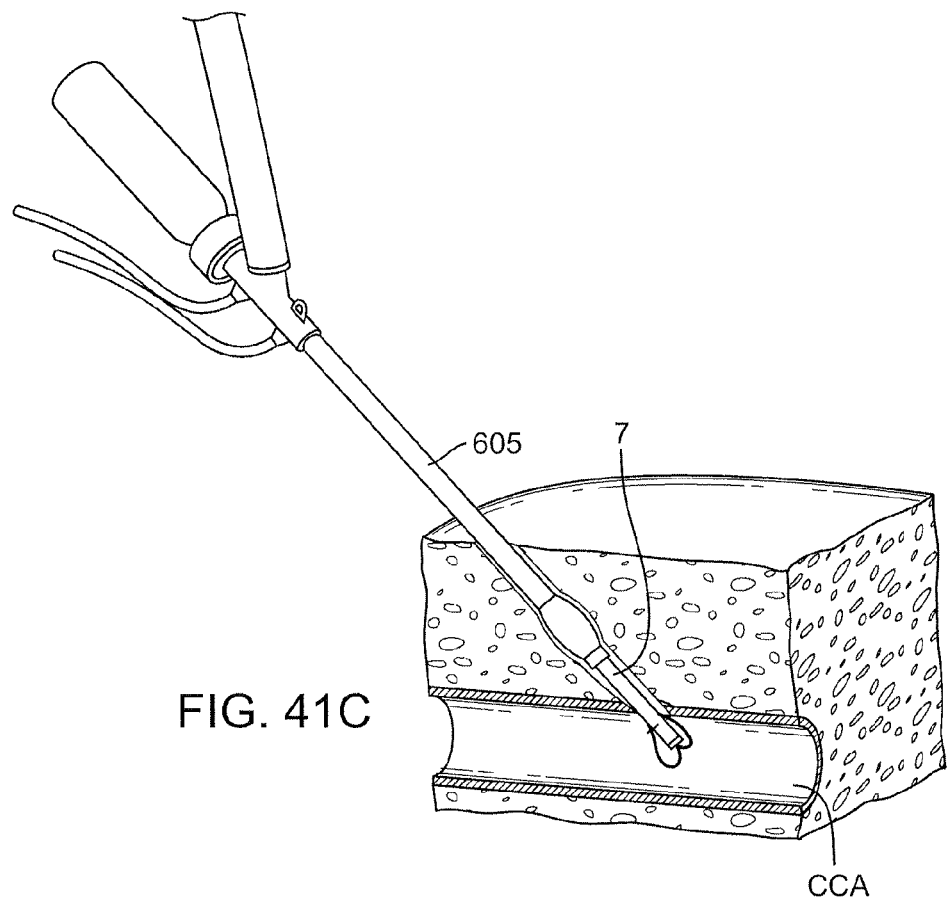
Figure 41D:
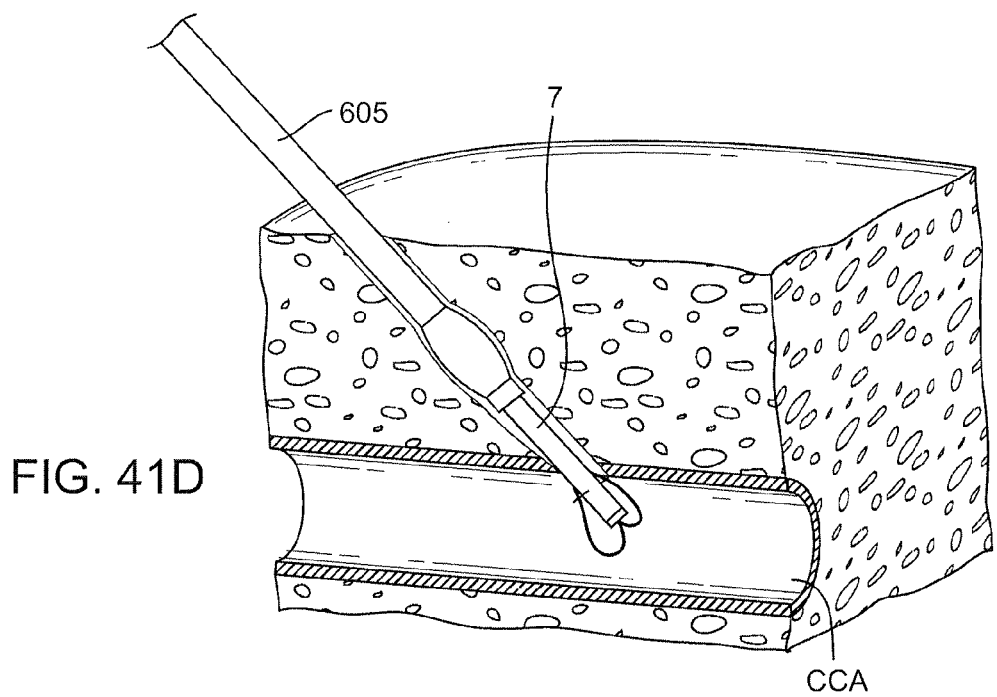
Figure 41E:
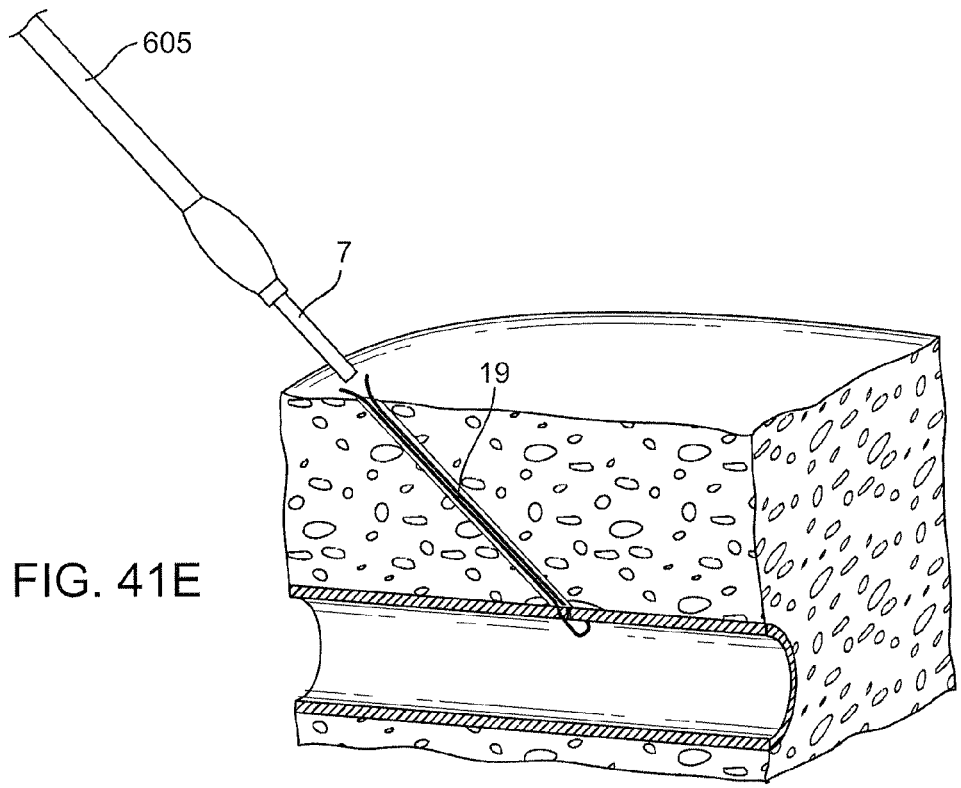
Figure 41F:
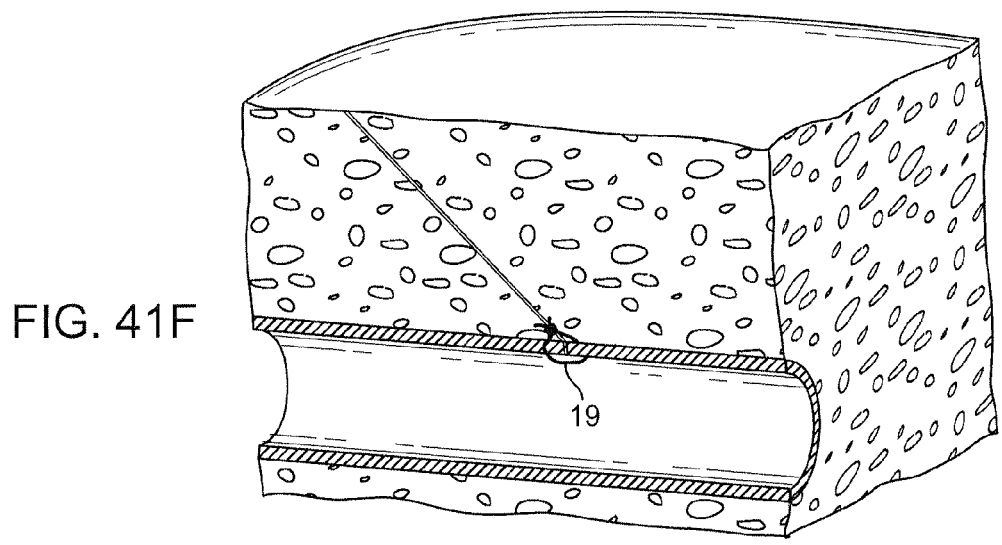

If closing sutures were not preplaced in the vessel at the beginning of the procedure, they may be placed at this time. If the proximal extension tube 610 was attached to the sheath 605 (as shown in FIG. 39), the proximal extension tube 610 is detached from the sheath 605, as shown in FIG. 41A. A suture-based vessel closure device such as described herein is inserted through the hemostasis valve 621 on the distal sheath 605 and into the vessel as shown in FIG. 41B. As shown in FIG. 41C, the distal sheath 605 is then withdrawn proximally to expose the distal region of the suture-based vessel closure device to the vessel wall. This is shown in more detail in the enlarged view of FIG. 41D. The closing suture 19 is then inserted into the vessel wall and the suture-based vessel closure device as well as the sheath 605 are removed from the blood vessel, as shown in FIG. 41E. The suture ends are tied off to achieve hemostasis of the arterial access site, as shown in FIG. 41F.

Alternately, a guidewire is inserted into the arterial access device 110, and the arterial access device 110 is removed, leaving the guidewire in place. A suture closure device such as described herein is advanced over the guidewire into the artery, and the closing suture is inserted into the vessel wall. The device is removed and the suture ends are tied off to achieve hemostasis of the arterial access site.

In an embodiment, the user first determines whether any periods of heightened risk of emboli generation may exist during the procedure. As mentioned, some exemplary periods of heightened risk include (1) during periods when the plaque P is being crossed by a device; (2) during an interventional procedure, such as during delivery of a stent or during inflation or deflation of a balloon catheter or guidewire; (3) during injection or contrast. The foregoing are merely examples of periods of heightened risk. During such periods, the user sets the retrograde flow at a high rate for a discreet period of time. At the end of the high risk period, or if the patient exhibits any intolerance to the high flow rate, then the user reverts the flow state to baseline flow. If the system has a timer, the flow state automatically reverts to baseline flow after a set period of time. In this case, the user may re-set the flow state to high flow if the procedure is still in a period of heightened embolic risk.

In another embodiment, if the patient exhibits an intolerance to the presence of retrograde flow, then retrograde flow is established only during placement of a filter in the ICA distal to the plaque P. Retrograde flow is then ceased while an interventional procedure is performed on the plaque P. Retrograde flow is then re-established while the filter is removed. In another embodiment, a filter is places in the ICA distal of the plaque P and retrograde flow is established while the filter is in place. This embodiment combines the use of a distal filter with retrograde flow.

As will be apparent to those of skill in the art upon reading this disclosure, each of the individual embodiments described and illustrated herein has discrete components and features which may be readily separated from or combined with the features of any of the other several embodiments without departing from the scope of the subject matter described herein. Any recited method can be carried out in the order of events recited or in any other order which is logically possible.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method of performing a procedure on a vascular or cardiac structure, comprising:
   inserting a suture delivery device with a premounted sheath into the common carotid artery through an arteriotomy in the wall of the common carotid artery;
   drawing at least one end of a suture outside the body of the patient using the suture delivery device such that the suture can be held until such time as the suture is to be tied off to create a permanent closure of the arteriotomy;
   separating the suture from the body of the suture delivery device;
   advancing the premounted sheath through the arteriotomy into the common carotid artery;
   removing the suture delivery device;
   inserting a therapeutic device or devices through the sheath to the treatment site, performing a therapeutic procedure, and removing the therapeutic device or devices from the sheath;
   removing the sheath; and
   tying off the ends of the suture to close the arterial access site.

2. A method as in claim 1, further comprising the step of occluding the common carotid artery.

3. A method as in claim 2, wherein the procedural sheath includes a Y-arm connection to a flow line and further comprising the step of connecting the sheath to a reverse flow shunt.

4. A method as in claim 1, wherein the therapeutic device is a prosthetic aortic valve and the therapeutic procedure is transcatheter aortic valve implantation.

5. A method as in claim 1, wherein the suture delivery device includes a vessel wall locator, and further comprising actuating the vessel wall locator from a first position which is generally in line with the suture delivery device to a second position which is generally extended away from the suture delivery device.

6. A method as in claim 1, further comprising:
   advancing a needle in a proximal to distal direction along at least a portion of an elongate body of the suture delivery device toward an arm of the suture delivery device, the needle being advanced through tissue of the common carotid artery;
   engaging a portion of the needle with the portion of the suture; and
   retracting the needle in a distal to proximal direction to draw the suture through the tissue.

7. A method as in claim 1, wherein the suture delivery device is positioned at least partially within the sheath when the sheath is advanced through the arteriotomy.

8. A method as in claim 1, wherein the premounted sheath includes a sheath retention element, and further comprising the step of actuating the sheath retention element after the sheath has been advanced into the artery.

9. A method as in claim 1, wherein the premounted sheath includes an expandable vessel occlusion element, and further comprising the step of expanding the vessel occlusion element to occlude the artery.

10. A method as in claim 9, wherein the expandable vessel occlusion element is an inflatable balloon, and the step of expanding the vessel occlusion element comprising inflating the balloon.

11. A method as in claim 1, wherein the premounted sheath includes a Y-arm connection to a flow line, and further comprising the step of connecting the sheath to a reverse flow shunt.

12. A method as in claim 1, wherein the premounted sheath includes an attachment for a proximal extension tube, and further comprising the step of attaching the proximal extension tube to the sheath after removing the suture delivery device.

* * * * *